US010550069B2

(12) United States Patent
Anderson et al.

(10) Patent No.: US 10,550,069 B2
(45) Date of Patent: Feb. 4, 2020

(54) L-ORNITHINE PHENYL ACETATE AND METHODS OF MAKING THEREOF

(71) Applicant: OCERA THERAPEUTICS, INC., Hazelwood, MO (US)

(72) Inventors: Keith E. Anderson, San Diego, CA (US); Jim Behling, Eagle River, WI (US); Christine Henderson Dougan, Glasgow (GB); Stephen William Watt, Tranent (GB); Peter Manini, Giubiasco (CH); Attilia Figini, Mendrisio (CH)

(73) Assignee: Ocera Therapeutics, Inc., Hazelwood, MO (US)

( * ) Notice: Subject to any disclaimer, the term of this patent is extended or adjusted under 35 U.S.C. 154(b) by 0 days.

(21) Appl. No.: 16/037,655

(22) Filed: Jul. 17, 2018

(65) Prior Publication Data
US 2018/0319736 A1 Nov. 8, 2018

Related U.S. Application Data

(60) Continuation of application No. 15/469,359, filed on Mar. 24, 2017, now Pat. No. 10,173,964, which is a division of application No. 14/715,481, filed on May 18, 2015, now Pat. No. 9,604,909, which is a division of application No. 14/299,940, filed on Jun. 9, 2014, now Pat. No. 9,034,925, which is a division of application No. 13/937,107, filed on Jul. 8, 2013, now Pat. No. 8,785,498, which is a division of application No. 13/436,642, filed on Mar. 30, 2012, now Pat. No. 8,492,439, which is a division of application No. 12/753,763, filed on Apr. 2, 2010, now Pat. No. 8,173,706.

(60) Provisional application No. 61/166,676, filed on Apr. 3, 2009.

(51) Int. Cl.
*C07C 227/40* (2006.01)
*A61K 31/192* (2006.01)
*C07C 57/32* (2006.01)
*C07C 229/26* (2006.01)
*A61K 31/198* (2006.01)
*A61K 31/205* (2006.01)
*C07C 227/42* (2006.01)
*C07C 51/42* (2006.01)

(52) U.S. Cl.
CPC .......... *C07C 227/40* (2013.01); *A61K 31/192* (2013.01); *A61K 31/198* (2013.01); *A61K 31/205* (2013.01); *C07C 51/42* (2013.01); *C07C 57/32* (2013.01); *C07C 227/42* (2013.01); *C07C 229/26* (2013.01)

(58) Field of Classification Search
None
See application file for complete search history.

(56) References Cited

U.S. PATENT DOCUMENTS

| 3,950,529 | A | 4/1976 | Fischer et al. |
| 4,100,293 | A | 7/1978 | Walser |
| 4,228,099 | A | 10/1980 | Walser |
| 4,284,647 | A | 8/1981 | Brusilow et al. |
| 4,320,146 | A | 3/1982 | Walser |
| 4,352,814 | A | 10/1982 | Walser |
| 4,457,942 | A | 7/1984 | Brusilow et al. |
| 5,139,981 | A | 8/1992 | Kurland |
| 5,405,761 | A | 4/1995 | Makryaleas et al. |
| 5,571,783 | A | 11/1996 | Montagne et al. |
| 5,591,613 | A | 1/1997 | Makryaleas et al. |
| 5,741,524 | A | 4/1998 | Staniforth et al. |
| 5,767,086 | A | 6/1998 | Kauvar et al. |
| 6,083,953 | A | 7/2000 | Nestor et al. |
| 6,258,849 | B1 | 7/2001 | Burzynski |
| 6,451,340 | B1 | 9/2002 | Arimilli et al. |
| 6,503,530 | B1 | 1/2003 | Kang et al. |
| 6,514,953 | B1 | 2/2003 | Armitage et al. |
| 6,768,024 | B1 | 7/2004 | Watson-Straughan et al. |
| 6,943,192 | B2 | 9/2005 | Burzynski |
| 8,173,706 | B2 | 5/2012 | Anderson et al. |
| 8,389,576 | B2 | 3/2013 | Jalan et al. |
| 8,492,439 | B2 | 7/2013 | Anderson et al. |
| 8,785,498 | B2 | 7/2014 | Anderson et al. |
| 8,946,473 | B2 * | 2/2015 | Anderson ............ A61K 31/192 562/496 |

(Continued)

FOREIGN PATENT DOCUMENTS

| AU | 2014250643 A1 | 11/2014 |
| AU | 2015221466 A1 | 9/2015 |

(Continued)

OTHER PUBLICATIONS

Abraldes et al., "Hemodynamic Response to Pharmacological Treatment of Portal Hypertension and Long-Term Prognosis of Cirrhosis", Hepatol. 2003, 37:902-908.

(Continued)

*Primary Examiner* — Jeffrey S Lundgren
*Assistant Examiner* — Michael J Schmitt
(74) *Attorney, Agent, or Firm* — Knobbe, Martens, Olson & Bear, LLP

(57) ABSTRACT

Disclosed herein are forms of L-ornithine phenyl acetate and methods of making the same. A crystalline form may, in some embodiments, be Forms I, II, III and V, or mixtures thereof. The crystalline forms may be formulated for treating subjects with liver disorders, such as hepatic encephalopathy. Accordingly, some embodiments include formulations and methods of administering L-ornithine phenyl acetate.

17 Claims, 22 Drawing Sheets

(56) References Cited

U.S. PATENT DOCUMENTS

| | | | |
|---|---|---|---|
| 9,034,925 B2* | 5/2015 | Anderson | A61K 31/192 |
| | | | 514/576 |
| 9,260,379 B2* | 2/2016 | Anderson | A61K 31/192 |
| 9,566,257 B2 | 2/2017 | Jalan et al. | |
| 9,604,909 B2 | 3/2017 | Anderson et al. | |
| 10,039,735 B2 | 8/2018 | Jalan et al. | |
| 10,173,964 B2* | 1/2019 | Anderson | A61K 31/192 |
| 2003/0105104 A1 | 6/2003 | Burzynski | |
| 2003/0195255 A1 | 10/2003 | Summar | |
| 2004/0152784 A1 | 8/2004 | March | |
| 2004/0229948 A1 | 11/2004 | Summar et al. | |
| 2005/0059150 A1 | 3/2005 | Guarino et al. | |
| 2005/0182064 A1 | 8/2005 | Burzynski | |
| 2006/0045912 A1 | 3/2006 | Truog | |
| 2008/0119554 A1 | 5/2008 | Jalan et al. | |
| 2010/0280119 A1 | 11/2010 | Anderson et al. | |
| 2012/0157526 A1 | 6/2012 | Jalan et al. | |
| 2012/0208885 A1 | 8/2012 | Anderson et al. | |
| 2012/0259016 A1 | 10/2012 | Jalan et al. | |
| 2013/0211135 A1 | 8/2013 | Anderson et al. | |
| 2013/0296429 A1 | 11/2013 | Anderson et al. | |
| 2014/0142186 A1 | 5/2014 | Scharschmidt et al. | |
| 2014/0288327 A1 | 9/2014 | Anderson et al. | |
| 2015/0133684 A1 | 5/2015 | Anderson et al. | |
| 2015/0251990 A1 | 9/2015 | Anderson et al. | |
| 2016/0338982 A1 | 11/2016 | Ruettimann et al. | |
| 2017/0189364 A1 | 7/2017 | Jalan et al. | |
| 2018/0161293 A1 | 6/2018 | Jalan et al. | |
| 2018/0221320 A1 | 8/2018 | Rose et al. | |
| 2019/0070142 A1 | 3/2019 | Jalan et al. | |

FOREIGN PATENT DOCUMENTS

| | | |
|---|---|---|
| CA | 2763894 A1 | 1/2011 |
| CN | 1383815 | 12/2002 |
| CN | 101010087 A | 8/2007 |
| EP | 1179347 | 2/2002 |
| EP | 1334722 | 8/2003 |
| EP | 1374863 | 1/2004 |
| EP | 1541141 | 6/2005 |
| FR | 2113774 A1 | 6/1972 |
| GB | 965637 | 8/1964 |
| GB | 1067742 | 5/1967 |
| GB | 1080599 | 8/1967 |
| GB | 1310658 | 3/1973 |
| GB | 1507951 | 4/1978 |
| JP | H05-221858 | 8/1993 |
| JP | 3273578 | 4/2002 |
| JP | 2011-236160 | 11/2011 |
| JP | S54-163518 | 12/2011 |
| MX | PA03009902 A | 5/2005 |
| WO | WO 1985/04805 | 11/1985 |
| WO | WO 1987/05297 | 9/1987 |
| WO | WO 1997/30167 | 8/1997 |
| WO | WO 2000/071151 | 11/2000 |
| WO | WO 2002/034255 | 5/2002 |
| WO | WO 2002/074302 | 9/2002 |
| WO | WO 2003/037378 | 5/2003 |
| WO | WO 2003/045372 | 6/2003 |
| WO | WO 2003/086074 | 10/2003 |
| WO | WO 2004/019928 | 3/2004 |
| WO | WO 2005/053607 | 6/2005 |
| WO | WO 2005/082023 | 9/2005 |
| WO | WO 2006/056794 | 6/2006 |
| WO | WO 2006/059237 | 6/2006 |
| WO | WO 2014/081977 | 5/2014 |

OTHER PUBLICATIONS

Aggarwal et al., "Predictors of Mortality and Resource Utilization in Cirrhotic Patients Admitted to the Medical ICU", Chest, 2001, vol. 119, Issue 5, pp. 1489-1497.

Albrecht et al., "Contrasting effects of thioacetamide-induced liver damage on the brain uptake indices of ornithine, arginine and lysine: modulation by treatment with ornithine aspartate", Metab Brain Dis., 1996, vol. 11, Issue 3, pp. 229-237.

Albrecht et al., "Increase of the brain uptake index for L-ornithine in rats with hepatic encephalopathy", Neuroreport., 1994, vol. 5, Issue 6, pp. 671-673.

Al-Hassnan et al., "The relationship of plasma glutamine to ammonium and of glycine to acid-base balance in propionic acidaemia", J. Inherit. Metab. Dis., 2003, vol. 26, pp. 89-91.

Al Sibae et al., "Current Trends in the Treatment of Hepatic Encephalopathy", Ther Clin Risk Manag. Jun. 2009, 5(3): 617-626.

Als-Nielsen et al.,, Non-Absorbable Disaccharides for Hepatic Encephalopathy: Systematic Review of Randomised Trials, BMJ, 2004, p. 1-6.

Anadiotis et al., "Ornithine transcarbamylase deficiency and pancreatitis", J Pediatr, 2001, vol. 138, pp. 123-124.

Anonymous,, "Sodium phenylbutyrate for urea cycle enzyme deficiencies." [No authors listed], Med Lett Drugs Ther., Nov. 22, 1996, vol. 38, Issue 988, pp. 105-106.

Australian Examination Report dated Jun. 11, 2014 from Application No. 2010232521, filed Apr. 1, 2010.

Bachmann et al., "Ammonia toxicity to the brain and creatine", Molecular Genetics and Metabolism, 2004, vol. 81, pp. S52-S57.

Balata et al., "Induced hyperammonemia alters neuropsychology, brain MR spectroscopy and magnetization transfer in cirrhosis,", Hepatology, 2003, vol. 4, Issue 37, pp. 931-939.

Batshaw et al., "Alternative pathway therapy for urea cycle disorders: twenty years later", J Pediatr. 2001, 138(1 Suppl): S46-S55.

Batshaw et al., "Effect of sodium benzoate and sodium phenylacetate on brain serotonin turnover in the Ornithine transcarbamylase-deficient sparse-fur mouse", Pediatric Research, 1988, vol. 23, Issue 4, pp. 368-374.

Beale et al., "Early enteral supplementation with key pharmaconutrients improves sequential organ failure assessment score in critically ill patients with sepsis: outcome of a randomized, controlled, double blind trial,", Crit Care Med., 2008, vol. 1, Issue 36, pp. 131-144.

Berg et al., "Pharmacokinetics and cerebrospinal fluid penetration of phenylacetate and phenylbutyrate in the non-human primate", Cancer Chemother Pharmacol. May 2001, 47(5): 385-390. Abstract Only.

Berge et al., "Pharmaceutical Salts", J Pharm Sci, 1977, vol. 66, pp. 1-19.

Berry et al., "Long-term management of patients with urea cycle disorders", J Pediatri, 2001, vol. 138, Issue 1, pp. S56-S61.

Bighley et al., "Salt Forms of Drugs and Absorption" in Encyclopedia of Pharmaceutical Technology, Marcel Dekker, Inc. New York, 1996, pp. 453-499.

Blei et al., Pathophysiology of Cerebral Edema in Fulminant Hepatic Failure, Journal of Hepatology, 1999, p. 771-776, vol. 31, Denmark.

Bleichner, et al., "Frequency of infections in cirrhotic patients presenting with acute gastrointestinal haemorrhage", British Journal of Surgery, 1986, vol. 73, Issue 9, pp. 724-726.

Bongers et al., "Exogenous glutamine: the clinical evidence,", Crit Care Med., 2007, vol. 9 Suppl, Issue 35, pp. S545-S552.

Bosoi et al., Long term oral treatment of ornithine phenylacetate increases lean mass and attenuates brain edema in bile-duct ligated rats. Hepatology Oct. 2015, 62(Suppl 1):953A; Abstract 1523.

Braga et al., "Crystal Polymorphism and Multiple Crystal Forms", Struct Bond, 2009, 132: 25-50 [pub online Feb. 25, 2009].

Briggs et al., "Effect of Ornithine and Lactate on Urea Synthesis in Isolated Hepatocytes", Biochem J, 1976, vol. 160, pp. 205-209.

Bruha et al., "Effect of carvedilol on portal hypertension depends on the degree of endothelial activation and inflammatory changes", Scand J Gastroenter. 2006, 41: 1454-1463.

Brunquell et al., "Electroencephalographic findings in ornithine transcarbamylase deficiency", J Child Neurol, 1999, vol. 14, Issue 8, pp. 533-536.

Brusilow et al., "Amino acid acylation: A mechanism of nitrogen excretion in inborn errors of urea synthesis", Science, 1980, vol. 207, pp. 659-661.

(56) References Cited

OTHER PUBLICATIONS

Brusilow et al., "Treatment of episodic hyperammonemia in children with inborn errors of urea synthesis", The New England Journal of Medicine, 1984, vol. 310, Issue 25, pp. 1630-1634.
Burlina et al., "Long-term treatment with sodium phenylbutyrate in ornithine transcarbamylase-deficient patients", Molecular Genetics and Metabolism, 2001, vol. 72, pp. 351-355.
Butterworth, "Pathophysiology of hepatic encephalopathy: a new look at ammonia", Metab Brain Dis., 2002, vol. 17, Issue 4, pp. 221-227.
Butterworth, "Neuronal cell death in hepatic encephalopathy", Metab Brain Dis. Dec. 2007, 22(3-4): 309-320.
Byrn et al., "Pharmaceutical Solids: A Strategic Approach to Regulatory Considerations", Pharma Res. 1995, 12(7): 945-954.
Caira, M.R., "Crystalline Polymorphism of Organic Compounds", Topic in Current Chemistry 1998, 198: 163-208.
Callado França, et al., Five Days of Ceftriaxone to Treat Spontaneous Bacterial Peritonitis in Cirrhotic Patients, Journal of Gastroenterology, Feb. 2002, p. 119-122 vol. 37, No. 2, Springer, Japan.
Cavarec et al., "Molecular cloning and characterization of a transcription factor for the copia retrotransposon with homology to the BTB-Containing Lola Neurogenic Factor", Mol. Cell. Biol., 1997, vol. 17, Issue 1, pp. 482-494.
Chainuvati et al., "Ornicetil on encephalopathy. Effect of ornicetil (ornithine alpha-ketoglutarate) on encephalopathy in patients with acute and chronic liver disease", Acta Hepatogastro., 1977, vol. 24, Issue 6, pp. 434-439.
Chawla et al., "Challenges in Polymorphism of Pharmaeuticals", CRIPS Mar. 2004, 5(1): 9-12.
Chen et al., "Continuous arteriovenous hemodiafiltration in the acute treatment of hyperammonaemia due to ornithine transcarbamylase deficiency", Renal Failure, 2000, vol. 22, Issue 6, pp. 823-836.
Chinese Office Action dated Feb. 19, 2013 in Application No. 201080021311.6, filed Apr. 1, 2010.
Chinese Office Action dated Sep. 18, 2012 in Application No. 201080021311.6, filed Apr. 1, 2010.
Chinese Office Action dated Sep. 23, 2013 in Application No. 201080021311.6, filed Apr. 1, 2010.
Chinese Office Action dated Jul. 9, 2015 for Application No. 201410392027.X, filed Aug. 11, 2014.
Chinese Office Action dated Apr. 5, 2016 for Application No. 201410392027.X, filed Aug. 11, 2014.
Chung et al., "Cirrhosis and its Complications", Harrison's Principles of Internal Medicine (16th Edition) (2005) 289, pp. 1858-1869.
Clemmesen, et al., Cerebral Herniation in Patients With Acute Liver Failure is Correlated with Arterial Ammonia Concentration, Hepatology, Mar. 1999, p. 648-653, Vo. 29, No. 3, American Association for the Study of Liver Diseases.
ClinicalTrails.gov; William Lee, Med. Uni. S.C.; "Safety Study of Ornithine Phenylacetate to Treat Patients with Acute Liver Failure (STOP-ALF)", ID #NCT01548690; Feb. 2012; 7 pages.
Darmaun et al., "Phenylbutyrate-induced glutamine depletion in humans; effect on leucine metabolism", Am J Physiol Endocrinol Metab., 1998, vol. 274, pp. E801-E807.
Database WPI, Section Ch, Week 200331, Derwent Publications Ltd., London, GB; XP002364873 & CN 1383815 A (Liu W), Dec. 11, 2002 (Abstract Only).
Davies, et al., "L-ornithine and phenylacetate synergistically produce sustained reduction in ammonia and brain water in cirrhotic rats", Hepatology Jul. 2009, 50(1): 155-164.
DeJong et al., "Altered glutamine metabolism in rat portal drained viscera and hindquarter during hyperammonemia", Gastroenterology, 1992, vol. 103, Issue 3, pp. 936-948.
Del Rosario et al., Hyperammonemic encephalopathy, J Clin Gastroenterol, 1997, vol. 25, Issue 4, pp. 682-684.
Demand with Article 34 amendments, filed Feb. 3, 2011 in International Application No. PCT/US2010/029708.

Desjardins et al., "Effect of portacaval anastomosis on glutamine synthetase protein and gene expression in brain, liver and skeletal muscle", Metab Brain Dis., 1999, vol. 14, Issue 4, pp. 273-280.
Dewhirst et al., "Phylogeny of the defined murine microbiota: Altered Schaedler Flora", Appl. Environ Microbiol. 1999, 65(8): 3287-3292.
Dunitz et al., "Disappearing Polymorphs", Acc Chem Res. 1995, 28: 193-200.
Enns et al., "Survival after treatment with phenylacetate and benzoate for urea-cycle disorders,", N Engl J Med., 2007, vol. 22, Issue 356, pp. 2282-2292.
Eurasian Office Action dated May 24, 2016 for Application No. 201500650 filed Jul. 16, 2015.
European Extended Search Report dated Nov. 30, 2012 for Application No. 10759442.6.
European Extended Search Report dated Nov. 9, 2017 for Application No. 17185173.6, filed Aug. 7, 2017.
Fabbri et al., Unresponsiveness of Hepatic Nitrogen Metabolism to Glucagon Infusion in Patients with Cirrhosis: Dependence on Liver Cell Failure, Hepatology 1993, 18(1): 28-35.
Garcia-Tsao, MD, et al., Management and Treatment of Patients with Cirrhosis and Portal Hypertension: Recommendations from the Department of Veterans Affairs Hepatitis C Resource Center Program and the National Hepatitis C Program, Am J Gastroenterol, 2009, p. 1802-1829, Vo. 104.
Garden et al., "Prediction of outcome following acute variceal haemorrhage", Br J Surg., 1985, vol. 72, pp. 91-95.
Gebhardt et al., "Treatment of cirrhotic rats with L-Ornithine-L-Aspartate enhances urea synthesis and lowers serum ammonia levels", J Pharm Exp Thera., 1997, vol. 283, Issue 1, pp. 1-6.
Gonzalez-Navajas et al., "Bacterial DNA in patients with cirrhosis and sterile ascites. Its role as a marker of bacterial translocation and prognostic tool,", Rev Esp Enferm Dig., 2007, vol. 10, Issue 99, pp. 599-603.
Gordon, "Ornithine transcarbamylase deficiency: a urea cycle defect", European Journal of Paediatric Neurology, 2003, vol. 7, pp. 115-121.
Grace et al., "Prevention of initial variceal hemorrhage", Gastroenter Clin North Am., 1992, vol. 21, Issue 1, pp. 149-161.
Grant, D.J.W., "Theory and Origin of Polymorphism" Chapter 1 from Polymorphism in Pharmaceutical Solids, Brittain, Harry G. [Ed.]; Marcel Dekker, Inc., 1999; pp. 1-11.
Greenstein et al., Studies on the Metabolism of Amino Acids and Related Compounds in Vivo. III. Prevention of Ammonia Toxicity by Arginine and Related Compounds, Arch Biochem Biophys, 1956, vol. 64, Issue (2):, pp. 342-354.
Grossi et al., "Amino acids mixtures in prevention of acute ammonia intoxication in dogs", Arch Surg, 1967, vol. 94, pp. 261-266.
Guillory, J.K., "Generation of Polymorphs, Hydrates, Solvates, and Amorphous" Chapter 5 from Polymorphism in Pharmaceutical Solids, Brittain, Harry G. [Ed.]; Marcel Dekker, Inc., 1999, pp. 183-226.
Häberle et al., Hyperammonämie: Ursachen, Diagnostik, Therapie, Dtsch Med Wochenschr, 2004, vol. 129; pp. 1430-1433.
Hamberg, Ole et al., Effects of an Increase in Protein Intake on Hepatic Efficacy for Urea Synthesis in Healthy Subjects and in Patients with Cirrhosis, Journal of Hepatology, 1992, pp. 237-243, Elsevier Science Publishers B.V.
Hass et al., "Detection of subclinical and overt hepatic encephalopathy and treatment control after L-Ornithine-L-Aspartate medication by magnetic resonance spectroscopy (1H-MRS)", Z Gastroenterol, 2005, vol. 43, pp. 373-378.
Häussinger et al., "Hepatic encephalopathy in chronic liver disease: a clinical manifestation of astrocyte swelling and low-grade cerebral edema?", J Hepatol., 2000, vol. 32, Issue 6, pp. 1035-1038.
Herlong et al., "The use of ornithine salts of branched-chain ketoacids in portal-systemic encephalopathy", Ann Intern Med., 1980, vol. 93, Issue 4, pp. 545-550.
Hirayama et al., [Eds], "Organic compound crystal produced handbook—Principles and know-how", Maruzen Co., Ltd., Japan; (Jul. 2008), pp. 17-23, 37-40, 45-51 and 57-65; 31 pages.

(56) References Cited

OTHER PUBLICATIONS

Honda et al., "Successful treatment of severe hyperammonemia using sodium phenylacetate powder prepared in hospital pharmacy", Biol. Pharm. Bull., Sep. 2002, 25(9): 1244-1246.
Hopkins Medicine (http://www.hopkinsmedicine.org/gastroenterology_hepatology/_pdfs/liver/portal_hypertension.pdf; accessed Jun. 22, 2016); 13 pages.
Hursthouse et al., "Why Do Organic Compounds Crystallise Well or Badly or Ever so Slowly? Why is Crystallisation Nevertheless Such a Good Purification Technique?", Organic Process Research & Development, 2009, 13:1231-1240.
Igarashi et al., "Determination of ornithine conjugates of some carboxylic acids in birds by high-performance liquid chromatography", Chem Pharm Bull, 1992, vol. 40, Issue 8, pp. 2196-2198.
Inoue et al., "Biochemical analysis of decreased ornithine transport activity in the liver mitochondria from patients with hyperornithinemia, hyperammonemia and homocitrullinuria", Biochim Biophys Acta., 1988, vol. 964, Issue 1, pp. 90-95.
International Preliminary Report on Patentability dated Jun. 2, 2011 for Application No. PCT/US2010/029708, filed Apr. 1, 2010.
International Search Report and Written Opinion dated Jun. 3, 2010 for PCT/US2010/029708, filed Apr. 1, 2010.
Israel Office Action dated Sep. 30, 2014 for Application No. 215449, filed Apr. 1, 2010.
Iyer et al., "Mouse model for human arginase deficiency", Mol Cell Biol., 2002, vol. 22, Issue 13, pp. 4491-4498.
Jalan et al., "Acute-on-chronic liver failure: pathophysiological basis of therapeutic options", Blood Purif, 2002, vol. 20, pp. 252-261.
Jalan et al., "Moderate hypothermia in patients with acute liver failure and uncontrolled intracranial hypertension,", Gastroenterology, 2004, vol. 5, Issue 127, pp. 1338-1346.
Jalan et al., "The molecular pathogenesis of hepatic encephalopathy", The International Journal of Biochemistry & Cell Biology, 2003, vol. 35, pp. 1175-1181.
Jalan et al., L-Ornithine Phenylacetate (OP): A Novel Treatment for Hyperammonemia and Hepatic Encephalopathy, Medical Hypotheses, 2007, 69(5): 1064-1069, Elsevier Ltd.
Jalan et al., Treatment of Hyperammonemia in Liver Failure: A Tale of Two Enzymes, Gastroenterology, 2009, p. 2048-2051, vol. 1236.
Jalan, Intracranial Hypertension in Acute Liver Failure: Pathophysiological Basis of Rational Management, Seminars in Liver Disease, 2003, p. 271-282, vol. 23, No. 3, Thieme Medical Publisheres, Inc., New York, NY, USA.
James et al., "The conjugation of phenylacetic acid in man, subhuman primates and some non-primate species", Proc R Soc Lond B., 1972, vol. 182, pp. 25-35.
Japanese Office Action dated May 13, 2014 for Application No. 2012-503725, filed Apr. 1, 2010.
Japanese Office Action dated Oct. 21, 2014 for Application No. 2012-503725, filed Apr. 1, 2010.
Japanese Office Action dated Jun. 7, 2016 for Application No. 2012-503725, filed Apr. 1, 2010.
Jeyamani et al., Hepatitis E virus and acute-on-chronic liver failure,, Indian J Gastroentero., 2004, vol. 23, Issue 2, pp. 45-46.
Jiang et al., "L-Ornithine-l-aspartate in the management of hepatic encephalopathy: a meta-analysis", J Gastroenterol Hepatol. 2009, 24(1): 9-14; available online: Sep. 28, 2008.
Jover-Cobos et al., Ornithine phenylacetate revisited; Metabolic Brain Disease 2013, 28(2): 327-331.
Kaiser, S. et al., Ammonia and Glutamine Metabolism in Human Liver Slices: New Aspects on the Pathogenesis of Hyperammonaemia in Chronic Liver Disease, European journal of Clinical Investigation , 1988, vol. 18, pp. 535-542.
Kasumov et al., "New secondary metabolites of phenylbutyrate in humans and rats", Drug Metab Dispos., 2004, vol. 32, Issue 1, pp. 10-19.
Katayama, "Ammonia metabolism and hepatic encephalopathy", Hep. Research, 2004, vol. 30, Issue 1, pp. S71-S78.
Khan et al.,, Frequency of Spontaneous Bacterial Peritonitis in Cirrhotic Patients with Ascites Due to Hepatitis C Virus and Efficacy of Ciprofloxacin in its Treatment, Gomal Journal of Medical Sciences, Jul.-Dec. 2009, p. 149-154, vol. 7, No. 2.
Kircheis et al., "Therapeutic efficacy of L-ornithine-L-aspartate infusions in patients with cirrhosis and hepatic encephalopathy: results of a placebo-controlled, double blind study,", Hepatology, 1997, vol. 6, Issue 25, pp. 1351-1360.
Kojima et al., "Effective Solid Form Selection for the Pharmaceutical Development", J Pharma Science Tech. Sep. 2008, 68(5): 344-349.
Korean Office Action dated Jun. 8, 2016 for Application No. 10-2011-7026256, filed Apr. 1, 2010.
Korean Office Action dated Mar. 30, 2017 for Application No. 10-2011-7026256, filed Apr. 1, 2010.
Larsen et al., "Alternative Pathway Therapy for Hyperammonemia in Liver Failure"; Hepatolory, Jul. 2009, 50(1): 3-5.
Lee et al., Acute Liver Failure: Summary of a Workshop, Hepatology, Apr. 2008, p. 1401-1415, vol. 47, No. 4.
Lee, W. M., Acetaminophen-Related Acute Liver Failure in the United States, Hepatology Research, 2008, p. S3-S8, vol. 38, Suppl. 1, The Japan Society of Hepatology.
Lee et al., "Phase 2 Comparison of a Novel Ammonia Scavenging Agent with Sodium Phenylbutyrate in Patients with Urea Cycle Disorders: Safety, Pharmacokinetics and Ammonia Control", Mol Genet Metab. Mar. 2010, 100(3): 221-228.
Linderoth et al., "Short-term prognosis of community-acquired bacteremia in patients with liver cirrhosis or alcoholism: A population-based cohort study,", Alcohol Clin Exp Res., 2006, Issue 30, pp. 636-641.
Lopez-Talavera et al., "Thalidomide Inhibits Tumor Necrosis Factor alpha, Decreases Nitric Oxide Synthesis, and Ameliorates the Hyperdynamic Circulatory Syndrome in Portal-Hypertensive Rats", Hepatology, 1996, 23(6): 1616-1621.
Lukkarinen, M. et al., Effect of Lysine Infusion on Urea Cycle in Lysinuric Protein Intolerance, Metabolism, May 2000, 49(5): 621-625.
Lukkarinen, M. et al., Oral Supplementation Corrects Plasma Lysine Concentrations in Lysinuric Protein Intolerance, Metabolism, Jul. 2003, 52(7): 935-938.
MacArthur et al., "Pharmacokinetics of sodium phenylacetate and sodium benzoate following intravenous administration as both a bolus and continuous infusion to healthy adult volunteers", Molecular Genetics and Metabolism, 2004, vol. 81, pp. S67-S73.
Maestri et al., "Long-term treatment of girls with ornithine transcarbamylase deficiency", N Engl J Med., 1996, vol. 335, Issue 12, pp. 855-859.
Maestri et al., "Prospective treatment of urea cycle disorders", J Pediatr., 1991, vol. 119, Issue 6, pp. 923-928.
Maev I.V. Application of L-ornitine-L-aspartate in complex therapy of hepatic encephalopathy in liver cirrhosis patients (Engl. Title) koloproktologii, 2002, No. 6, pp. 60-66.
Maier et al., Originalien Activities of Urea-Cycle Enzymes in Chronic Liver Disease, Klinische-Wochenschrift, 1979, vol. 67, pp. 661-665, Springer-Verlag.
Maier, "Therapie der hepatischen Enzephalopathie", Dtsch med Wschr., 1988, vol. 113, pp. 1886-1889.
Matsuoka et al., "Advanced Crystallization Technology of Organic Materials—Control of Size, Morphology, Polymorph and Purity", Pharm Tech, Japan (May 2003) 19(6): 91(955)-101(965).
Meijer et al., Nitrogen Metabolism and Ornithine Cycle Function, Physiological Reviews, Jul. 1990, vol. 70, No. 3, pp. 701-748, The American Physiological Society.
Mendenhall et al., "A new therapy for portal systemic encephalopathy", The American Journal of Gastroenterology, 1986, vol. 81, Issue 7, pp. 540-543.
Mexican Office Action dated Dec. 10, 2013 for Application No. MX/a/2012/013961, filed Nov. 30, 2012.
Mihm et al., "Effect of L-ornithine-L-aspartate (LOLA) on neurometabolites in hepatic encephalopathy (HE)", Hepatology, 2001, vol. 34, Issue 4, pp. 543A.

(56) References Cited

OTHER PUBLICATIONS

Mizock et al., "Septic Encephalopathy—Evidence for altered phenylalanine metabolism and comparison with hepatic encephalopathy", Arch Intern Med, 1990, vol. 150, pp. 443-449.
Mizock, Nutritional Support in Hepatic Encephalopathy, Nutrition, 1999, pp. 220-228, vol. 15, No. 3, Elsevier Science Inc.
Mizutani et al., "Hyperargininemia: Clinical course and treatment with sodium benzoate and phenylacetic acid", Brain Dev., 1983, vol. 5, Issue 6, pp. 555-563.
Moinard et al.,, "Effects of Ornithine 2-Oxoglutarate on Neutrophils in Stressed Rates: Evidence for the Involvement of Nitric Oxide and Polyamines", Clin Sci, 2002, vol. 102, Issue 3, pp. 287-295, London, England.
Mookerjee et al., "Neutrophil dysfunction in alcoholic hepatitis superimposed on cirrhosis is reversible and predicts the outcome,", Hepatology, 2007, vol. 3, Issue 46, pp. 831-840.
Mookerjee et al., "Increased gene and protein expression of the novel eNOS regulatory protein NOSTRIN and a variant in alcoholic hepatitis", Gastroenterology Jun. 2007, 132(7): 2533-2541.
Mouille et al., "Adaptative increase of ornithine production and decrease of ammonia metabolism in rat colonocytes after hyperproteic diet ingestion", Am J Gastroint Liver Physiol., 2004, 287(2), G344-G351.
Nance et al., "Ammonia production in germ-free Eck fistula dogs", Surgery, 1971, vol. 70, Issue 2, pp. 169-174.
Navasa et al., "Bacterial infections in liver cirrhosis,", Ital J Gastroenterol Hepatol., 1999, vol. 7, Issue 31, pp. 616-625.
New Zealand Office Action dated Jan. 8, 2014 for Application No. 619235, filed Dec. 20, 2013.
Newsholme et al., "Glutamine metabolism by lymphocytes, macrophages, and neutrophils: its importance in health and disease,", J Nutr Biochem., 1999, vol. 6, Issue 10, pp. 316-324.
Newsholme, "Why is L-glutamine metabolism important to cells of the immune system in health, postinjury, surgery or infection?", J Nutr., 2001, vol. 9 Suppl, Issue 131, pp. 2515S-2522S.
Ocera Therapeutics, Inc., News Release: Ocera Completes Interim Analysis of OCR-002 in Phase 2b STOP-HE Study for the Treatment of Acute Hepatic Encephalopathy; Globe Newswire; Apr. 1, 2015, 2 pages.
Ocera Therapeutics, Inc., News Release: Ocera Announces Positive Phase 1 Results for Oral OCR-002 in Development for the Prevention of Acute Hepatic Encephalopathy; Globe Newswire; Nov. 16, 2015, 2 pages.
Ocera Therapeutics, Inc., News Release: Ocera Completes Plasma Data from Pilot Phase 1 Study for Orally-available OCR-002 in Development for the Prevention of Acute Hepatic Encephalopathy; Globe Newswire; Jan. 8, 2016, 3 pages.
Olde Damink et al., "Decreased plasma and tissue isoleucine levels after simulated gastrointestinal bleeding by blood gavages in chronic portacaval shunted rats", Gut, 1997, vol. 40, pp. 418-424.
Olde Damink et al., "Interorgan ammonia and amino acid metabolism in metabolically stable patients with cirrhosis and a TIPSS", Hepatology, 2002, vol. 36, Issue 5, pp. 1163-1171.
Olde Damink et al., "Interorgan ammonia metabolism in liver failure", Neurochemistry International, 2002, vol. 41, pp. 177-188.
Olde Damink et al., "The kidney plays a major role in the hyperammonemia seen after simulated or actual GI bleeding in patients with cirrhosis", Hepatology, 2003, vol. 37, pp. 1277-1285.
Olde Damink et al., Stimulated Liver and Muscle Protein Synthesis by Intravenous Isoleucine Supplementation During a Simulated Variceal Bleed in Patients with Cirrhosis of the Liver, Hepatology, Oct. 2001, AASLD Abstracts #50.
Pauwels et al., "Systemic antibiotic prophylaxis after gastrointestinal hemorrhage in cirrhotic patients with a high risk of infection", Hepatology, 1996, vol. 24, Issue 4, pp. 802-806.
Petrowski et al., "Pharmacologic amino acid acylation in the acute hyperammonemia of propionic acidemia", Journal of Neurogenetics, 1987, vol. 4, pp. 87-96.
Plecko et al., "Partial N-acetylglutamate synthetase deficiency in a 13-year-old girl: diagnosis and response to treatment with N-carbamylglutamate", Eur J Pediatr., 1998, vol. 157, pp. 996-998.
Powell et al., "Compendium of Excipients for Parenteral Formulations", PDA J Pharm Sci Technol. 1998, 52(5): 238-311.
Praphanphoj et al., "Three cases of intravenous sodium benzoate and sodium phenylacetate toxicity occurring in the treatment of acute hyperammonemia", J Inherit Metab Dis., 2000, vol. 23, pp. 129-136.
Rajkovic et al., "Mechanisms of abnormalities in host defences against bacterial infection in liver disease,", Clin Sci. (Lond.), 1985, vol. 3, Issue 68, pp. 247-253, London.
Ramaswamy et al., "Mouse model for human arginase deficiency", Mol Cell Biol., Jul. 2002, vol. 22, Issue 13, pp. 4491-4498.
Rees et al., "Effect of L-Ornithine-L-Aspartate on patients with and without TIPS undergoing glutamine challenge: a double blind, placebo controlled trial", Gut, 2000, vol. 47, pp. 571-574.
Riordan et al., "Treatment of hepatic encephalopathy", Curr Concepts, 1997, vol. 337, Issue 7, pp. 473-479.
Rockey et al., "Randomized, Double-Blind, Controlled Study of Glycerol Phenylbutyrate in Hepatic Encephalopathy," Hepatology (2014) 59(3): 1073-1083.
Rogers, Q. R. et al., Deficiency of Pyrroline-5-Carboxylate Synthase in the Intestinal Mucosa of the Cat, J Nutrition, 1985, 115(1): 146-150.
Romero-Gómez et al., "Intestinal glutaminase activity is increased in liver cirrhosis and correlates with minimal hepatic encephalopathy", J Hepatol. 2004, 41: 49-54.
Rose et al., "L-Ornithine-L-Aspartate in experimental portal-systemic encephalopathy: therapeutic efficacy and mechanism of action", Metabolic Brain Disease, 1998, vol. 13, Issue 2, pp. 147-157.
Rose et al., "L-Ornithine-L-Aspartate lowers plasma and cerebrospinal fluid ammonia and prevents brain edema in rats with acute liver failure", Hepatology, 1999, vol. 30, Issue 3, pp. 636-640.
Rudman et al., Maximal Rates of Excretion and Synthesis of Urea in Normal and Cirrhotic Subjects, The Journal of Clinical Investigation, Sep. 1973, vol. 52, pp. 2241-2249.
Rukmini et al., "Region-specific changes in CNS muscarinic acetylcholine receptors in a rat model of hyperammonemia", Biochem Pharmacol., 1998, vol. 56, Issue 2, pp. 237-241.
Sanyal et al., Portosystemic Encephalopathy After Transjugular Intrahepatic Portosystemic Shunt: Results of a Prospective Controlled Study, Hepatology, 1994, p. 46-55, vol. 20, No. 1, Pt. 1, The American Association for the Study of Liver Diseases.
Sanyal, A. J., Prediction of Variceal Hemorrhage in Patients with Cirrhosis, UpToDate, Inc., Website (www.uptodate.com), Jan. 2010, UpToDate.
Sarhan et al., "Effects of inhibition of ornithine aminotransferase on thioacetamide-induced hepatogenic encephalopathy", Neurochem Res., 1993, vol. 18, Issue 4, pp. 539-549.
Scaglia et al., "Effect of alternative pathway therapy on branched chain amino acid metabolism in urea cycle disorder patients", Mol Genet Metabolism, 2004, vol. 81, pp. S79-S85.
Sears et al., "Disruption of the blood-brain barrier in hyperammonaemic coma and the pharmacologic effects of dexamethasone and difluoromethyl ornithine", J Neurosci Res., 1985, vol. 14, Issue 2, pp. 255-261.
Seiler et al., "Ornithine aminotransferase activity, liver ornithine concentration and acute ammonia intoxication", Life Sciences, 1989, vol. 45, Issue 11, pp. 1009-1020.
Seiler, "Ornithine aminotransferase, a potential target for the treatment of hyperammonemias", Curr Drug Targets., Sep. 2000, vol. 1, Issue 2, pp. 119-153.
Sen et al., "The pathophysiological basis of acute-on-chronic liver failure", Liver, 2002, vol. 22, Issue Suppl. 2, pp. 5-13.
Shangraw et al., Effect of Liver Disease and Transplantation on Urea Synthesis in Humans: Relationship to Acid-Base Status, AM J Physiol Gastrointest Liver Physiol, 1999, vol. 276, pp. 1145-1152.
Shawcross et al., "Ammonia impairs neutrophil phagocytic function in liver disease,", Hepatology, 2008, vol. 4, Issue 48, pp. 1202-1212.
Shawcross et al., "Dispelling myths in the treatment of hepatic encephalopathy,", Lancet, 2005, vol. 9457, Issue 365, pp. 431-433.

(56) References Cited

OTHER PUBLICATIONS

Shawcross et al., "Hyperammonemia impairs neutrophil function", Hepatology, 2005, vol. 42, pp. 537A.
Shriner et al., "Recrystallization", Chapter 3.5 Preliminary Examination in the Systematic Identification of Organic Compounds, John Wiley & Sons, Inc. New York, 1998, Chapter 3, pp. 78-81.
Simell et al., "Waste nitrogen excretion via amino acid acylation: benzoate and phenylacetate in lysinuric protein intolerance", Pediatric Research, 1986, vol. 20, Issue 11, pp. 1117-1121.
Singapore Examination Report dated Sep. 27, 2013 for Application No. 201107116-4, filed Apr. 1, 2010.
Singapore Search Report and Written Opinion dated Jul. 11, 2014 from Application No. 2013024559, filed Apr. 2, 2013.
Singaporean Search and Written Opinion dated Mar. 1, 2013 for Application No. 201108982-8, filed Jun. 8, 2010.
Singaporean Search & Examination Report dated Nov. 5, 2013 for Application No. 201108982-8, filed Jun. 8, 2010.
Singh, et al., Changing Epidemiology and Predictors of Mortality in Patients With Spontaneous Bacterial Peritonitis at a Liver Transplant Unit, Clinical Microbiology and Infection, Jun. 2003, p. 531-537, vol. 9, No. 6., European Society of Clinical Microbiology and Infectious Diseases.
Smith et al., "The treatment of inborn errors of the urea cycle", Nature, 1981, vol. 291, Issue 5814, pp. 378-380.
Soláini et al., "Variations in the plasma concentration of ornithine, citrulline and arginine in acute experimental liver failure" [Article in Italian], Boll Soc Ital Biol Sper., 1981, vol. 57, Issue 7, pp. 705-710.
Stedman's Medical Dictionary; "Encephalopathy", 27th Edition, 2002; 1 page.
Stewart, P. M., et al., Effects of Arginine-Free Meals on Ureagenesis in Cats, American Journal of Physiological, 1981, pp. E310-E315, vol. 241, No. 4, The American Physiological Society.
Stravitz, MD, et al., Intensive Care of Patients with Acute Liver Failure: Recommendations of the U.S. Acute Liver Failure Study Group, Critical Care Medicine, 2007, p. 2498-2508, vol. 35, No. 11, Lippincott Williams & Wilkins.
Suchy et al., Clinical Manifestations and Complications—Typical Clinical Presentation;, Liver Disease in Children, 2nd Edition, 2001, pp. 74-77.
Sugarbaker et al., "The role of the small intestine in ammonia production after gastric blood administration", Ann Surg., 1987, vol. 206, Issue 1, pp. 5-17.
Sukhotnik et al., "Oral glutamine prevents gut mucosal injury and improves mucosal recovery following lipopolysaccharide endotoxemia in a rat,", J Surg Res., 2007, vol. 2, Issue 143, pp. 379-384.
Svanberg et al., "Effects of amino acids on synthesis and degradation of skeletal muscle proteins in humans", Am J Physiol., 1996, vol. 271, Issue 4 Pt1, pp. E718-E724.
Timely Data Resource (TDR), IPD Printable Search Results, "Incidence and Prevalence Database, ICD-9 Code: 567. Peritonitis," <URL:http://www.tdrdata.com/IPD/ipd_searchresultsdataprinter.aspx?SessionGUID=ac0c91d8-7 . . . , 7☐27-2010, 7 pages.
Teran et al., "Primary prophylaxis of variceal bleeding in cirrhosis: A cost-effectiveness analysis", Gastroenter., 1997, vol. 112, Issue 2, pp. 473-482.
Trebicka et al., Atorvastatin lowers portal pressure in cirrhotic rats by inhibition of RhoA/Roh-kinase and activation of endothelial nitric oxide synthase, Hepatology, 2007, 46(1): 242-253.
Tuchman, M., et al., Management of Inherited Disorders of Ureagenesis, The Endocrinologist, 2002, vol. 12, No. 2, p. 99-109.
Tuchman, MD et al., "Episodic hyperammonemia in adult siblings with hyperornithinemia, hyperammonemia, and homocitrullinuria syndrome", Arch Neurol., 1990, vol. 47, pp. 1134-1137.
UK Search Report dated Feb. 21, 2005 for GB priority application No. 0426141.8.
Van Berlo et al., "Is increased ammonia liberation after bleeding in the digestive tract the consequence of complete absence of isoleucine in hemoglobin? A study in pigs", Hepatology, 1989, vol. 10, Issue 3, pp. 315-323.
Van Den Berg et al., "The effect of glutamine-enriched enteral nutrition on intestinal microflora in very low birth weight infants: a randomized controlled trial,", Clin Nutr., 2007, vol. 4, Issue 26, pp. 430-439.
Ventura-Cots et al., Safety of ornithine phenylacetate in cirrhotic decompensated patients: an open-label, dose-escalating, single-cohort study; J Clin Gastroenter. (2013) 47(10): 881-887.
Vilstrup, H. et al., Elimination of Infused Amino Acids From Plasma of Control Subjects and of Patients With Cirrhosis of the Liver, European Journal of Clinical Investigation, 1982, vol. 12, pp. 197-202, Blackwell Scientific Publications.
Vogels et al., "L-ornithine vs L-ornithine-L-aspartate as a treatment for hyperammonemia-induced encephalopathy in rats", J Hepatology, 1997, vol. 26, Issue 1, pp. 174-182.
Wasmuth et al., "Patients with acute on chronic liver failure display 'sepsis-like' immune paralysis,", J Hepatol., 2005, vol. 2, Issue 42, pp. 195-201.
Wright et al., "Reduction in Ammonia with L-Ornithine, Phenylacetate (OP) but not Anti-TNF Prevents LPS Induced Brain Edema in Bile-duct Ligated Cirrhotic Rats", Abstract 773; J Hepatology 2009, 50: S283.
Ytrebø et al., "Interorgan ammonia, glutamate, and glutamine trafficking in pigs with acute liver failure,", Am J Physiol Gastrointest Liver Physiol., 2006, vol. 3, Issue 291, pp. G373-G381.
Ytrebø et al., "L-Ornithine Phenylacetate Attenuates Increased Arterial and Extracellular Brain Ammonia and Prevents Intracranial Hypertension in Pigs with Acute Liver Failure", Hepatology, Jul. 2009, 50(1): 165-174.
Yudkoff et al., "In Vivo Nitrogen Metabolism in Ornithine Transcarbamylase Deficiency", J Clin. Invest., Nov. 1996, 98(9): 2167-2173.
Zetterman, Rowen K., MD, "Complications of Portal Hypertension: Hepatic Encephalopathy", Medscape (Jun. 2011) available online at www.medscape.com/viewarticle/744392; downloaded Dec. 3, 2014; 6 pages.
Zieve et al., "Ammonia toxicity: comparative protective effect of various arginine and ornithine derivatives, aspartate, benzoate, and carbamyl glutamate", Metabo Brain Dis., 1986, vol. 1, Issue 1, pp. 25-35.
Zieve et al., "Conditional deficiencies of ornithine or ornithine or arginine", J Am Coll Nutr., 1986, vol. 5, Issue 2, pp. 167-176.
Australian Examination Report dated Feb. 9, 2018 from Application No. 2017202081, filed Mar. 29, 2017.
Chinese Office Action dated Feb. 12, 2018 for Application No. 201710053850.1, filed Jan. 22, 2017.
Eurasian Office Action dated Sep. 27, 2017 for Application No. 201500650 filed Jul. 16, 2015.
India Office Action dated Jul. 26, 2017 for Application No. 7982/DELNP/2011, filed Apr. 1, 2010.
Japanese Office Action dated Sep. 5, 2017 for Application No. 2016-237164, filed Jul. 12, 2016.
Korean Office Action dated Aug. 1, 2017 for Application No. 10-2011-7026256, filed Nov. 3, 2011.
Mexican Office Action dated Oct. 5, 2017 for Application No. MX/a/2014/008993, filed Jul. 24, 2014.
Singapore Examination Report & Written Opinion dated Mar. 8, 2018 for Application No. 10201406300Y, filed Oct. 2, 2014.
Bosoi et al., "Oral Ornithine Phenylacetate Attenuates Muscle Mass Loss and Prevents Hepatic Encephalopathy in BDL Rats", Abstract 23; J Clin Exper Hepatol. (Feb. 2017) 7:S18-S19.
Canbay et al. "L-Ornithine L-Aspartate (LOLA) as a Novel Approach for Therapy of Non-alcoholic Fatty Liver Disease", Drugs 2019, vol. 79(Suppl 1), pp. S39-S44 (first published online Jan. 31, 2019).
Clément et al., "Minimal hepatic encephalopathy leads to hypotension-induced neuronal cell loss in BDL rats", Abstract 51; Hepatology (Oct. 2015) 62(Suppl 1):233A-234A.
Efrati et al., "Effect of sodium benzoate on blood ammonia response to oral glutamine challenge in cirrhotic patients: a note of caution", Am J Gastroenterol. (2000) 95(12):3574-3578. (Abstract).
Feuerstein et al., Cytokines, Inflammation, and Brain Injury: Role of Tumor Necrosis Factor-α. Cerebrovasc Brain Metab Rev. 1994, 6(4):341-360.

(56) References Cited

OTHER PUBLICATIONS

Islam et al., "Sorbitol and lactitol reduce body fat and toxic ammonia levels in rats", Nutrition Res. (2007) 27:440-447.
Maruzen Co., Ltd., "Jikken Kagaku Guide Book (Experimental Chemistry Guide Book)," The Chemical Society of Japan, 1992, 3rd Edition, pp. 130-131.
Maruzen Co., Ltd., "Jikken Kagaku Koza (Zoku) Experimental Chemistry Course (cont.)", 2. Bunri to Seisei (Isolation and Purification), Jan. 25, 1967, pp. 159-162 and 184-193.
Pahan et al., Lovastatin and Phenylacetate Inhibit the Induction of Nitric Oxide Synthase and Cytokines in Rat primary Astrocytes, Microglia, and Macrophages, J Clin Invest. BMJ Group GB, 1997, 100(11):2671-2679.
Roque et al., "32* Pro-inflammatory effects of sodium 4-phenylbutyrate in CF lung epithelial cells containing F508del-CFTR", J Cystic Fibrosis 2007, 6: S7.
Smirnov et al., "Ammonia Neutralization and Urea Synthesis in Cardiac Muscle", Circ Res. 1974, 35(Suppl 3):58-73.
Vilatoba et al., Sodium 4-phenylbutyrate protects against liver ischemia reperfusion injury; Surgery, 2005, 138(2):342-351.
Yoneda et al., "Treatment for non-alcoholic steatohepatitis", Separate Igakuno Ayumi, Digestive diseases—state of arts Ver. 3, Oct. 10, 2006, pp. 370-372.

\* cited by examiner

FIG. 2  Digital Scanning Calorimetry Results for Form I

FIG. 3  Thermogravimetric Gravimetric/Differential Thermal Analysis of Form I

FIG. 4   $^1$H nuclear magnetic resonance spectrum obtained from Form I

FIG. 7  Digital Scanning Calorimetry Results for Form II

FIG. 8    Thermogravimetric Gravimetric/Differential Thermal Analysis of Form II FIG. 9  $^1$H nuclear magnetic resonance spectrum obtained from Form II FIG. 13 Thermogravimetric Gravimetric/Differential Thermal Analysis of Form III FIG. 14  $^1$H nuclear magnetic resonance spectrum obtained from Form III FIG. 18 Thermogravimetric Gravimetric/Differential Thermal Analysis of Form V FIG. 19 $^1$H nuclear magnetic resonance spectrum obtained from Form V

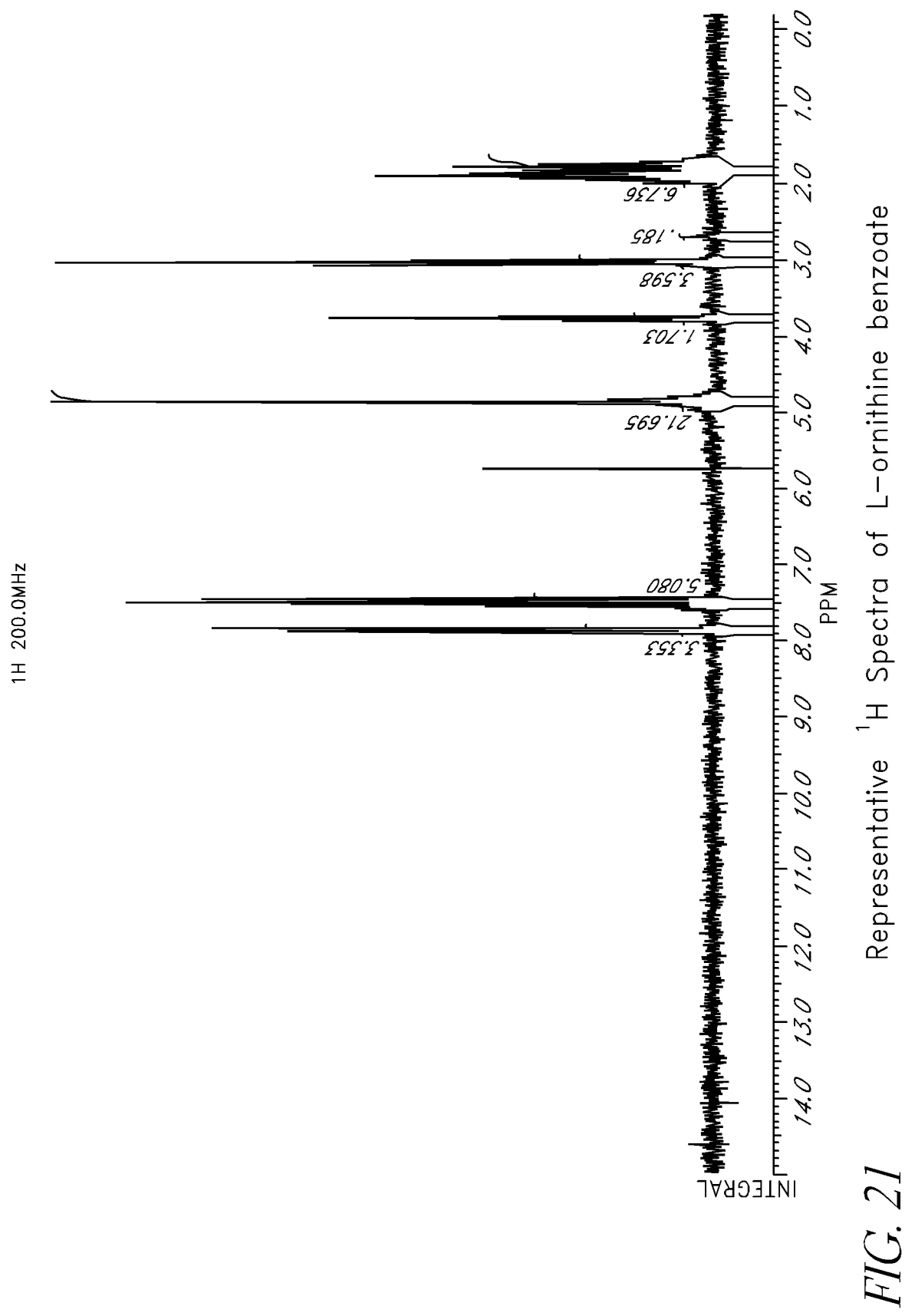
FIG. 21 Representative ¹H Spectra of L-ornithine benzoate

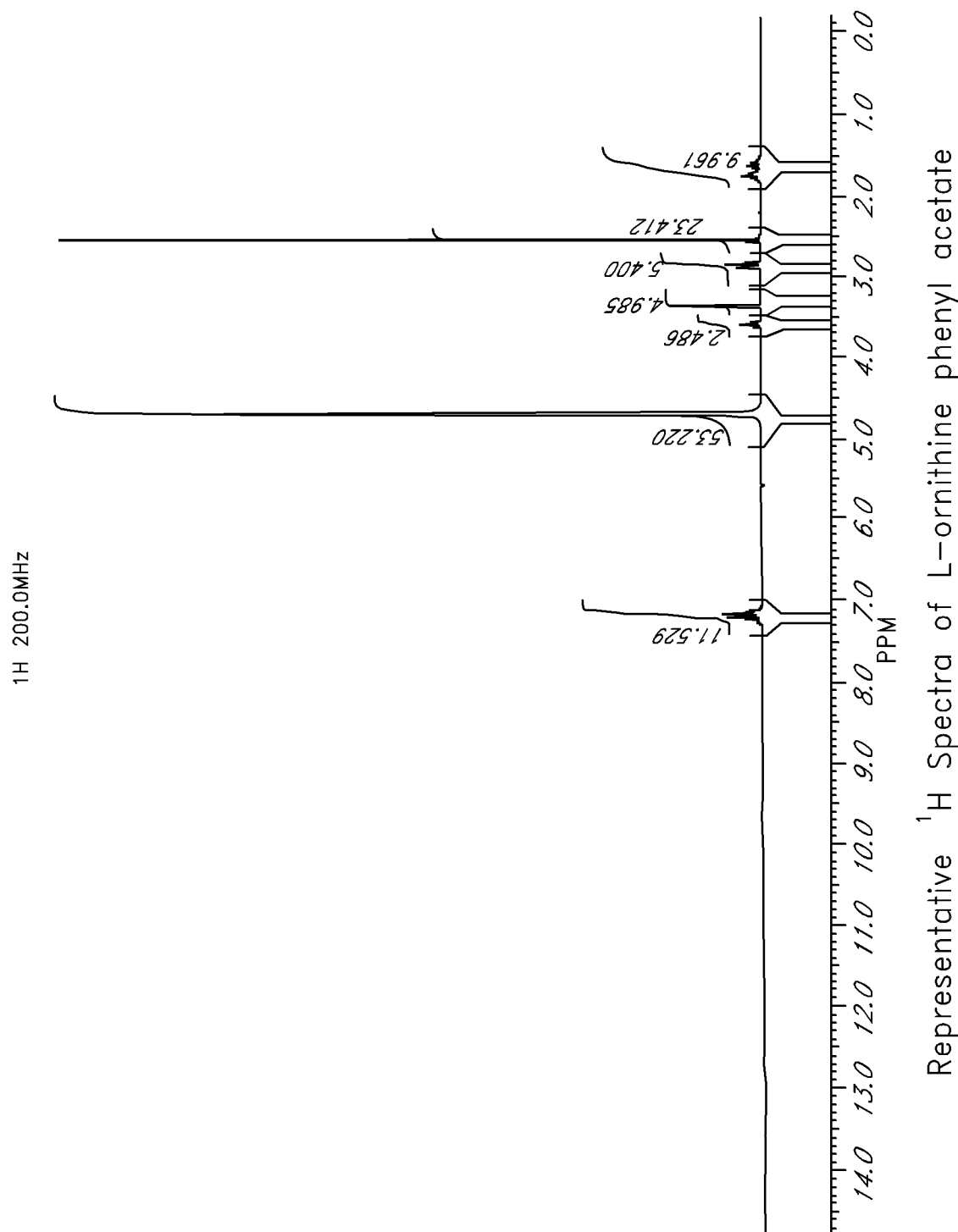
FIG. 22 Representative ¹H Spectra of L-ornithine phenyl acetate

L-ORNITHINE PHENYL ACETATE AND METHODS OF MAKING THEREOF

INCORPORATION BY REFERENCE TO ANY PRIORITY APPLICATIONS

This application is a continuation of U.S. application Ser. No. 15/469,359, filed Mar. 24, 2017; which is a divisional of U.S. application Ser. No. 14/715,481, filed May 18, 2015; which is a divisional of U.S. application Ser. No. 14/299,940, filed Jun. 9, 2014, issued as U.S. Pat. No. 9,034,925; which is a divisional of U.S. application Ser. No. 13/937,107, filed Jul. 8, 2013, issued as U.S. Pat. No. 8,785,498; which is a divisional of U.S. application Ser. No. 13/436,642, filed Mar. 30, 2012, issued as U.S. Pat. No. 8,492,439; which is a divisional of U.S. application Ser. No. 12/753,763, filed Apr. 2, 2010, issued as U.S. Pat. No. 8,173,706; which claims the benefit of priority of U.S. Provisional Application No. 61/166,676, filed Apr. 3, 2009. The priority documents are hereby incorporated by reference in their entireties. This application relates to PCT/US2010/029708, filed Apr. 1, 2010, which was published in English as WO 2010/115055 A1 and designates the United States, and is hereby incorporated by reference in its entirety. Any and all applications for which a foreign or domestic priority claim is identified in the Application Data Sheet as filed with the present application, or any correction thereto, are hereby incorporated by reference under 37 CFR 1.57.

BACKGROUND

Field

The present application relates to the fields of pharmaceutical chemistry, biochemistry, and medicine. In particular, it relates to L-ornithine phenyl acetate salts and methods of making and using the same.

Description

Hyperammonemia is a hallmark of liver disease and is characterized by an excess of ammonia in the bloodstream. Hepatic encephalopathy is a primary clinical consequence of progressive hyperammonemia and is a complex neuropsychiatric syndrome, which may complicate acute or chronic hepatic failure. It is characterized by changes in mental state including a wide range of neuropsychiatric symptoms ranging from minor signs of altered brain function to overt psychiatric and/or neurological symptoms, or even deep coma. The accumulation of unmetabolized ammonia has been considered as the main factor involved in the pathogenesis of hepatic encephalopathy, but additional mechanisms may be associated.

L-Ornithine monohydrochloride and other L-ornithine salts are available for their use in the treatment of hyperammonemia and hepatic encephalopathy. For example, U.S. Publication No. 2008/0119554, which is hereby incorporated by reference in its entirety, describes compositions of L-ornithine and phenyl acetate for the treatment of hepatic encephalopathy. L-ornithine has been prepared by enzymatic conversion methods. For example, U.S. Pat. Nos. 5,405,761 and 5,591,613, both of which are hereby incorporated by reference in their entirety, describe enzymatic conversion of arginine to form L-ornithine salts. Sodium phenyl acetate is commercially available, and also available as an injectable solution for the treatment of acute hyperammonemia. The injectable solution is marketed as AMMONUL.

Although salt forms may exhibit improved degradation properties, certain salts, particularly sodium or chloride salts, may be undesirable when treating patients having diseases associated with the liver disease, such as hepatic encephalopathy. For example, a high sodium intake may be dangerous for cirrhotic patients prone to ascites, fluid overload and electrolyte imbalances. Similarly, certain salts are difficult to administer intravenously because of an increased osmotic pressure, i.e., the solution is hypertonic. High concentrations of excess salt may require diluting large volumes of solution for intravenous administration which, in turn, leads to excessive fluid overload. Accordingly, there exists a need for the preparation of L-ornithine and phenyl acetate salts which are favorable for the treatment of hepatic encephalopathy or other conditions where fluid overload and electrolyte imbalance are prevalent.

SUMMARY

Some embodiments disclosed herein include a composition comprising a crystalline form of L-ornithine phenyl acetate.

In some embodiments, the crystalline form exhibits an X-ray powder diffraction pattern comprising at least one characteristic peak, wherein said characteristic peak is selected from the group consisting of approximately 6.0°, 13.9°, 14.8°, 17.1°, 17.8° and 24.1° 2θ. In some embodiments, the crystalline form exhibits an X-ray powder diffraction pattern comprising at least three characteristic peaks, wherein said characteristic peaks are selected from the group consisting of approximately 6.0°, 13.9°, 14.8°, 17.1°, 17.8° and 24.1° 2θ. In some embodiments, the crystalline form exhibits an X-ray powder diffraction pattern comprising characteristic peaks at approximately 6.0°, 13.9°, 14.8°, 17.1°, 17.8° and 24.1° 2θ.

In some embodiments, the crystalline form has a melting point of about 202° C. In some embodiments, the crystalline form exhibits a single crystal X-ray crystallographic analysis with crystal parameters approximately equal to the following: unit cell dimensions: a=6.594(2) Å, b=6.5448(18) Å, c=31.632(8) Å, α=90°, β=91.12(3)°, γ=90°; Crystal System: Monoclinic; and Space Group: P2$_1$. In some embodiments, the crystalline form is represented by the formula [$C_5H_{13}N_2O_2$][$C_8H_7O_2$].

Some embodiments have the crystalline form exhibit an X-ray powder diffraction pattern comprising at least one characteristic peak, wherein said characteristic peak is selected from the group consisting of approximately 4.9°, 13.2°, 17.4°, 20.8° and 24.4° 2θ. In some embodiments, the crystalline form exhibits an X-ray powder diffraction pattern comprising at least three characteristic peaks, wherein said characteristic peaks are selected from the group consisting of approximately 4.9°, 13.2°, 17.4°, 20.8° and 24.4° 2θ. In some embodiments, the crystalline form exhibits an X-ray powder diffraction pattern comprising characteristic peaks at approximately 4.9°, 13.2°, 17.4°, 20.8° and 24.4° 2θ.

Some embodiments have the crystalline form comprising water and/or ethanol molecules. In some embodiments, the crystalline form comprises about 11% by weight of said molecules as determined by thermogravimetric analysis. In some embodiments, the crystalline form is characterized by differential scanning calorimetry as comprising an endotherm at about 35° C. In some embodiments, the crystalline has a melting point at about 203° C.

Some embodiments have the crystalline form exhibiting a single crystal X-ray crystallographic analysis with crystal parameters approximately equal to the following: unit cell dimensions: a=5.3652(4) Å, b=7.7136(6) Å, c=20.9602(18) Å, α=90°, β=94.986(6)°, γ=90°; Crystal System: Monoclinic; and Space Group: P2$_1$. In some embodiments, the crystalline form is represented by the formula [C$_5$H$_{13}$N$_2$O$_2$][C$_8$H$_7$O$_2$]EtOH.H$_2$O.

Some embodiments have the crystalline form exhibiting an X-ray powder diffraction pattern comprising at least one characteristic peak, wherein said characteristic peak is selected from the group consisting of approximately 5.8°, 14.1°, 18.6°, 19.4°, 22.3° and 24.8° 2θ. In some embodiments, the crystalline form exhibits an X-ray powder diffraction pattern comprising at least three characteristic peaks, wherein said characteristic peaks are selected from the group consisting of approximately 5.8°, 14.1°, 18.6°, 19.4°, 22.3° and 24.8° 2θ. In some embodiments, the crystalline form exhibits an X-ray powder diffraction pattern comprising characteristic peaks at approximately 5.8°, 14.1°, 18.6°, 19.4°, 22.3° and 24.8° 2θ.

In some embodiments, the crystalline form is characterized by differential scanning calorimetry as comprising an endotherm at about 40° C. In some embodiments, the crystalline form comprises a melting point at about 203° C.

In some embodiments, the crystalline form exhibits an X-ray powder diffraction pattern comprising at least one characteristic peak, wherein said characteristic peak is selected from the group consisting of approximately 13.7°, 17.4°, 19.8°, 20.6° and 23.7° 2θ. In some embodiments, the crystalline form exhibits an X-ray powder diffraction pattern comprising at least three characteristic peaks, wherein said characteristic peak is selected from the group consisting of approximately 13.7°, 17.4°, 19.8°, 20.6° and 23.7° 2θ. In some embodiments, the crystalline form exhibits an X-ray powder diffraction pattern comprising characteristic peaks at approximately 13.7°, 17.4°, 19.8°, 20.6° and 23.7° 2θ.

In some embodiments, the crystalline form is characterized by differential scanning calorimetry as comprising an endotherm at about 174° C. In some embodiments, the crystalline form has a melting point of about 196° C. In some embodiments, the crystalline form comprises a pharmaceutically acceptable carrier.

Some embodiments disclosed herein have a composition comprising: at least about 50% by weight of a crystalline form of L-ornithine phenyl acetate salt and at least about 0.01% by weight benzoic acid or a salt thereof.

In some embodiments, the composition comprises at least about 0.10% by weight benzoic acid or a salt thereof. In some embodiments, the composition comprises no more than 5% by weight benzoic acid or a salt thereof. In some embodiments, the composition comprises no more than 1% by weight benzoic acid or a salt thereof.

In some embodiments, the composition further comprises at least 10 ppm silver. In some embodiments, comprises at least 20 ppm silver. In some embodiments, the composition further comprises at least 25 ppm silver. In some embodiments, comprises no more than 600 ppm silver. In some embodiments, composition comprises no more than 100 ppm silver. In some embodiments, the composition comprises no more than 65 ppm silver.

In some embodiments, about 50 mg/mL of the composition in water is isotonic with body fluids. In some embodiments, the isotonic solution has an osmolality in the range of about 280 to about 330 mOsm/kg.

In some embodiments, the composition has a density in the range of about 1.1 to about 1.3 kg/m$^3$.

Some embodiments disclosed herein include a process for making L-ornithine phenyl acetate salt comprising: intermixing an L-ornithine salt, a benzoate salt and a solvent to form an intermediate solution; intermixing phenyl acetate with said intermediate solution; and isolating a composition comprising at least 70% crystalline L-ornithine phenyl acetate by weight.

In some embodiments, the process comprises removing at least a portion of a salt from said intermediate solution before intermixing the phenyl acetate, wherein said salt is not an L-ornithine salt. In some embodiments, the process comprises adding hydrochloric acid before removing at least a portion of the salt.

In some embodiments, intermixing the L-ornithine, the benzoate salt and the solvent comprises: dispersing the L-ornithine salt in water to form a first solution; dispersing the benzoate salt in DMSO to form a second solution; and intermixing said first solution and said second solution to form said solution.

In some embodiments, the composition comprises at least about 0.10% by weight benzoate salt. In some embodiments, composition comprises no more than 5% by weight benzoate salt. In some embodiments, composition comprises no more than 1% by weight benzoate salt.

In some embodiments, the L-ornithine salt is L-ornithine hydrochloride. In some embodiments, the benzoate salt is silver benzoate.

In some embodiments, the composition comprises at least 10 ppm silver. In some embodiments, composition comprises at least 20 ppm silver. In some embodiments, the composition comprises at least 25 ppm silver. In some embodiments, the composition comprises no more than 600 ppm silver. In some embodiments, the composition comprises no more than 100 ppm silver. In some embodiments, the composition comprises no more than 65 ppm silver.

In some embodiments, the phenyl acetate is in an alkali metal salt. In some embodiments, the alkali metal salt is sodium phenyl acetate.

In some embodiments, the composition comprises no more than 100 ppm sodium. In some embodiments, the composition comprises no more than 20 ppm sodium.

In some embodiments, the L-ornithine is in a halide salt. In some embodiments, the halide salt is L-ornithine hydrochloride.

In some embodiments, the composition comprises no more than 0.1% by weight chloride. In some embodiments, the composition comprises no more than 0.01% by weight chloride.

Some embodiments disclosed herein include a composition obtained by any of the processes disclosed herein.

Some embodiments disclosed herein include a process for making L-ornithine phenyl acetate salt comprising: increasing the pH value of a solution comprising an L-ornithine salt at least until an intermediate salt precipitates, wherein said intermediate salt is not an L-ornithine salt; isolating the intermediate salt from said solution; intermixing phenyl acetic acid with said solution; and isolating L-ornithine phenyl acetate salt from said solution.

In some embodiments, the pH value is increased to at least 8.0. In some embodiments, the pH value is increased to at least 9.0. In some embodiments, increasing the pH value comprises adding a pH modifier selected from the group consisting of sodium hydroxide, potassium hydroxide, sodium methoxide, potassium t-butoxide, sodium carbonate, calcium carbonate, dibutylamine, tryptamine, sodium hydride, calcium hydride, butyllithium, ethylmagnesium bromide or combinations thereof.

Some embodiments disclosed herein include a method of treating or ameliorating hyperammonemia in a subject by administering a therapeutically effective amount of a crystalline form of L-ornithine phenyl acetate salt.

In some embodiments, the crystalline form is administered orally.

In some embodiments, the crystalline form is selected from the group consisting of Form I, Form II, Form III, Form V, wherein: Form I exhibits an X-ray powder diffraction pattern having characteristic peaks at approximately 4.9°, 13.2°, 17.4°, 20.8° and 24.4° 2θ; Form II exhibits an X-ray powder diffraction pattern having characteristic peaks at approximately 6.0°, 13.9°, 14.8°, 17.1°, 17.8° and 24.1° 2θ; Form III exhibits an X-ray powder diffraction pattern having characteristic peaks at approximately 5.8°, 14.1°, 18.6°, 19.4°, 22.3° and 24.8° 2θ; and Form V exhibits an X-ray powder diffraction pattern having characteristic peaks at approximately 13.7°, 17.4°, 19.8°, 20.6° and 23.7° 2θ.

In some embodiments, the crystalline form is Form I. In some embodiments, the crystalline form is Form II. In some embodiments, the crystalline form is Form III. In some embodiments, the crystalline form is Form V.

In some embodiments, the at least two crystalline forms selected from the group consisting of Form I, Form II, Form III and Form V, are administered. In some embodiments, the at least two crystalline forms are administered at about the same time.

In some embodiments, the crystalline form is administered from 1 to 3 times daily. In some embodiments, the therapeutically effective amount is in the range of about 500 mg to about 50 g.

In some embodiments, the subject is identified as having hepatic encephalopathy. In some embodiments, the subject is identified as having hyperammonemia.

Some embodiments disclosed herein include a process for making L-ornithine phenyl acetate salt comprising: intermixing an L-ornithine salt, silver phenyl acetate and a solvent to form a solution, wherein the L-ornithine salt is in halide salt; and isolating L-ornithine phenyl acetate from said solution.

Some embodiments disclosed herein include a method of treating or ameliorating hyperammonemia comprising intravenously administering a therapeutically effective amount of a solution comprising L-ornithine phenyl acetate, wherein said therapeutically effective amount comprises no more than 500 mL of said solution.

In some embodiments, the solution comprises at least about 25 mg/mL of L-ornithine phenyl acetate. In some embodiments, the solution comprises at least about 40 mg/mL of L-ornithine phenyl acetate. In some embodiments, the solution comprises no more than 300 mg/mL. In some embodiments, the solution is isotonic with body fluid.

Some embodiments disclosed herein include a method of compressing L-ornithine phenyl acetate, the method comprising applying pressure to a metastable form of L-ornithine phenyl acetate to induce a phase change.

In some embodiments, the metastable form is amorphous. In some embodiments, the metastable form exhibits an X-ray powder diffraction pattern comprising at least one characteristic peak, wherein said characteristic peak is selected from the group consisting of approximately 4.9°, 13.2°, 20.8° and 24.4° 2θ.

In some embodiments, the pressure is applied for a predetermined time. In some embodiments, the predetermined time is about 1 second or less. In some embodiments, the pressure is at least about 500 psi.

In some embodiments, the phase change yields a composition having a density in the range of about 1.1 to about 1.3 kg/m$^3$ after applying the pressure.

In some embodiments, the phase change yields a composition exhibiting an X-ray powder diffraction pattern comprising at least one characteristic peak, wherein said characteristic peak is selected from the group consisting of approximately 6.0°, 13.9°, 14.8°, 17.1°, 17.8° and 24.1° 2θ.

Some embodiments disclosed herein include a composition obtained by applying pressure to a metastable form of L-ornithine phenyl acetate to induce a phase change.

BRIEF DESCRIPTION OF THE DRAWINGS

FIG. 21 shows the $^1$H nuclear magnetic resonance spectrum obtained from a sample of L-ornithine benzoate.

FIG. 22 shows the $^1$H nuclear magnetic resonance spectrum obtained from a sample of L-ornithine phenyl acetate.

DETAILED DESCRIPTION

Figure 1:
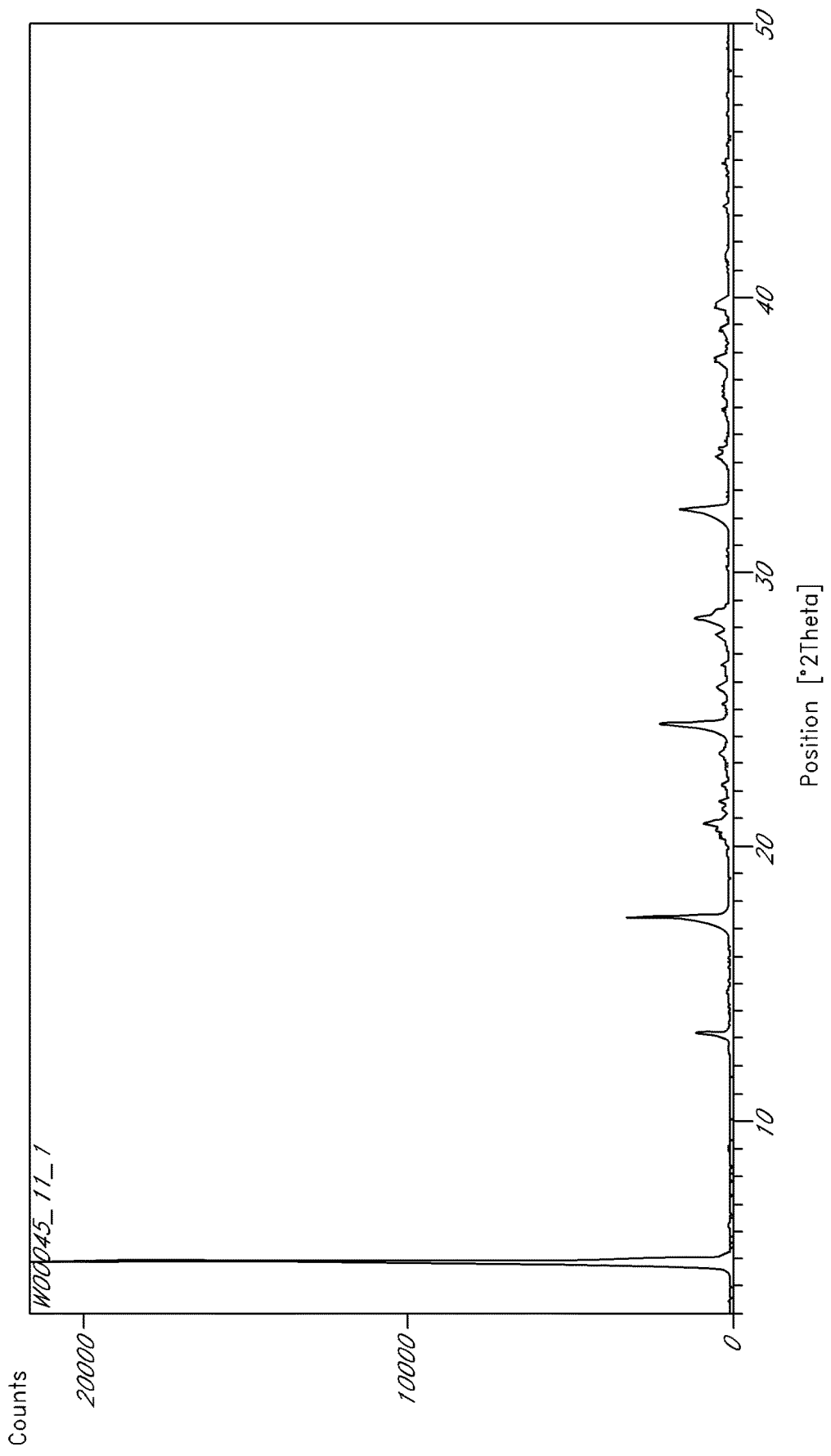
FIG. 1 is an X-ray powder diffraction pattern of Form I.

Disclosed herein are methods of making L-ornithine phenyl acetate salts, and in particular, crystalline forms of said salt. These methods permit large-scale production of pharmaceutically acceptable forms of L-ornithine phenyl acetate using economical processes. Moreover, crystalline forms of L-ornithine phenyl acetate, including Forms I, II, III and V are also disclosed. The L-ornithine phenyl acetate salts permit intravenous administration with negligible concomitant sodium load, and therefore minimize the amount of i.v. fluid that is required.

The present application relates to new crystalline forms of L-ornithine phenyl acetate salts, as well as methods of making and using L-ornithine phenyl acetate salts. The salt advantageously exhibits long-term stability without significant amounts of sodium or chloride. As a result, L-ornithine phenyl acetate is expected to provide an improved safety profile compared to other salts of L-ornithine and phenyl acetate. Also, L-ornithine phenyl acetate exhibits lower tonicity compared to other salts, and therefore can be administered intravenously at higher concentrations. Accordingly, L-ornithine phenyl acetate is expected to provide significant clinical improvements for the treatment of hepatic encephalopathy.

The present application also relates to various polymorphs of L-ornithine phenyl acetate. The occurrence of different crystal forms (polymorphism) is a property of some molecules and molecular complexes. Salt complexes, such as L-ornithine phenyl acetate, may give rise to a variety of solids having distinct physical properties like melting point, X-ray diffraction pattern, infrared absorption fingerprint and NMR spectrum. The differences in the physical properties of polymorphs result from the orientation and intermolecular interactions of adjacent molecules (complexes) in the bulk solid. Accordingly, polymorphs can be distinct solids sharing the same active pharmaceutical ingredient yet having distinct advantageous and/or disadvantageous physicochemical properties compared to other forms in the polymorph family.

Method of Making L-Ornithine Phenyl Acetate Salt

Some embodiments disclosed herein include a method of making L-ornithine phenyl acetate salt. L-Ornithine phenyl acetate may be produced, for example, through an intermediate salt, such as L-ornithine benzoate. As shown in Scheme 1, an L-ornithine salt of Formula I can be reacted with a benzoate salt of Formula II to obtain the intermediate L-ornithine benzoate.

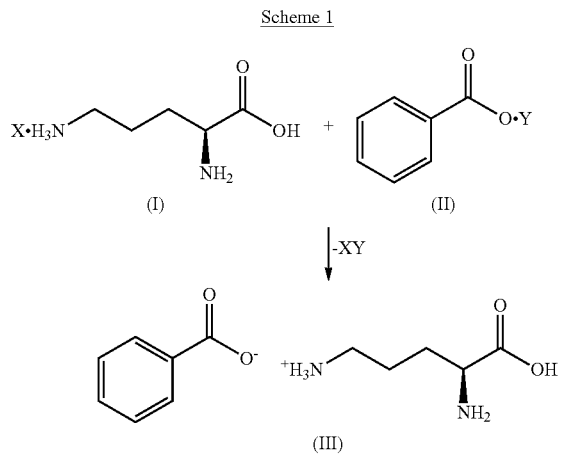

Scheme 1

Various salts of L-ornithine may be used in the compound of Formula I, and therefore X in Formula I can be any ion capable of forming a salt with L-ornithine other than benzoic acid or phenyl acetic acid. X can be a monoatomic anion, such as, but not limited to, a halide (e.g., fluoride, chloride, bromide, and iodide). X can also be a polyatomic anion, such as, but not limited to, acetate, aspartate, formate, oxalate, bicarbonate, carbonate, bitrate, sulfate, nitrate, isonicotinate, salicylate, citrate, tartrate, pantothenate, bitartrate, ascorbate, succinate, maleate, gentisinate, fumarate, gluconate, glucaronate, saccharate, formate, glutamate, methanesulfonate, ethanesulfonate, benzensulfonate, p-toluenesulfonate, pamoate (i.e., 1,1'-methylene-bis-(2-hydroxy-3-naphthoate), phosphate and the like. In some embodiments, X is a monovalent ion. In some embodiments, X is chloride.

Similarly, the benzoate salt of Formula II is not particularly limited, and therefore Y in Formula II can be any appropriate ion capable of forming a salt with benzoic acid. In some embodiments, Y can be a monoatomic cation, such as an alkali metal ion (e.g., Li$^+$, Na$^+$, and K$^+$) and other monovalent ions (e.g., Ag$^+$). Y may also be a polyatomic cation, such as ammonium, L-arginine, diethylamine, choline, ethanolamine, 1H-imidazole, trolamine, and the like. In some embodiments, Y is an inorganic ion. In some embodiments, Y is silver.

Many other possible salts of L-ornithine and benzoic acid may be used for the compounds of Formulae I and II, respectively, and can readily be prepared by those skilled in the art. See, for example, Bighley L. D., et al., "Salt forms of drugs and absorption," In: Swarbrick J., Horlan J. C., eds. Encyclopedia of pharmaceutical technology, Vol. 12. New York: Marcel Dekker, Inc. pp. 452-499, which is hereby incorporated by reference in its entirety.

The intermediate L-ornithine benzoate (i.e., Formula III) can be prepared by intermixing solutions including compounds of Formulae I and II. As an example, the compounds of Formulae I and II may be separately dissolved in water and dimethyl sulfoxide (DMSO), respectively. The two solutions may then be intermixed so that the L-ornithine and benzoic acid react to form the salt of Formula III. Alternatively, the two salt compounds can be directly dissolved into a single solution. In some embodiments, L-ornithine and benzoic acid are dissolved in separate solvents, and subsequently intermixed. In some embodiments, L-ornithine is dissolved in an aqueous solution, benzoic acid is dissolved in an organic solvent, and the L-ornithine and benzoic acid solutions are subsequently intermixed.

Non-limiting examples of solvents which may be used when intermixing L-ornithine and benzoate salts include acetonitrile, dimethylsulfoxide (DMSO), cyclohexane, ethanol, acetone, acetic acid, 1-propanol, dimethylcarbonate, N-methyl-2-pyrrolidone (NMP), ethyl acetate (EtOAc), toluene, isopropyl alcohol (IPA), diisopropoyl ether, nitromethane, water, 1,4 dioxane, tdiethyl ether, ethylene glycol, methyl acetate (MeOAc), methanol, 2-butanol, cumene, ethyl formate, isobutyl acetate, 3-methyl-1-butanol, anisole, and combinations thereof. In some embodiments, the L-ornithine benzoate solution includes water. In some embodiments, the L-ornithine benzoate solution includes DMSO.

Upon intermixing L-ornithine and benzoate salts, counterions X and Y may form a precipitate that can be removed from the intermixed solution using known methods, such as filtration, centrifugation, and the like. In some embodiments, X is chloride, Y is silver, and the reaction produces a precipitate having AgCl. Although Scheme 1 shows the compounds of Formulae I and II as salts, it is also within the scope of the present application to intermix the free base of L-ornithine and benzoic acid to form the intermediate of L-ornithine benzoate. Consequently, forming and isolating the precipitate is optional.

The relative amount of L-ornithine and benzoate salts that are intermixed is not limited; however the molar ratio of L-ornithine to benzoic acid may optionally be in the range of about 10:90 and 90:10. In some embodiments, the molar ratio of L-ornithine benzoate can be in the range of about 30:70 and 30:70. In some embodiments, the molar ratio of L-ornithine to benzoate can be in the range of about 40:60 and 60:40. In some embodiments, the molar ratio of L-ornithine to benzoate is about 1:1.

In embodiments where X and Y are both inorganic ions (e.g., X and Y are chloride and silver, respectively), additional amounts of X-containing salt may be added to encourage further precipitation of the counterion Y. For example, if X is chloride and Y is silver, the molar ratio of L-ornithine hydrochloride to silver benzoate may be greater than 1:1 so that an excess of chloride is present relative to silver. Accordingly, in some embodiments, the molar ratio of L-ornithine to benzoic acid is greater than about 1:1. Nevertheless, the additional chloride salt is not required to be derived from an L-ornithine salt (e.g., L-ornithine hydrochloride). For example, dilute solutions of hydrochloric acid may be added to the solution to further remove silver. Although it is not particularly limited when the additional X-containing salt is added, it is preferably added before the AgCl is initially isolated.

As shown in Scheme 2, the L-ornithine benzoate can be reacted with a phenyl acetate salt of Formula IV to form L-ornithine phenyl acetate. For example, sodium phenyl acetate can be intermixed with a solution of L-ornithine benzoate to form L-ornithine phenyl acetate. Various salts of phenyl acetate may be used, and therefore Z in Formula IV can be any cation capable of forming a salt with phenyl acetate other than benzoic acid or L-ornithine. In some embodiments, Z can be a monoatomic cation, such as an alkali metal ion (e.g., $Li^+$, $Na^+$, and $K^+$) and other monovalent ions (e.g., $Ag^+$). Z may also be a polyatomic cation, such as ammonium, L-arginine, diethylamine, choline, ethanolamine, 1H-imidazole, trolamine, and the like. In some embodiments, Z is an inorganic ion. In some embodiments, Z is sodium.

The relative amount of L-ornithine and phenyl acetate salts that are intermixed is also not limited; however the molar ratio of L-ornithine to phenyl acetate may optionally be in the range of about 10:90 and 90:10. In some embodiments, the molar ratio of L-ornithine to phenyl acetate can be in the range of about 30:70 and 30:70. In some embodiments, the molar ratio of L-ornithine to phenyl acetate can be in the range of about 40:60 and 60:40. In some embodiments, the molar ratio of L-ornithine to benzoic acid is about 1:1.

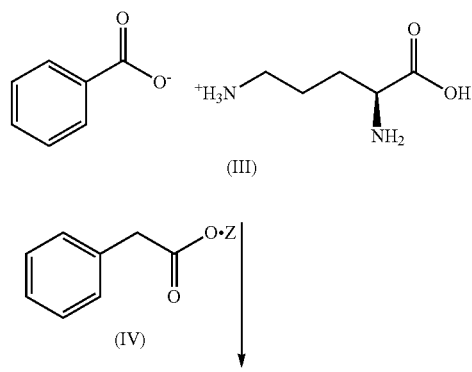

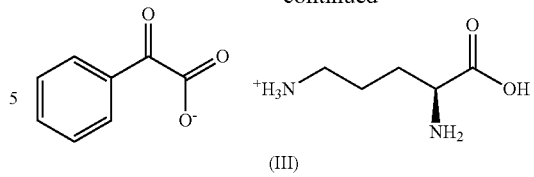

The L-ornithine phenyl acetate of Formula V may then be isolated from solution using known techniques. For example, by evaporating any solvent until the L-ornithine phenyl acetate crystallizes, or alternatively by the adding an anti-solvent miscible in the L-ornithine phenyl acetate solution until the L-ornithine phenyl acetate precipitates from solution. Another possible means for isolating the L-ornithine phenyl acetate is to adjust the temperature of the solution (e.g., lower the temperature) until the L-ornithine phenyl acetate precipitates. As will be discussed in further detail in a later section, the method of isolating the L-ornithine phenyl acetate affects the crystalline form that is obtained.

The isolated L-ornithine phenyl acetate may be subjected to various additional processing, such as drying and the like. In some embodiments, L-ornithine phenyl acetate may be subsequently intermixed with a dilute HCl solution to precipitate residual silver. The L-ornithine phenyl acetate may again be isolated from solution using similar methods disclosed above.

As would be appreciated by a person of ordinary, guided by the teachings of the present application, L-ornithine phenyl acetate may similarly be prepared using an intermediate salt other than L-ornithine benzoate. Thus, for example, L-ornithine, or a salt thereof (e.g., L-ornithine hydrochloride), can be intermixed with a solution having acetic acid. L-Ornithine acetate may then be intermixed with phenyl acetic acid, or a salt thereof (e.g., sodium phenyl acetate), to obtain L-ornithine phenyl acetate. Scheme 4 illustrates an exemplary process of forming L-ornithine phenyl acetate using L-ornithine acetate as an intermediate salt. In some embodiments, the intermediate salt can be a pharmaceutically acceptable salt of L-ornithine. For example, the intermediate L-ornithine salt can be an acetate, aspartate, formate, oxalate, bicarbonate, carbonate, bitrate, sulfate, nitrate, isonicotinate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate, pamoate (i.e., 1,1'-methylene-bis-(2-hydroxy-3-naphthoate) or phosphate. The free acid of the intermediate is preferably a weaker acid relative to phenyl acetic acid. In some embodiments, the intermediate is an L-ornithine salt with an anion component that exhibits a $pK_a$ value that is higher than the $pK_a$ value of phenyl acetic acid. As an example, for L-ornithine acetate, acetic acid and phenyl acetic acid exhibit $pK_a$ values of about 4.76 and 4.28, respectively.

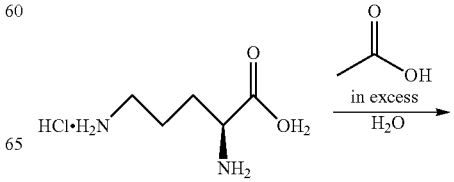

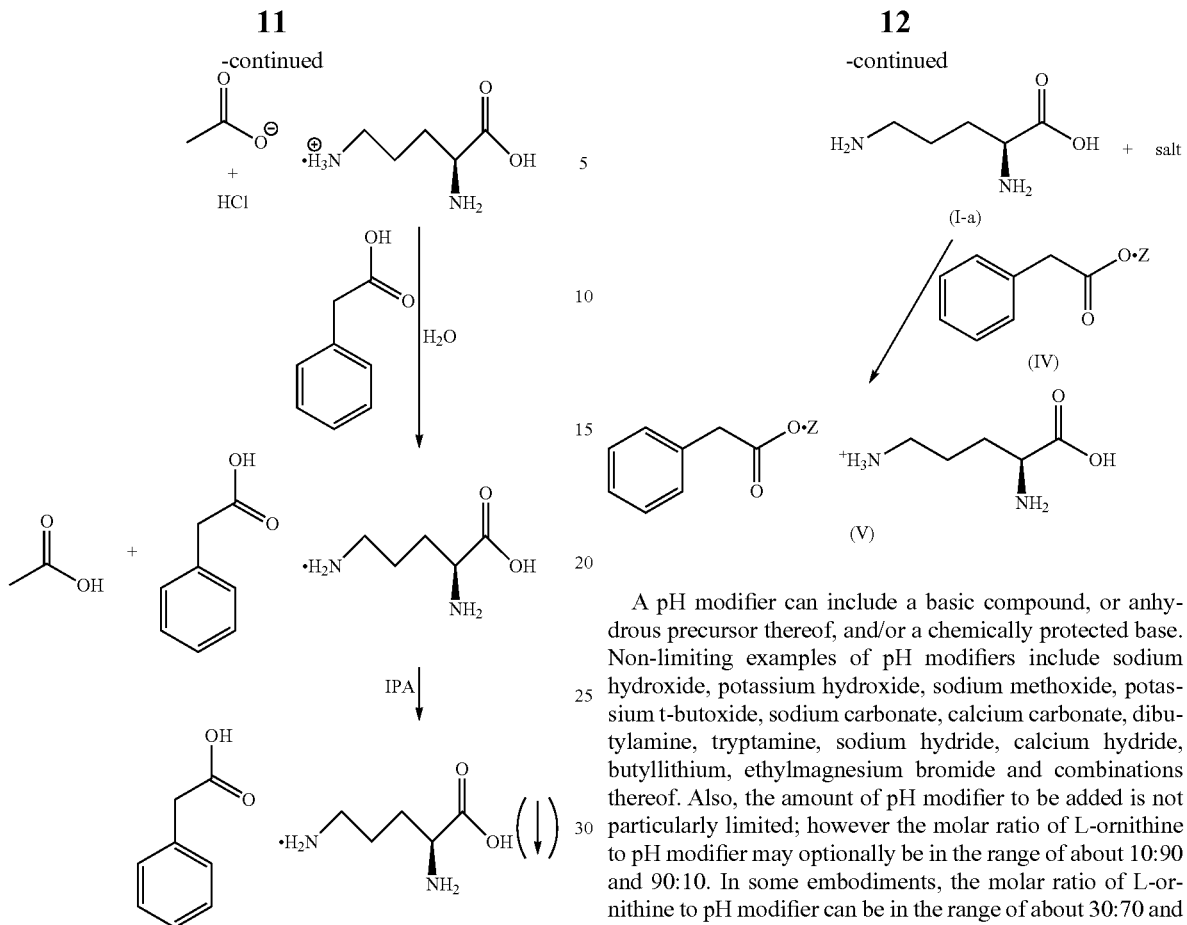

L-Ornithine phenyl acetate may also be prepared, in some embodiments, without forming an intermediate salt, such as L-ornithine benzoate. Scheme 4 illustrates an exemplary process for preparing L-ornithine phenyl acetate without an intermediate salt. A pH modifier may be added to a solution of L-ornithine salt (e.g., as illustrated in Scheme 4 by the compound of Formula I) until a salt precipitates from solution, where the salt is not an L-ornithine salt. As an example, sodium methoxide (NaOMe) can be added to a solution of L-ornithine hydrochloride until sodium chloride precipitates from solution to leave a free base of L-ornithine. The precipitate may optionally be isolated from solution using known techniques, such as filtration, centrifugation, and the like. The free base of L-ornithine (e.g., as illustrated in Scheme 4 by the compound of Formula I-a) may be intermixed with phenyl acetic acid, or a salt thereof (e.g., as illustrated in Scheme 4 by the compound of Formula IV), to obtain L-ornithine phenyl acetate. The L-ornithine phenyl acetate of Formula V may then be isolated as previously described.

Scheme 4

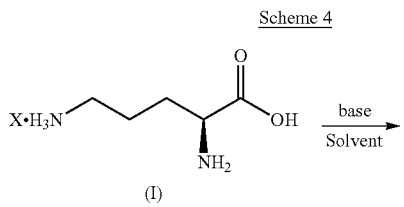

A pH modifier can include a basic compound, or anhydrous precursor thereof, and/or a chemically protected base. Non-limiting examples of pH modifiers include sodium hydroxide, potassium hydroxide, sodium methoxide, potassium t-butoxide, sodium carbonate, calcium carbonate, dibutylamine, tryptamine, sodium hydride, calcium hydride, butyllithium, ethylmagnesium bromide and combinations thereof. Also, the amount of pH modifier to be added is not particularly limited; however the molar ratio of L-ornithine to pH modifier may optionally be in the range of about 10:90 and 90:10. In some embodiments, the molar ratio of L-ornithine to pH modifier can be in the range of about 30:70 and 30:70. In some embodiments, the molar ratio of L-ornithine to pH modifier can be in the range of about 40:60 and 60:40. In some embodiments, the molar ratio of L-ornithine to pH modifier is about 1:1. The pH modifier may, in some embodiments be added to adjust the pH value to at least about 8.0; at least about 9.0; or at least about 9.5.

Another process for forming L-ornithine phenyl acetate, in some embodiments, includes reacting an alkali metal salt of L-ornithine with a phenyl acetate salt. As an example, L-ornithine hydrochloride may be intermixed with silver phenyl acetate and a solvent. AgCl may then precipitate and is optionally isolated from the solution. The remaining L-ornithine phenyl acetate can also be isolated using known methods. This process can be completed using generally the same procedures and conditions outlined above. For example, the relative molar amounts of L-ornithine to phenyl acetate can be 10:90 to 90:10; 30:70 to 70:30; 40:60 to 60:40; or about 1:1. Also, the L-ornithine phenyl acetate may be isolated by evaporating the solvent, adding an anti-solvent, and/or reducing the temperature.

Compositions of L-Ornithine Phenyl Acetate

Also disclosed herein are compositions of L-ornithine phenyl acetate. The compositions of the present application advantageously have low amounts of inorganic salts, particularly alkali metal salts and/or halide salts, and therefore are particularly suited for oral and/or intravenous administration to patients with hepatic encephalopathy. Meanwhile, these compositions may exhibit similar stability profiles compared to other salts (e.g., mixtures of L-ornithine hydrochloride and sodium phenyl acetate). The compositions may, in some embodiments, be obtained by one of the processes disclosed in the present application. For example, any of the disclosed processes using L-ornithine benzoate as an intermediate may yield the compositions of the present application.

The compositions, in some embodiments, can include a crystalline form of L-ornithine phenyl acetate (e.g., Forms I, II, III and/or V disclosed herein). In some embodiments, the composition may include at least about 20% by weight of a crystalline form of L-ornithine phenyl acetate (preferably at least about 50% by weight, and more preferably at least about 80% by weight). In some embodiments, the composition consists essentially of a crystalline form of L-ornithine phenyl acetate. In some embodiments, the composition includes a mixture of at least two (e.g., two, three or four forms) of Forms I, II, III, and V.

The compositions, in some embodiments, include Form II. For example, the compositions may include at least about 20%; at least about 50%; at least about 90%; at least about 95%; or at least about 99% of Form II. Similarly, the compositions may also include, for example, Forms I, III or V. The compositions may optionally include at least about 20%; at least about 50%; at least about 90%; at least about 95%; or at least about 99% of Forms I, II, III and/or V.

Also within the scope of the present application are amorphous forms of L-ornithine phenyl acetate. Various methods are known in the art for preparing amorphous forms. For example, a solution of L-ornithine phenyl acetate may be dried under vacuum by lyophilization to obtain an amorphous composition. See P.C.T. Application WO 2007/058634, which published in English and designates the U.S., and is hereby incorporated by reference for disclosing methods of lyophilization.

It is preferred that the composition have low amounts (if any) of alkali and halogen ions or salts, particular sodium and chloride. In some embodiments, the composition comprises no more than about 100 ppm of alkali metals (preferably no more than about 20 ppm, and most preferably no more than about 10 ppm). In some embodiments, the composition comprises no more than about 100 ppm of sodium (preferably no more than about 20 ppm, and most preferably no more than about 10 ppm). In some embodiments, the composition comprises no more than about 0.1% by weight of halides (preferably no more than about 0.01% by weight). In some embodiments, the composition comprises no more than about 0.1% by weight of chloride (preferably no more than about 0.01% by weight).

The reduced content of alkali metals and halides provides a composition suitable for preparing concentrated isotonic solutions. As such, these compositions can be more easily administered intravenously compared to, for example, administering mixtures of L-ornithine hydrochloride and sodium phenyl acetate. In some embodiments, an about 45 to about 55 mg/mL solution of L-ornithine phenyl acetate in water (preferably about 50 mg/mL) is isotonic with body fluids (e.g., the solution exhibits an osmolality in the range of about 280 to about 330 mOsm/kg).

The compositions may also include residual amounts of the anion from an intermediate salt formed during the process of making the L-ornithine phenyl acetate composition. For example, some of the processes disclosed herein yield compositions having benzoic acid or a salt thereof. In some embodiments, the composition comprises at least about 0.01% by weight benzoic acid or a salt thereof (preferably at least about 0.05% by weight, and more preferably about 0.1% by weight). In some embodiments, the composition comprises no more than about 3% by weight benzoic acid or a salt thereof (preferably no more than about 1% by weight, and more preferably no more than about 0.5% by weight). In some embodiments, the composition includes a salt, or an acid thereof, in the range of about 0.01% to about 3% by weight (preferably about 0.1% to about 1%), wherein the salt is selected from acetate, aspartate, formate, oxalate, bicarbonate, carbonate, bitrate, sulfate, nitrate, isonicotinate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate, pamoate (i.e., 1,1'-methylene-bis-(2-hydroxy-3-naphthoate) or phosphate.

Similarly, a composition prepared using an acetate intermediate may have residual amounts of acetic acid or acetate. In some embodiments, the composition includes at least about 0.01% by weight acetic acid or acetate (preferably at least about 0.05% by weight, and more preferably about 0.1% by weight). In some embodiments, the composition includes no more than about 3% by weight acetic acid or acetate (preferably no more than about 1% by weight, and more preferably no more than about 0.5% by weight).

The compositions may also include low amounts of silver. Exemplary processes disclosed herein utilize, for example, silver benzoate, but still yield compositions with surprisingly low amounts of silver. Thus, in some embodiments, the composition includes no more than about 600 ppm silver (preferably no more than about 100 ppm, and more preferably no more than about 65 ppm). In some embodiments, the composition includes at least about 10 ppm silver (alternatively at least about 20 or 25 ppm silver).

Pharmaceutical Compositions

The compositions of L-ornithine phenyl acetate of the present application may also be formulated for administration to a subject (e.g., a human). L-Ornithine phenyl acetate, and accordingly the compositions disclosed herein, may be formulated for administration with a pharmaceutically acceptable carrier or diluent. L-ornithine phenyl acetate may thus be formulated as a medicament with a standard pharmaceutically acceptable carrier(s) and/or excipient(s) as is routine in the pharmaceutical art. The exact nature of the formulation will depend upon several factors including the desired route of administration. Typically, L-ornithine phenyl acetate is formulated for oral, intravenous, intragastric, subcutaneous, intravascular or intraperitoneal administration.

The pharmaceutical carrier or diluent may be, for example, water or an isotonic solution, such as 5% dextrose in water or normal saline. Solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, gum arabic, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manners, for example, by means of mixing, granulating, tabletting, sugar-coating, or film-coating processes.

Liquid dispersions for oral administration may be syrups, emulsions or suspensions. The syrups may contain as carriers, for example, saccharose or saccharose with glycerine and/or mannitol and/or sorbitol.

Suspensions and emulsions may contain a carrier, for example a natural gum, agar, sodium alginate, pectin, methylcellulose, carboxymethylcellulose, or polyvinyl alcohol. The suspensions or solutions for intramuscular injections may contain, together with L-ornithine phenyl acetate, a pharmaceutically acceptable carrier, e.g. sterile water, olive oil, ethyl oleate, glycols, e.g. propylene glycol, and if desired, a suitable amount of lidocaine hydrochloride.

The medicament may consist essentially of L-ornithine phenyl acetate and a pharmaceutically acceptable carrier. Such a medicament therefore contains substantially no other amino acids in addition to L-ornithine and phenyl acetate. Furthermore, such a medicament contains insubstantial amounts of other salts in addition to L-ornithine phenyl acetate.

Oral formulations may generally include dosages of L-ornithine phenyl acetate in the range of about 500 mg to about 100 g. Accordingly, in some embodiments, the oral formulation includes the L-ornithine phenyl acetate compositions disclosed herein in the range of about 500 mg to about 50 g. In some embodiments, the oral formulation is substantially free of alkali metal salts and halides (e.g., contains no more than trace amounts of alkali metal salts and halides).

Intravenous formulations may also generally include dosages of L-ornithine phenyl acetate in the range of about 500 mg to about 100 g (preferably about 1 g to about 50 g). In some embodiments, the intravenous formulation is substantially free of alkali metal salts and halides (e.g., contains no more than trace amounts of alkali metal salts and halides). In some embodiments, the intravenous formulation has a concentration of about 5 to about 300 mg/mL of L-ornithine phenyl acetate (preferably about 25 to about 200 mg/mL, and more preferably about 40 to about 60 mg/mL).

The composition, or medicament containing said composition, may optionally be placed is sealed packaging. The sealed packaging may reduce or prevent moisture and/or ambient air from contacting the composition or medicament. In some embodiments, the packaging includes a hermetic seal. In some embodiments, the packaging sealed under vacuum or with an inert gas (e.g., argon) within the sealed package. Accordingly, the packaging can inhibit or reduce the rate of degradation for the composition or medicament stored within the packaging. Various types of sealed packaging are known in the art. For example, U.S. Pat. No. 5,560,490, is hereby incorporate by reference in its entirety, discloses an exemplary sealed package for medicaments.

Compositions with Improved Density

Applicants have surprisingly found that compositions with greater density may be obtained by applying sufficient pressure to compositions having Form I (described below) to induce a transition to Form II (described below). For example, applying 3 tons of force for 90 minutes to Forms I and II yield densities of 1.197 kg/m$^3$ and 1.001 kg/m$^3$, respectively. Surprisingly, Form I converted to Form II under these conditions; therefore the greater density appears to be explained by the different crystalline form as the starting material.

Accordingly, disclosed herein are methods of increasing the density of an L-ornithine phenyl acetate composition having Form I by applying pressure to the composition sufficient to induce a transition to Form II. The appropriate amount of force or pressure to induce the phase change may vary with the amount of time the force or pressure is applied. Thus, a person of ordinary skill, guided by the teachings of the present application, can determine appropriate amounts of pressure and time to induce the phase change. In some embodiments, at least about 1 ton of force is applied (preferably at least about 2 tons, and more preferably about 3 tons). In some embodiments, at least about 500 psi of pressure is applied (preferably at least about 1000 psi, and more preferably at least about 2000 psi).

The amount of time for applying pressure is not particularly limited, and as discussed above, will vary depending upon the amount time. For example, when applying large forces (e.g., 10 tons) to a typical tablet-sized punch, the time may be about 1 second or less. In some embodiments, the time for apply pressure is a predetermined time. The time may be, for example, about 0.1 seconds; about 1 second; at least about 1 minute; at least about 5 minutes; or at least about 20 minutes.

In some embodiments, the composition includes at least about 10% by weight of Form I. In some embodiments, the composition includes at least about 30% by weight of Form I.

Without being bound to any particular theory, Applicants believe the greater density may result, at least in part, from ethanol solvate component present in Form I. Applying pressure to the solvate may facilitate forming a denser structure with fewer defects (e.g., grain boundaries). Consequently, in some embodiments, methods of increasing the density of an L-ornithine phenyl acetate composition having solvate components include applying pressure to the composition sufficient to induce a transition to Form II. In some embodiments, the pressure is at least about 500 psi (preferably at least about 1000 psi, and more preferably at least about 2000 psi). In some embodiments, the time for apply pressure is a predetermined time. In some embodiments, the composition includes at least about 10% of the solvate form (preferably at least about 30%, and more preferably at least about 50%).

The compositions of L-ornithine phenyl acetate disclosed herein may therefore have higher densities compared to compositions obtain by, for example, precipitating a crystalline form. In some embodiments, the composition has a density of at least about 1.1 kg/m$^3$ (preferably at least about 1.15 kg/m$^3$, and more preferably at least about 1.18 kg/m$^3$). In some embodiments, the composition has a density of no more than about 1.3 kg/m$^3$ (preferably no more than about 1.25 kg/m$^3$, and more preferably no more than about 1.22 kg/m$^3$). In some embodiments, the composition has a density of about 1.2 kg/m$^3$.

Crystalline Forms of L-Ornithine Phenyl Acetate

Also disclosed herein are crystalline forms of L-ornithine phenyl acetate, and in particular, crystalline Form I, Form II, Form III, and Form V. L-Ornithine phenyl acetate may, in some embodiments, be obtained using the processes disclosed above and then crystallized using any of the methods disclosed herein.

Form I

The precise conditions for forming crystalline Form I may be empirically determined and it is only possible to give a number of methods which have been found to be suitable in practice.

Thus, for example, crystalline Form I may generally be obtained by crystallizing L-ornithine phenyl acetate under controlled conditions. As an example, precipitating L-ornithine phenyl acetate from a saturated solution by adding ethanol at reduced temperatures (e.g., 4° or −21° C.). Exemplary solvents for the solution that yield crystalline Form I upon adding ethanol include, but are not limited to, cyclohexanone, 1-propanol, diemthylcarbonate, N-methylpyrrolidine (NMP), diethyl ether, 2-butanol, cumene, ethyl formate, isobutyl acetate, 3-nethyl-1-butanol, and anisole.

Accordingly, in the context of the processes for making L-ornithine phenyl acetate disclosed above, the process can yield Form I by utilizing particular isolation methods. For example, L-ornithine phenyl acetate may be isolated by adding ethanol at reduced temperature to yield Form I.

Crystalline Form I was characterized using various techniques which are described in further detail in the experimental methods section. FIG. 1 shows the crystalline structure of Form I as determined by X-ray powder diffraction (XRPD). Form I, which may be obtained by the methods disclosed above, exhibits characteristic peaks at approximately 4.9°, 13.2°, 17.4°, 20.8° and 24.4° 2θ. Thus, in some embodiments, a crystalline form of L-ornithine phenyl acetate has one or more characteristic peaks (e.g., one, two, three, four or five characteristic peaks) selected from approximately 4.9°, 13.2°, 17.4°, 20.8°, and 24.4° 2θ.

As is well understood in the art, because of the experimental variability when X-ray diffraction patterns are measured on different instruments, the peak positions are assumed to be equal if the two theta (2θ) values agree to within 0.2° (i.e., ±0.2°). For example, the United States Pharmacopeia states that if the angular setting of the 10 strongest diffraction peaks agree to within ±0.2° with that of a reference material, and the relative intensities of the peaks do not vary by more than 20%, the identity is confirmed. Accordingly, peak positions within 0.2° of the positions recited herein are assumed to be identical.

Figure 2:
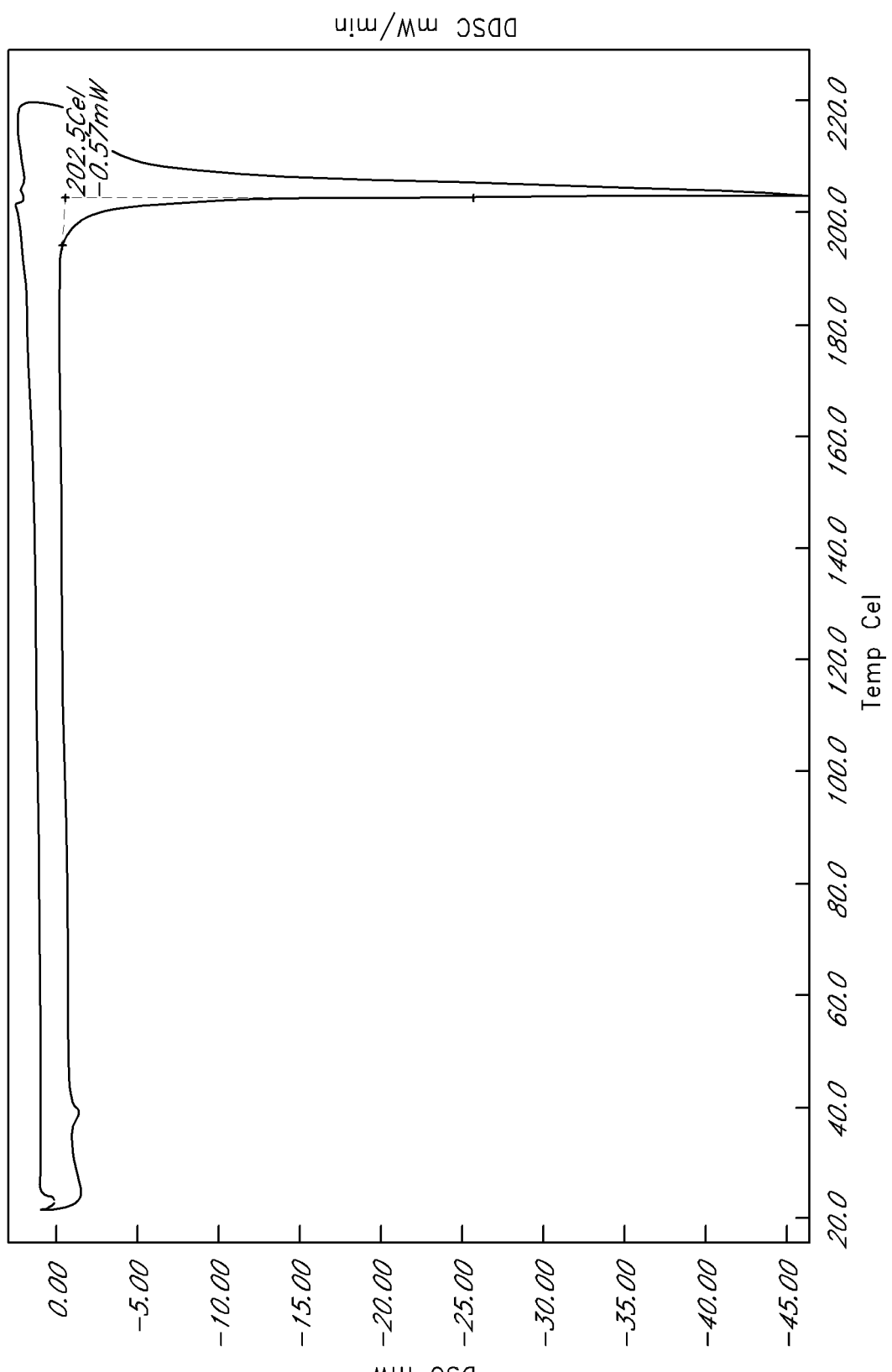
FIG. 2 shows differential scanning calorimetry results for Form I.
Figure 3:
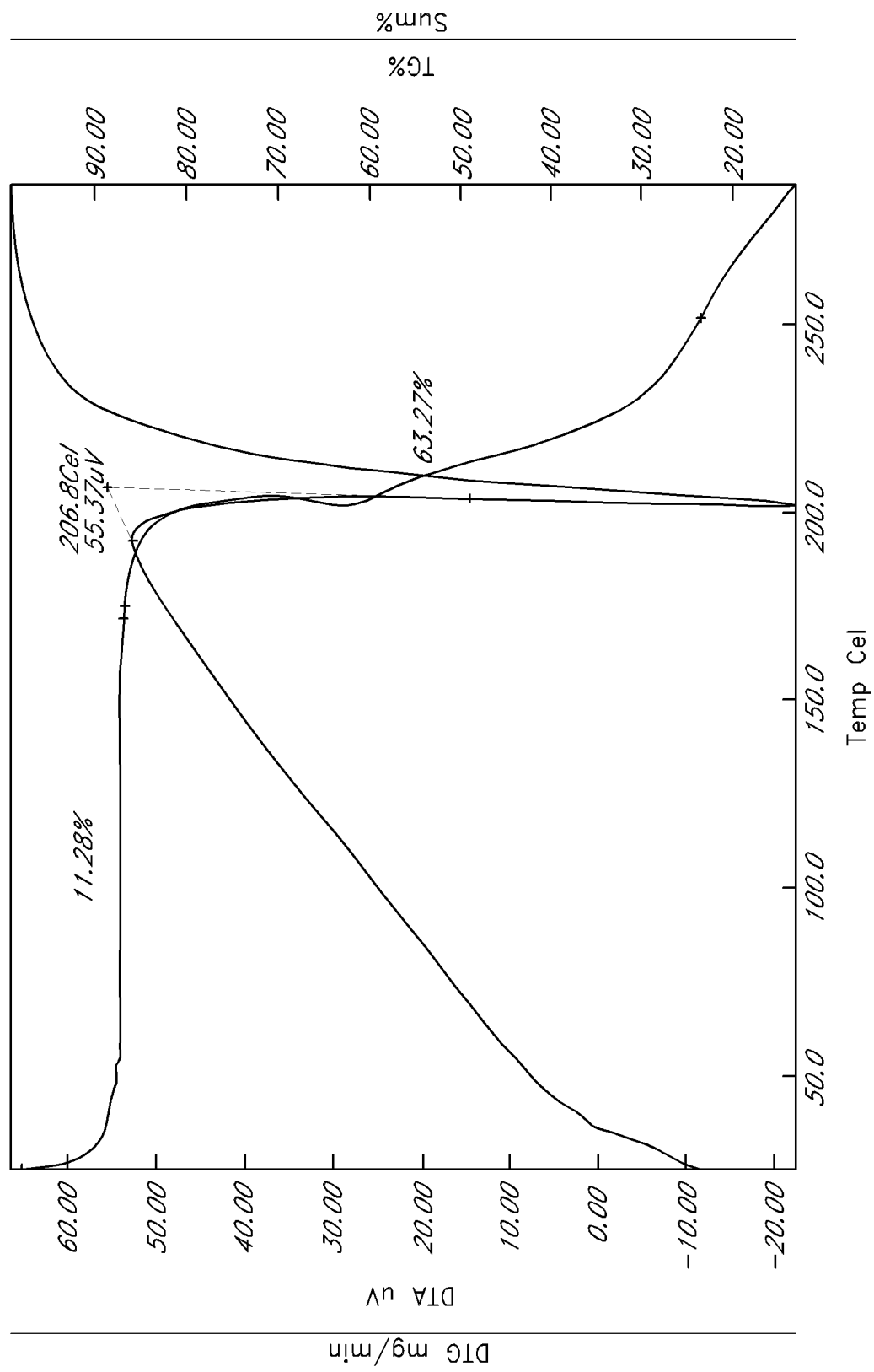
FIG. 3 shows thermogravimetric gravimetric/differential thermal analysis of Form I.

FIG. 2 shows results obtained by differential scanning calorimetry (DSC) for Form I. These results indicate an endotherm at 35° C., which is possibly associated with a desolvation and/or dehydration to Form II. A second transition at about 203° C. indicates the melting point for the crystal. To explore the possible existence of a desolvation and/or dehydration transition, Form I was analyzed by thermogravimetric gravimetric/differential thermal analysis (TG/DTA), which is shown in FIG. 3. Form I exhibits a 11.28% weight loss at about 35° C., and therefore these results further suggest that Form I exhibits a desolvation and/or dehydration transition at about 35° C. The melting point of about 203° C. could also be observed by TGA testing. Accordingly, in some embodiments, the crystalline form of L-ornithine phenyl acetate is characterized by differential scanning calorimetry as having an endotherm at about at about 35° C. In some embodiments, a crystalline form of L-ornithine phenyl acetate exhibits a weight loss of about 11% at about 35° C., as determined by TGA. In some embodiments, a crystalline form of L-ornithine phenyl acetate exhibits a melting point of about 203° C.

Figure 4:
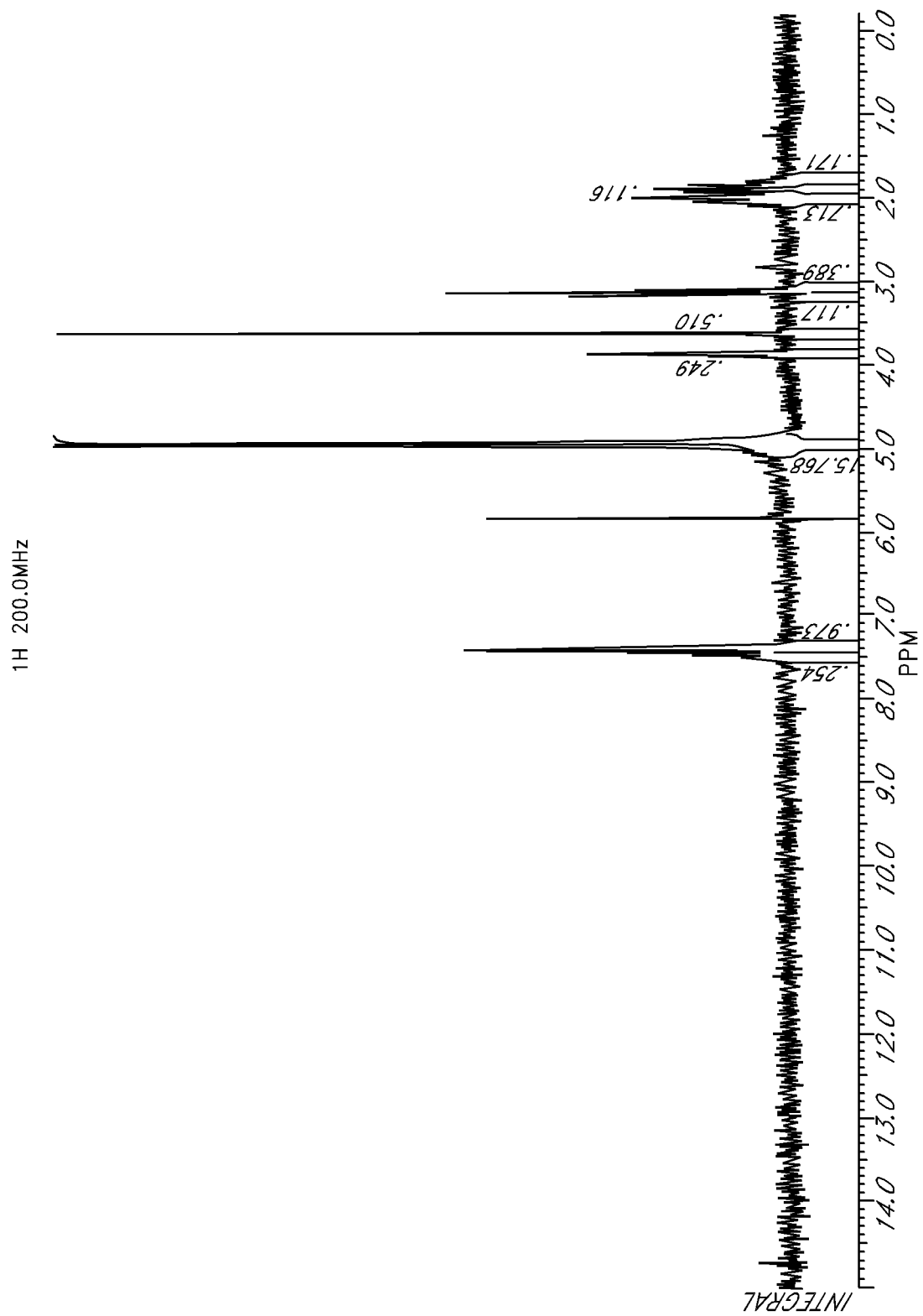
FIG. 4 shows the $^1$H nuclear magnetic resonance spectrum obtained from a sample of Form I.
Figure 5:
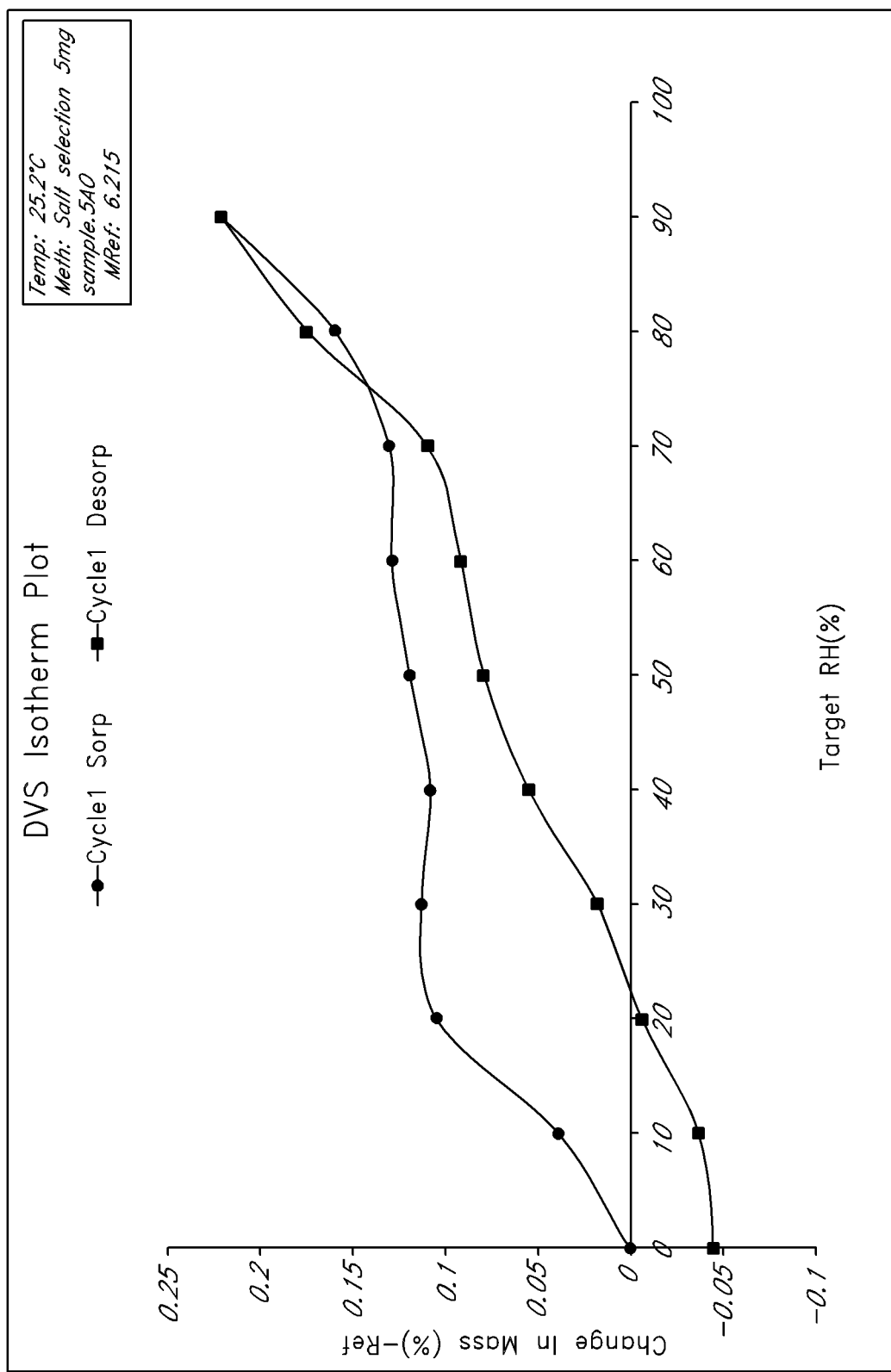
FIG. 5 shows dynamic vapor sorption results for Form I.

FIG. 4 shows nuclear magnetic resonance (NMR) integrals and chemical shifts for Form I. The integrals confirm the presence of L-ornithine phenyl acetate: 7.5 (aromatic CH), 3.8 (CH adjacent to $NH_2$), 3.6 ($CH_2$ unit of phenyl acetate), 3.15 ($CH_2$ adjacent to $NH_2$) and 1.9 (aliphatic $CH_2$ units) ppm (integrals: 5:1:2:2:4 protons; 1.2, 0.25, 0.5, 0.5, 1.0). Amine protons and hydroxyl protons were not observed due to proton exchange at both the zwitterion and site of salt formation. Meanwhile, FIG. 5 shows dynamic vapor sorption (DVS) results for Form I, and show a water uptake of about 0.2% by weight. XRPD results following DVA analysis (not shown) confirm that Form I did not transition to a different polymorph. Form I can therefore be characterized as non-hygroscopic and stable over a wide range of humidity.

A 7-day stability study of Form I at 40° C./75% RH indicated that a transformation to Form II occurred under these conditions. Form I also converts to Form II at elevated temperatures (e.g., 80° or 120° C.), with or without applying a vacuum, after 7 or 14 days. Accordingly, Form I is metastable.

Single crystal x-ray diffraction (SXRD) was also used to determine the structure of Form I at −20° and −123° C., and the results are summarized in TABLES 1 and 2. The results confirm that Form I is a solvate having ethanol and water molecules within the unit cell. In some embodiments, a crystalline form of L-ornithine phenyl acetate can be represented by the formula $C_{15}H_{28}N_2O_6$. In some embodiments, a crystalline form of L-ornithine phenyl acetate can be represented by the formula $[C_5H_{13}N_2O_2][C_8H_7O_2]$ $EtOH \cdot H_2O$. In some embodiments, a crystalline form of L-ornithine phenyl acetate exhibits a single crystal X-ray crystallographic analysis with crystal parameters approximately equal to the following: unit cell dimensions of a=5.3652(4) Å, b=7.7136(6) Å, c=20.9602(18) Å, α=90°, β=94.986(6)°, γ=90°; a monoclinic crystal system, and a $P2_1$ space group.

TABLE 1

Crystallographic Data of Form I Collected at −20° C.

| | |
|---|---|
| Empirical Formula | $C_{15}H_{28}N_2O_6$ or |
| | $[C_5H_{13}N_2O_2][C_8H_7O_2]EtOH \cdot H_2O$ |
| Formula Weight | 332.39 |
| Crystal System | Monoclinic |
| Space Group | $P2_1$ |
| Unit Cell Dimensions | a = 5.3652(4) Å α = 90° |
| | b = 7.7136(6) Å β = 94.986(6)° |
| | c = 20.9602(18) Å γ = 90° |
| Volume | 864.16(12) Å$^3$ |
| Number of Reflections | 1516 (2.5° < θ < 28°) |
| Density (calculated) | 1.277 mg/cm$^3$ |

TABLE 2

Crystallographic Data of Form I Collected at −123° C.

| | |
|---|---|
| Empirical Formula | $C_{15}H_{28}N_2O_6$ or |
| | $[C_5H_{13}N_2O_2][C_8H_7O_2]EtOH \cdot H_2O$ |
| Formula Weight | 332.39 |
| Crystal System | Monoclinic |
| Space Group | $P2_1$ |
| Unit Cell Dimensions | a = 5.3840(9) Å α = 90° |
| | b = 7.7460(12) Å β = 95.050(12)° |
| | c = 21.104(4) Å γ = 90° |
| Volume | 876.7(3) Å$^3$ |
| Number of Reflections | 1477 (2.5° < θ < 18°) |
| Density (calculated) | 1.259 mg/cm$^3$ |

Form II

The precise conditions for forming crystalline Form II may be empirically determined and it is only possible to give a number of methods which have been found to be suitable in practice.

Thus, for example, crystalline Form II may be prepared by crystallization under controlled conditions. Crystalline Form II can be prepared by, for example, evaporating a saturated organic solution of L-ornithine phenyl acetate. Non-limiting examples of organic solutions that may be used to obtain Form II include ethanol, acetone, benzonitrile, dichloromethane (DCM), dimethyl sulfoxide (DMSO), ethyl acetate (EtOAc), acetonitrile (MeCN), methyl acetate (MeOAc), nitromethane, tert-butyl methyl ether (TBME), tetrahydrofuran, and toluene. Other solvents may yield a mixture of Form I and II, such as, but not limited to, 1,4 dioxane, 1-butanol, cyclohexane, IPA, THF, MEK, MeOAc and water.

Form II can also be obtained by precipitating L-ornithine phenyl acetate from a saturated organic solution by adding an anti-solvent for L-ornithine phenyl acetate, such as IPA. Form II may be precipitated over a broad range of temperatures (e.g., room temperature, 4° C., and −21° C.). Non-limiting examples of suitable solvents for the saturated organic solution include cyclohexanone, 1-propanol, dimethyl carbonate, N-methylpyrrolidone (NMP), diisopropyl ether, diethyl ether, ethylene glycol, dimethylformamide (DMF), 2-butanol, cumene, isobutyl acetate, 3-methyl-1-butanol, and anisole. Alternatively, the same listed solvents (e.g., cyclohexanone) can be used to form a solution of L-ornithine phenyl acetate, and Form II may be precipitated by adding ethanol at ambient conditions. As another example, Form II may also be obtained by forming a slurry of L-ornithine phenyl acetate with the listed organic solvents and cycling the temperature between 25° and 40° C. every 4 hours for about 18 cycles (or 72 hours).

Accordingly, in the context of the processes for making L-ornithine phenyl acetate disclosed above, the process can yield Form II by utilizing particular isolation methods. For example, L-ornithine phenyl acetate may be isolated by adding IPA, or evaporating the organic solvent, to yield Form II.

Figure 6:
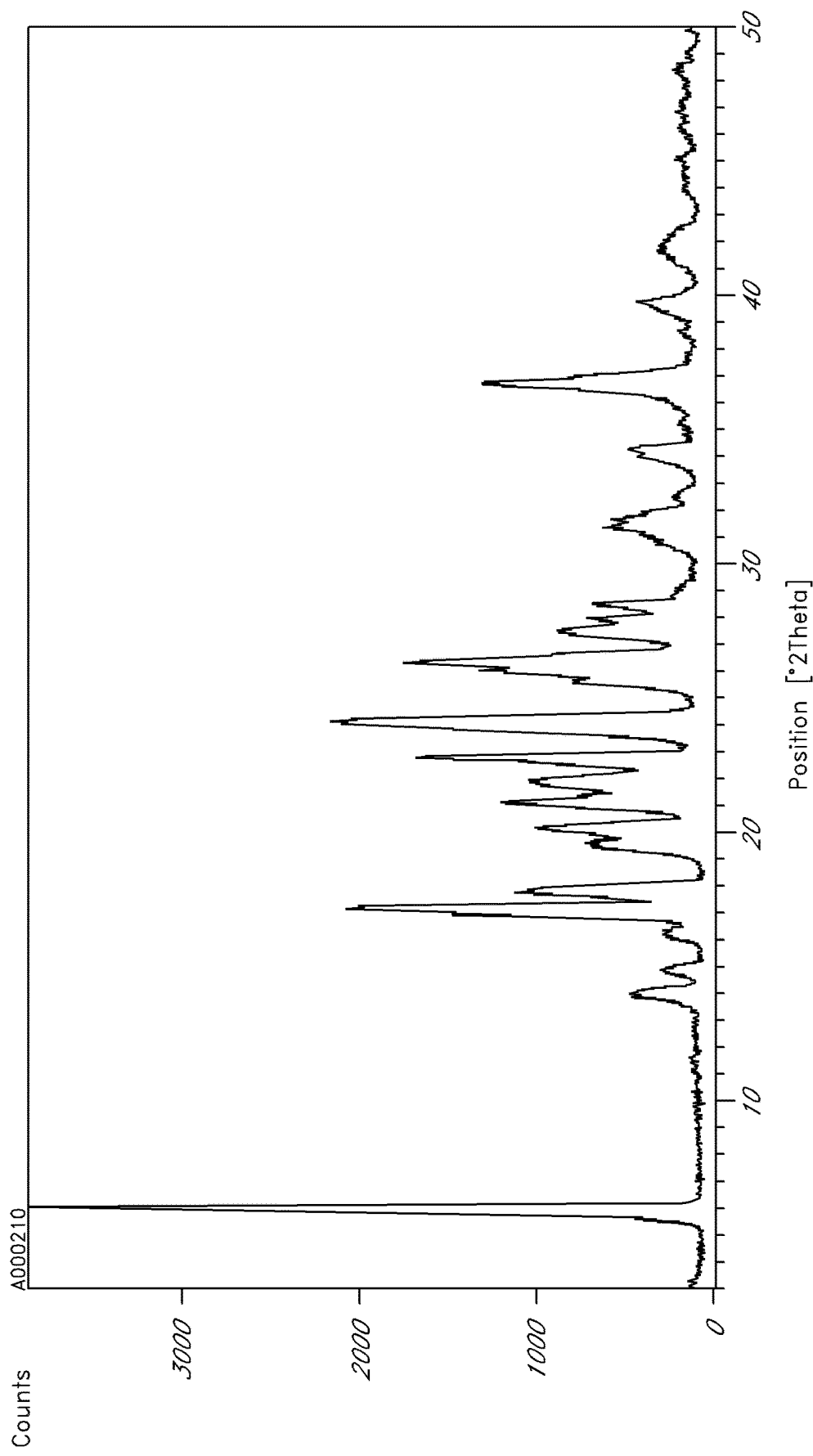
FIG. 6 is an X-ray powder diffraction pattern of Form II.

FIG. 6 shows the crystalline structure of Form II as determined by XRPD. Form II, which may be obtained by the methods disclosed above, exhibits characteristic peaks at approximately 6.0°, 13.9°, 14.8°, 17.1°, 17.8° and 24.1° 2θ. Thus, in some embodiments, a crystalline form of L-ornithine phenyl acetate has one or more characteristic peaks (e.g., one, two, three, four, five or six characteristic peaks) selected from approximately 6.0°, 13.9°, 14.8°, 17.1°, 17.8° and 24.12° θ.

Figure 7:
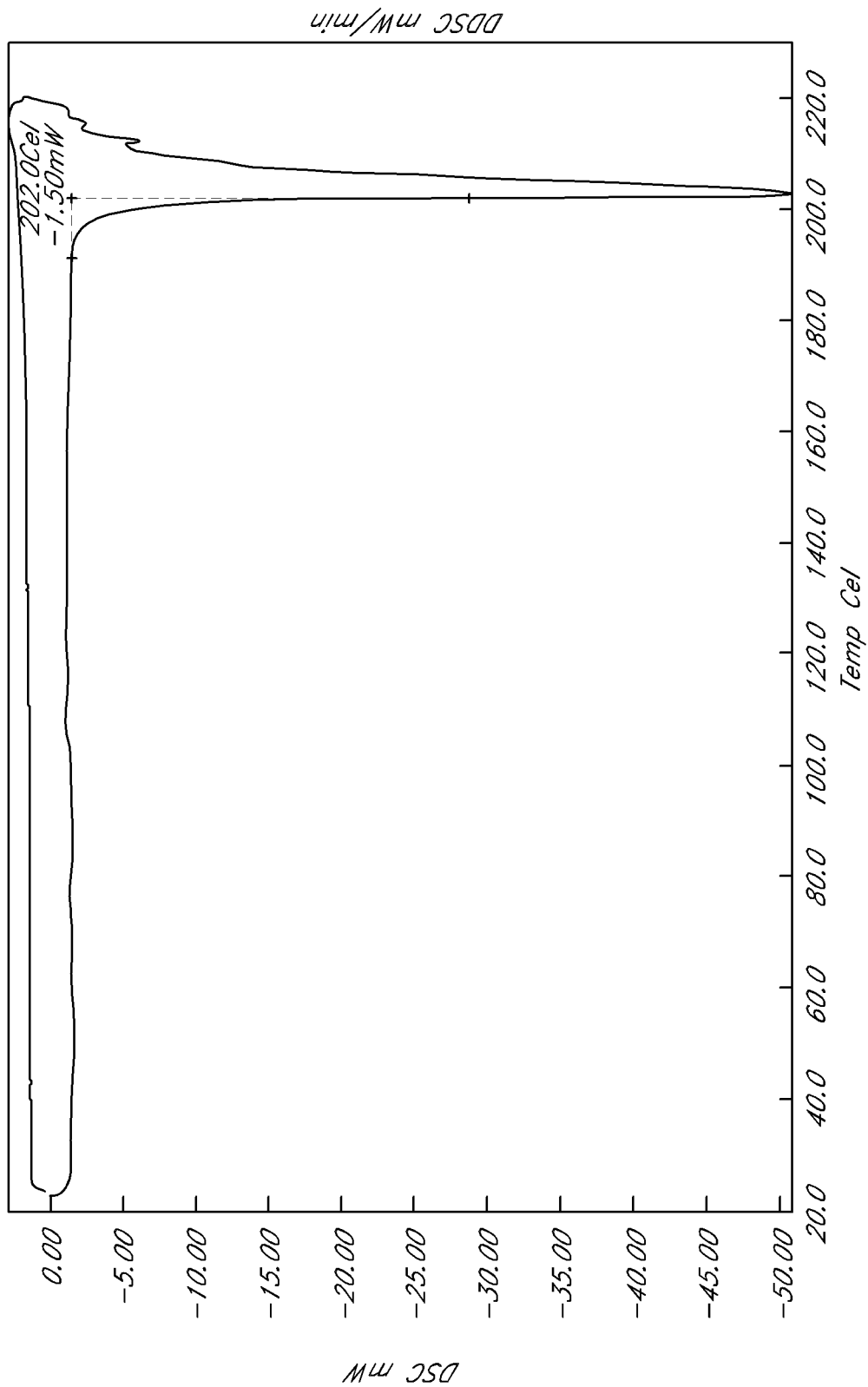
FIG. 7 shows differential scanning calorimetry results for Form II.
Figure 8:
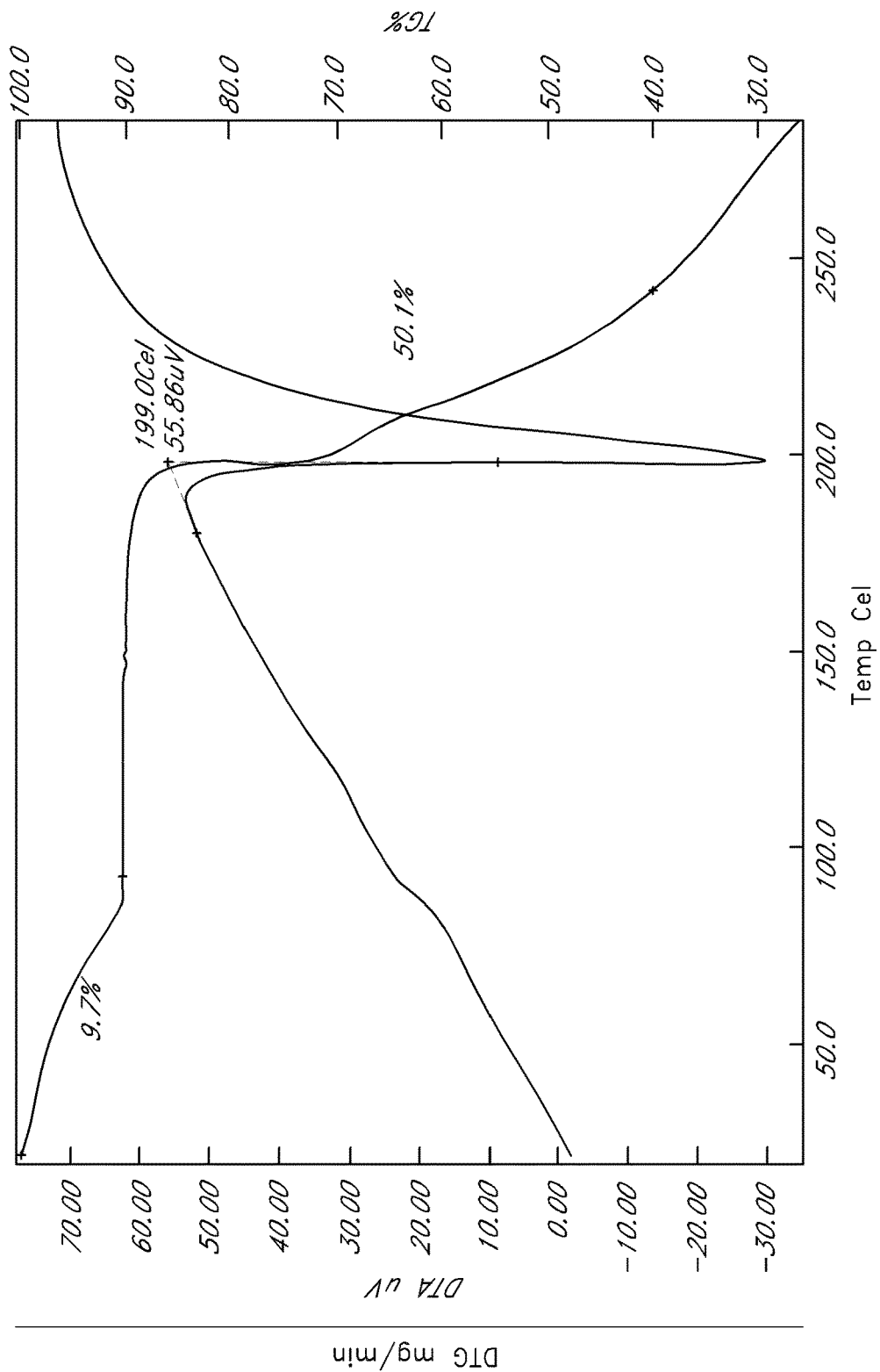
FIG. 8 shows thermogravimetric gravimetric/differential thermal analysis of Form II.

FIG. 7 shows results obtained by differential scanning calorimetry (DSC) for Form II. These results indicate a melting point of about 202° C., which is approximately the same as the melting point for Form I. This suggests that Form I transitions to Form II upon heating above about 35° C. Form II was also analyzed using TG/DTA, as shown in FIG. 8, and exhibits an about 9.7% weight loss associated with residual solvent. The melting point of about 202° C. could also be observed by TGA testing. Accordingly, in some embodiments, a crystalline form of L-ornithine phenyl acetate exhibits a melting point of about 202° C.

A 7-day stability study of Form II at 40° C./75% RH failed to produce an observable phase change. In fact, Form II was stable over 14 days when exposed to elevated temperatures, varying pHs, UV light or oxygen. Accordingly, Form II is considered stable.

Figure 9:
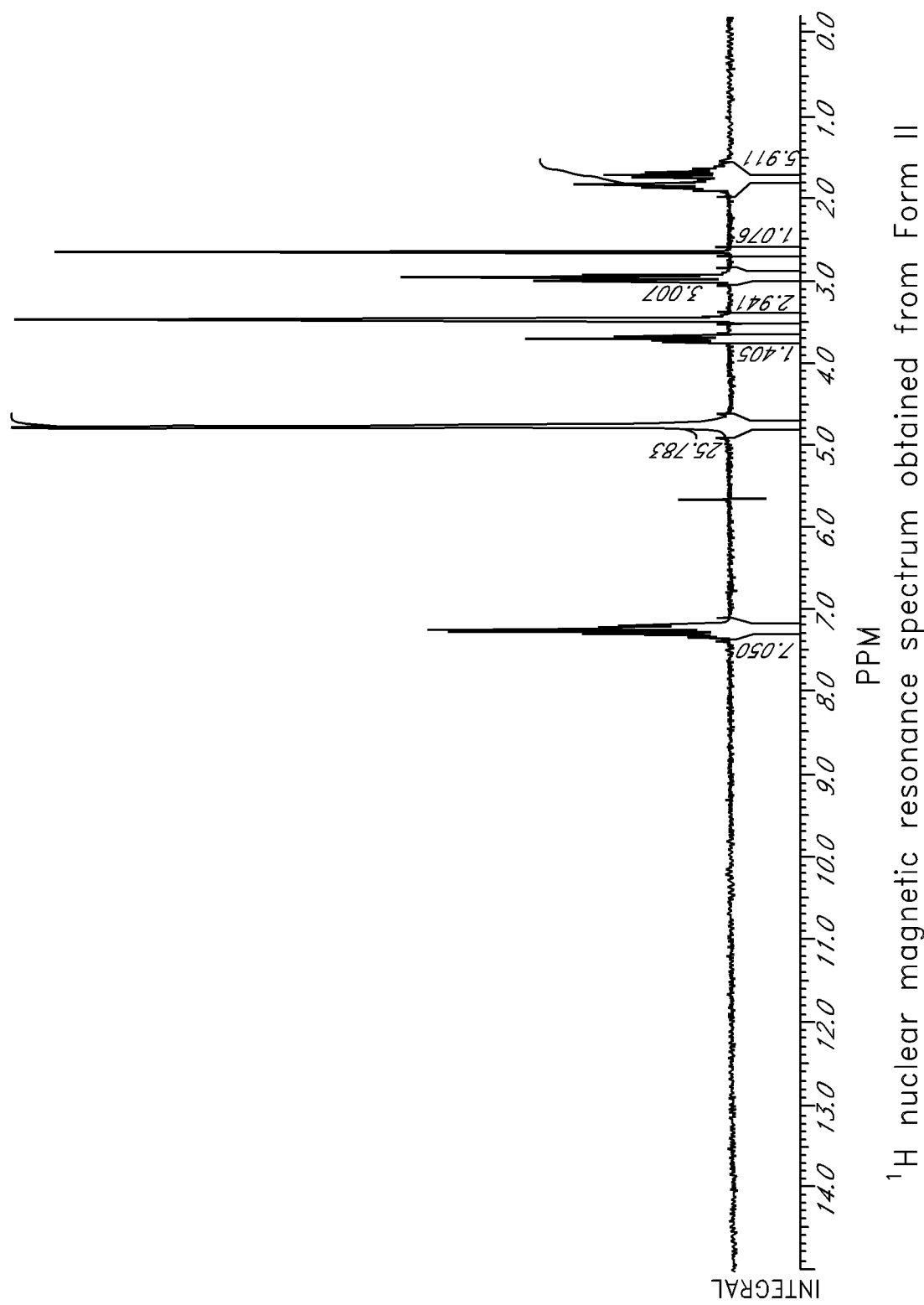
FIG. 9 shows the $^1$H nuclear magnetic resonance spectrum obtained from a sample of Form II.
Figure 10:
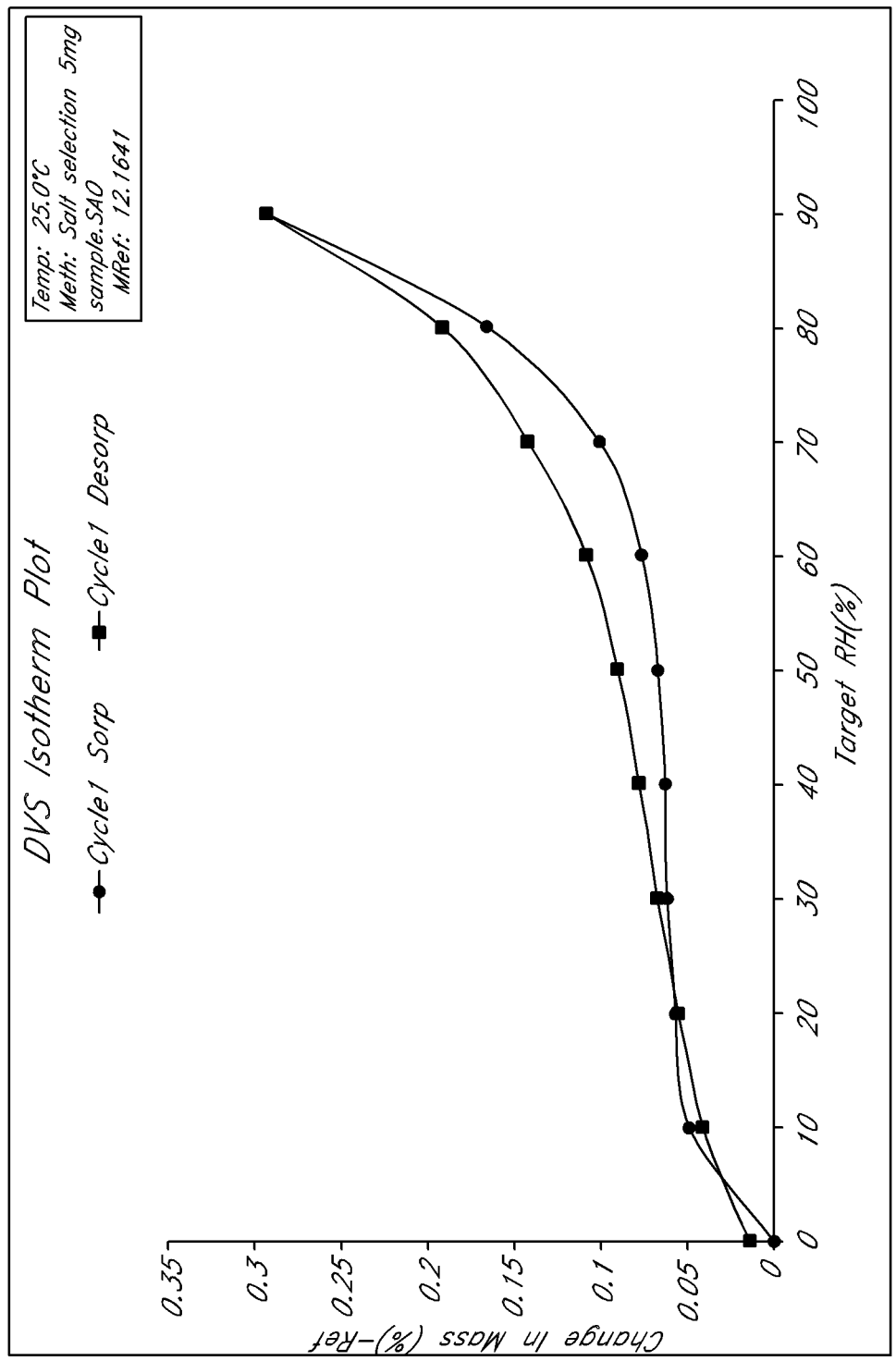
FIG. 10 shows dynamic vapor sorption results for Form II.

FIG. 9 shows nuclear magnetic resonance (NMR) integrals and chemical shifts for Form II. The integrals confirm the presence of L-ornithine phenyl acetate: 7.5 (aromatic CH), 3.8 (CH adjacent to NH2), 3.6 (CH2 unit of phenylacetate), 3.15 (CH2 adjacent to NH2) and 1.9 (aliphatic CH2 units) ppm (integrals: 5:1:2:2:4 protons; 7.0, 1.4, 2.9, 3.0, 5.9). Amine protons and hydroxyl protons were not observed due to proton exchange at both the zwitterion and site of salt formation. Meanwhile, FIG. 10 shows dynamic vapor sorption (DVS) results for Form II, and show a water uptake of about 0.3% by weight. XRPD results following DVA analysis (not shown) confirm that Form II did not transition to a different polymorph. Form II can therefore be characterized as non-hygroscopic and stable over a wide range of humidity.

Single crystal x-ray diffraction (SXRD) was also used to determine the structure of Form II at 23° and −123° C., and the results are summarized in TABLES 3 and 4. The results demonstrate that Form II is anhydrous and therefore structurally different from Form I. In some embodiments, a crystalline form of L-ornithine phenyl acetate can be represented by the formula $C_{13}H_{20}N_2O_4$. In some embodiments, a crystalline form of L-ornithine phenyl acetate can be represented by the formula $[C_5H_{13}N_2O_2][C_8H_7O_2]$. In some embodiments, a crystalline form of L-ornithine phenyl acetate exhibits a single crystal X-ray crystallographic analysis with crystal parameters approximately equal to the following: unit cell dimensions of a=6.594(2) Å, α=90°, b=6.5448(18) Å, β=91.12(3)°, c=31.632(8) Å, γ=90°; a monoclinic crystal system; and a $P2_1$ space group.

TABLE 3

Crystallographic Data of Form II Collected at 23° C.

| | |
|---|---|
| Empirical Formula | $C_{13}H_{20}N_2O_4$ or $[C_5H_{13}N_2O_2][C_8H_7O_2]$ |
| Formula Weight | 268.31 |
| Crystal System | Monoclinic |
| Space Group | $P2_1$ |
| Unit Cell Dimensions | a = 6.594(2) Å α = 90° |
| | b = 6.5448(18) Å β = 91.12(3)° |
| | c = 31.632(8) Å γ = 90° |
| Volume | 1364.9(7) Å$^3$ |
| Number of Reflections | 3890 (3° < θ < 20.5°) |
| Density (calculated) | 1.306 mg/cm$^3$ |

TABLE 4

Crystallographic Data of Form II Collected at −123° C.

| | |
|---|---|
| Empirical Formula | $C_{15}H_{28}N_2O_6$ or $[C_5H_{13}N_2O_2][C_8H_7O_2]$ |
| Formula Weight | 332.39 |
| Crystal System | Monoclinic |
| Space Group | $P2_1$ |
| Unit Cell Dimensions | a = 5.3652(4) Å α = 90° |
| | b = 7.7136(6) Å β = 94.986(6)° |
| | c = 20.9602(18) Å γ = 90° |
| Volume | 864.16(12) Å$^3$ |
| Number of Reflections | 1516 (2.5° < θ < 28°) |
| Density (calculated) | 1.277 mg/cm$^3$ |

Form III

The precise conditions for forming crystalline Form III may be empirically determined and it is only possible to give a number of methods which have been found to be suitable in practice.

Thus, for example, Form III may be obtained by placing a saturated solution of L-ornithine phenyl acetate in a cooled temperature environment of about −21° C., where the solution is a mixture of acetone and water (e.g., equal parts volume of acetone and water). As another example, adding IPA to a saturated solution of L-ornithine phenyl acetate in 2-butanol can yield Form III when completed at ambient conditions. Furthermore, Form III may be obtained, for example, by adding IPA to a saturated solution of L-ornithine phenyl acetate in isobutyl acetate when completed at reduced temperatures of about −21° C.

Accordingly, in the context of the processes for making L-ornithine phenyl acetate disclosed above, the process can yield Form III by utilizing particular solvents and isolation methods. For example, L-ornithine phenyl acetate may be formed within a mixture of acetone and water, and subsequently placed in a cool environment of about −21° C. to yield Form III.

Figure 11:
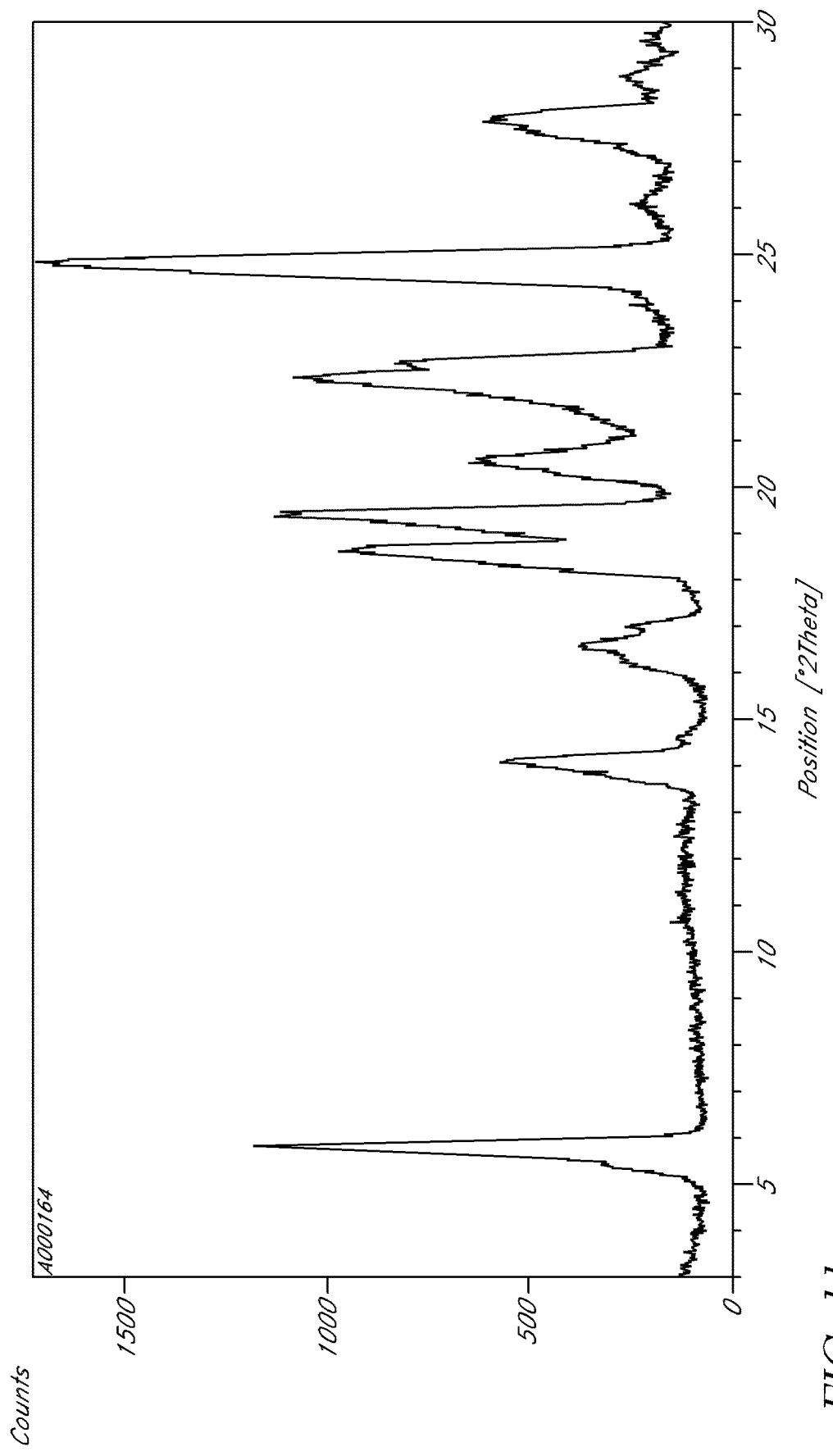
FIG. 11 is an X-ray powder diffraction pattern of Form III.

FIG. 11 shows the crystalline structure of Form III as determined by XRPD. Form III, which may be obtained by the methods disclosed above, exhibits characteristic peaks at approximately 5.8°, 14.1°, 18.6°, 19.4°, 22.3° and 24.8° 2θ. Thus, in some embodiments, a crystalline form of L-ornithine phenyl acetate has one or more characteristic peaks (e.g., one, two, three, four, five or six characteristic peaks) selected from approximately 5.8°, 14.1°, 18.6°, 19.4°, 22.3° and 24.8° 2θ.

Figure 12:
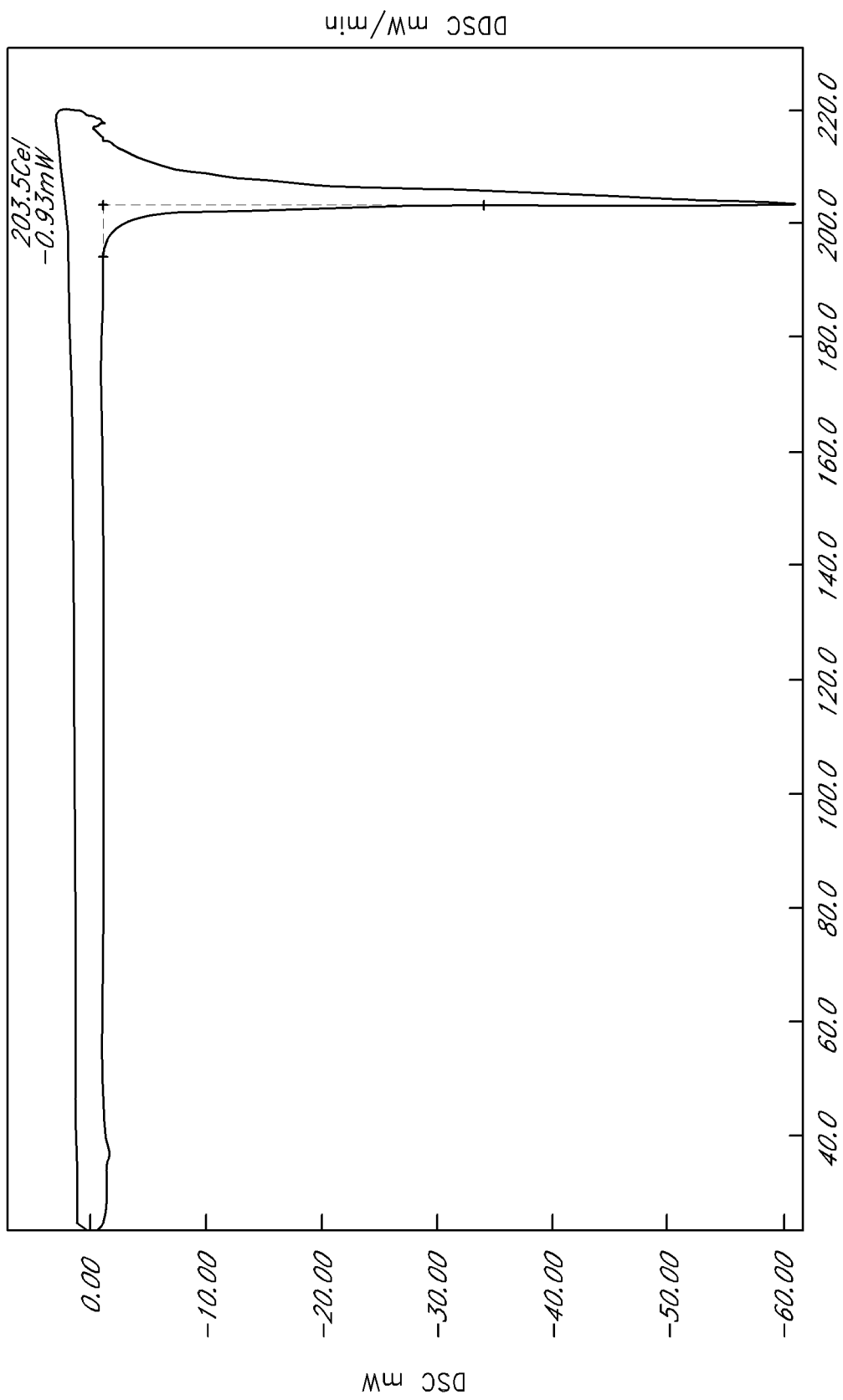
FIG. 12 shows differential scanning calorimetry results for Form III.
Figure 13:
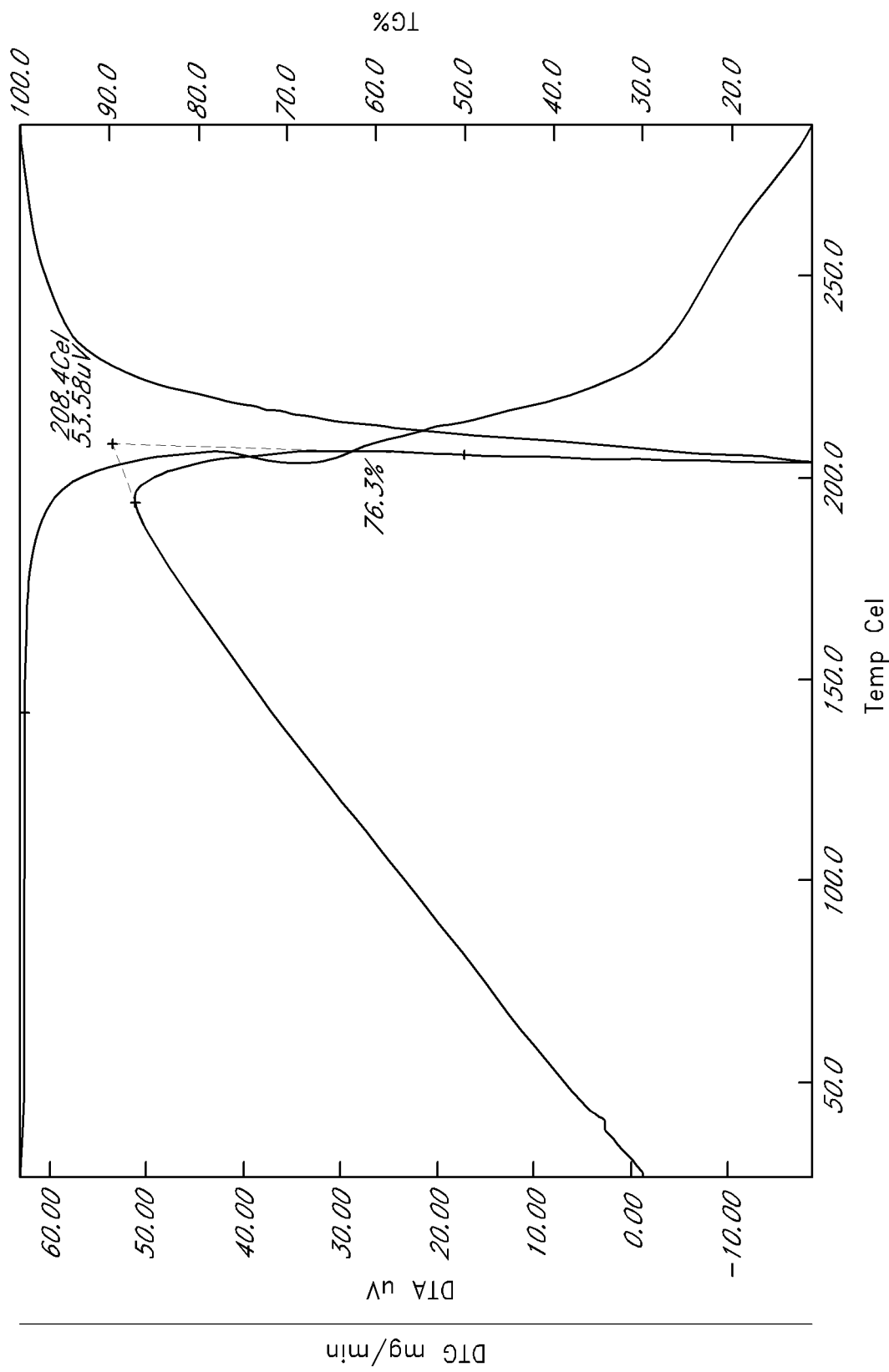
FIG. 13 shows thermogravimetric gravimetric/differential thermal analysis of Form III.

FIG. 12 shows results obtained by differential scanning calorimetry (DSC) for Form III. These results indicate a melting point of about 203° C., which is approximately the same as the melting points for Form I and Form II. Additionally, Form III exhibits an endotherm at about 40° C. Form III was also analyzed using TG/DTA, as shown in FIG. 13, and exhibits no significant weight loss before the melting point. Form III may therefore be characterized as anhydrous. The melting point of about 203° C. could also be observed by TGA testing. Accordingly, in some embodiments, a crystalline form of L-ornithine phenyl acetate exhibits a melting point of about 203° C. In some embodiments, a crystalline form of L-ornithine phenyl acetate is characterized by differential scanning calorimetry as having an endotherm at about 40° C. In some embodiments, a crystalline form of L-ornithine phenyl acetate is anhydrous.

A 7-day stability study of Form III at 40° C./75% RH indicated that a transformation to Form II occurred under these conditions. In contrast, Form II is stable at elevated temperatures, with or without vacuum, for periods of 7 or 10 days. Accordingly, Form III is most likely metastable, but more stable than Form I.

Figure 14:
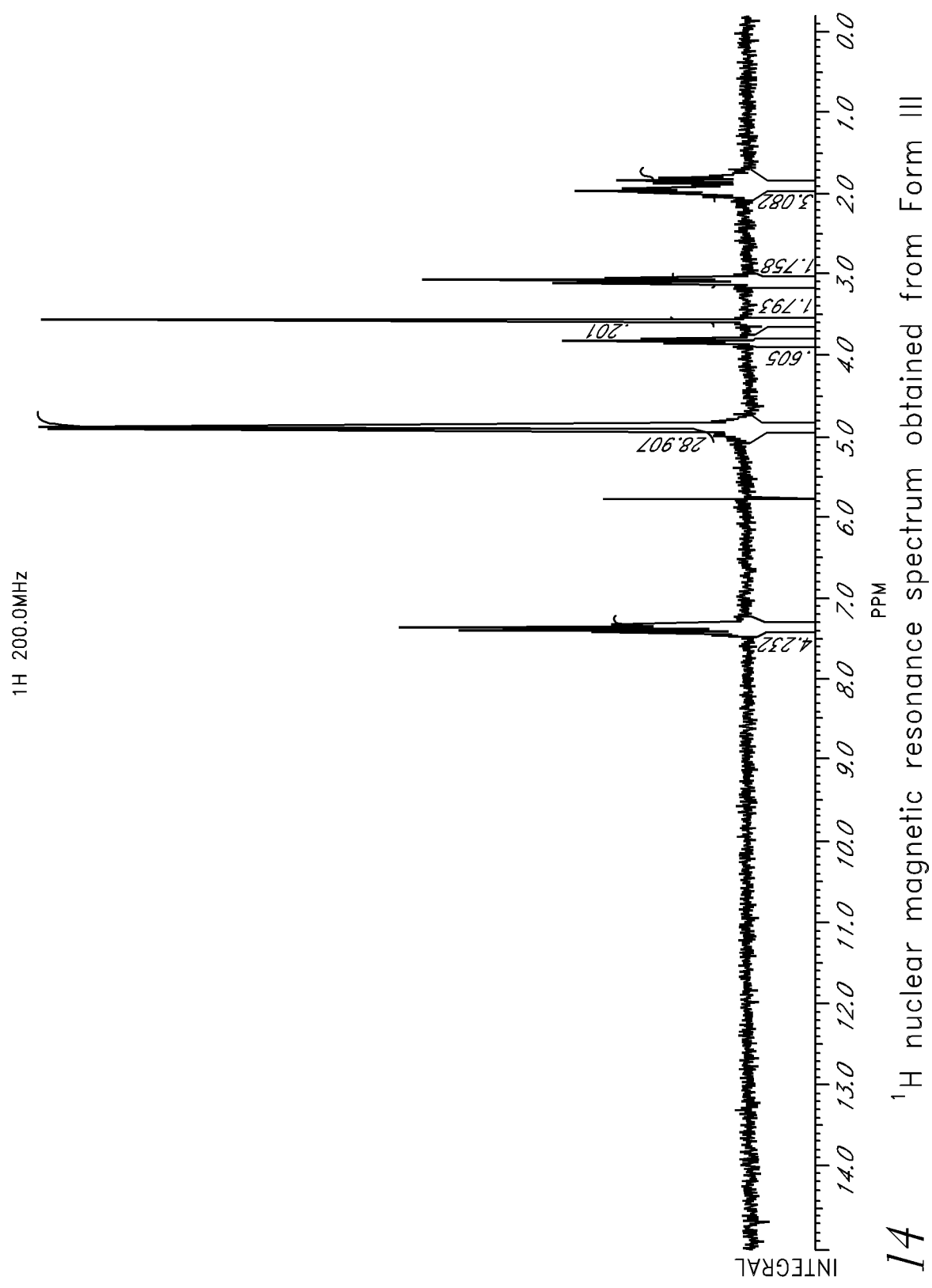
FIG. 14 shows the $^1$H nuclear magnetic resonance spectrum obtained from a sample of Form III.
Figure 15:
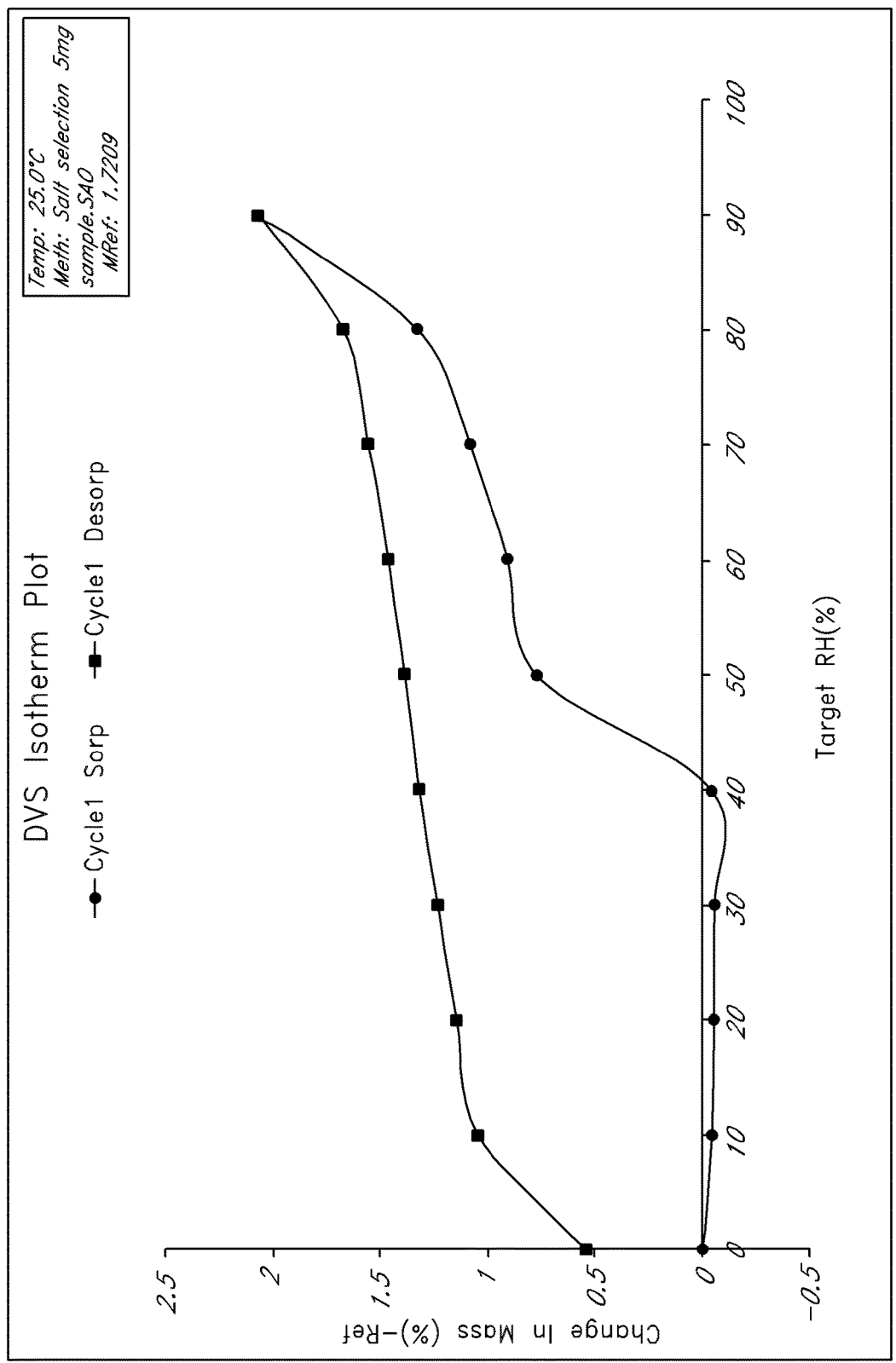
FIG. 15 shows dynamic vapor sorption results for Form III.

FIG. 14 shows nuclear magnetic resonance (NMR) integrals and chemical shifts for Form III. The integrals confirm the presence of L-ornithine phenyl acetate: 7.5 (aromatic CH), 3.8 (CH adjacent to NH2), 3.6 (CH2 unit of phenyl acetate), 3.15 (CH2 adjacent to NH2) and 1.9 (aliphatic CH2 units) ppm (integrals: 5:1:2:2:4 protons; 4.2, 0.8, 1.7, 1.7, 3.0). Amine protons and hydroxyl protons were not observed due to proton exchange at both the zwitterion and site of salt formation. Meanwhile, FIG. 15 shows dynamic vapor sorption (DVS) results for Form III, and show a water uptake of about 2.0% by weight. XRPD results following DVS analysis (not shown) confirm that Form III did not transition to a different polymorph. Form III therefore exhibits greater water uptake compared to Forms I and II; however Form III is still characterized as non-hygroscopic and stable over a wide range of humidity at room temperature.

Form V

The precise conditions for forming crystalline Form V may be empirically determined and it is only possible to give a number of methods which have been found to be suitable in practice.

Thus, for example, Form V may be obtained by placing a saturated solution of L-ornithine phenyl acetate in a cooled temperature environment of about −21° C., where the solution is cyclohexanone. As another example, the same saturated solution may yield Form V when evaporating the solvent.

Form V also forms from saturated solutions of L-ornithine phenyl acetate having diisopropyl ether as a solvent. For example, a saturated solution having a solvent ratio of about 1 to 2 of diisopropyl ether and IPA will yield Form V when placed in a cooled temperature environment of about 4° C. Similarly, a solution having only the solvent diisopropyl ether can yield Form V when placed in a cooled temperature environment of about −21° C.

Figure 16:
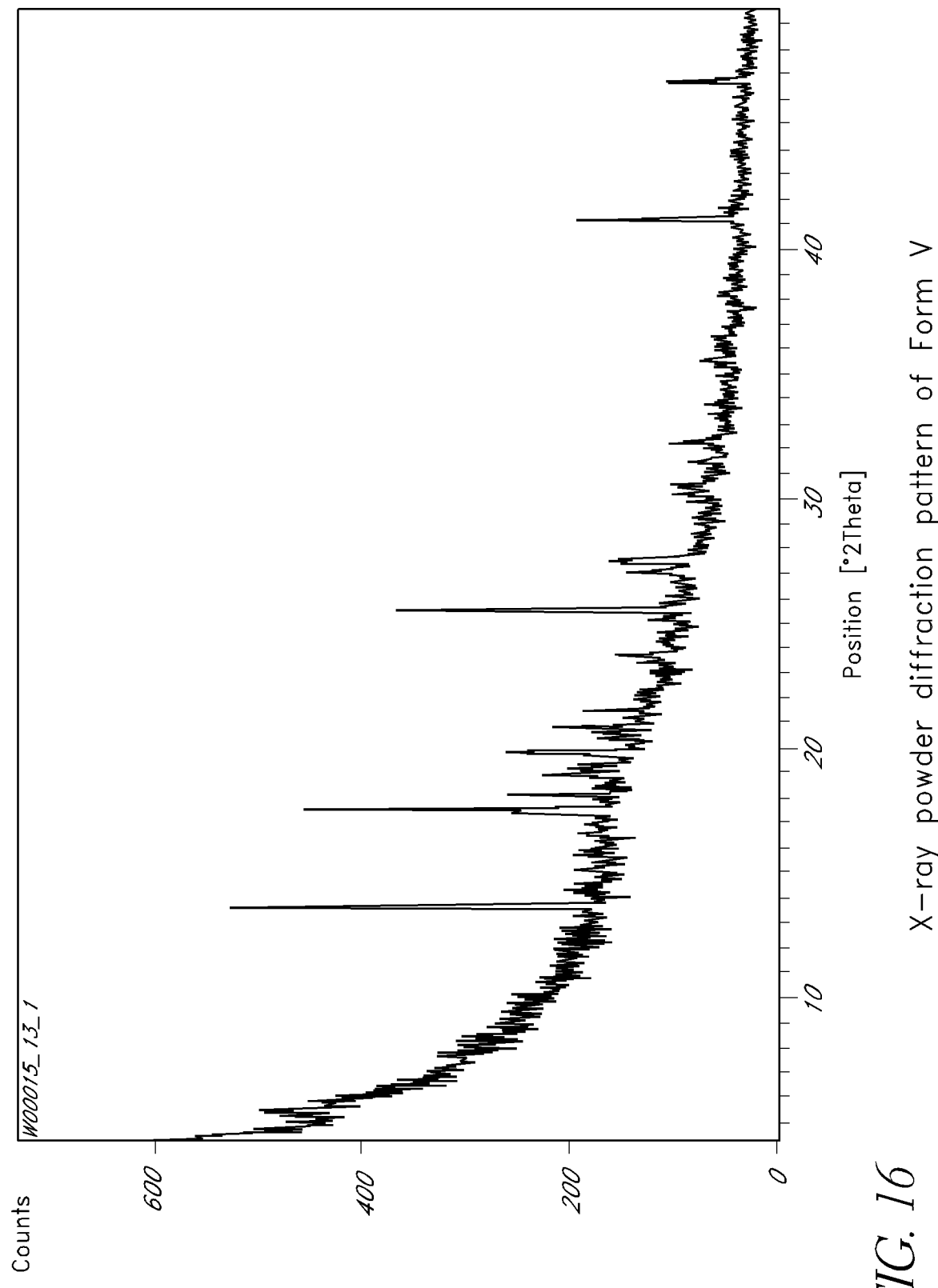
FIG. 16 is an X-ray powder diffraction pattern of Form V.

FIG. 16 shows the crystalline structure of Form V as determined by XRPD. Form V, which may be obtained by the methods disclosed above, exhibits characteristic peaks at approximately 13.7°, 17.4°, 19.8°, 20.6° and 23.7° 2θ. Thus, in some embodiments, a crystalline form of L-ornithine phenyl acetate has one or more characteristic peaks (e.g., one, two, three, four, or five characteristic peaks) selected from approximately 13.7°, 17.4°, 19.8°, 20.6° and 23.7° 2θ.

Figure 17:
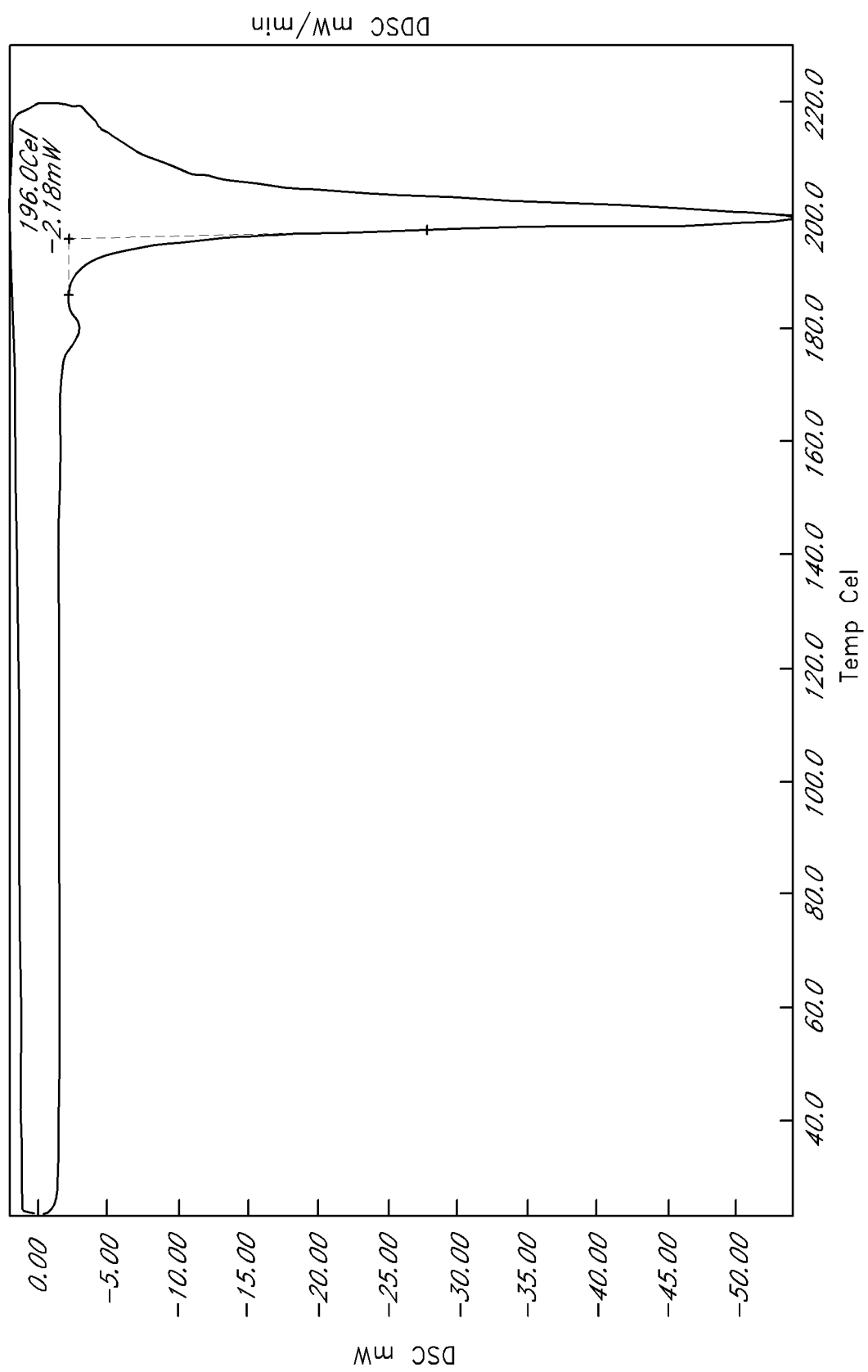
FIG. 17 shows differential scanning calorimetry results for Form V.
Figure 18:
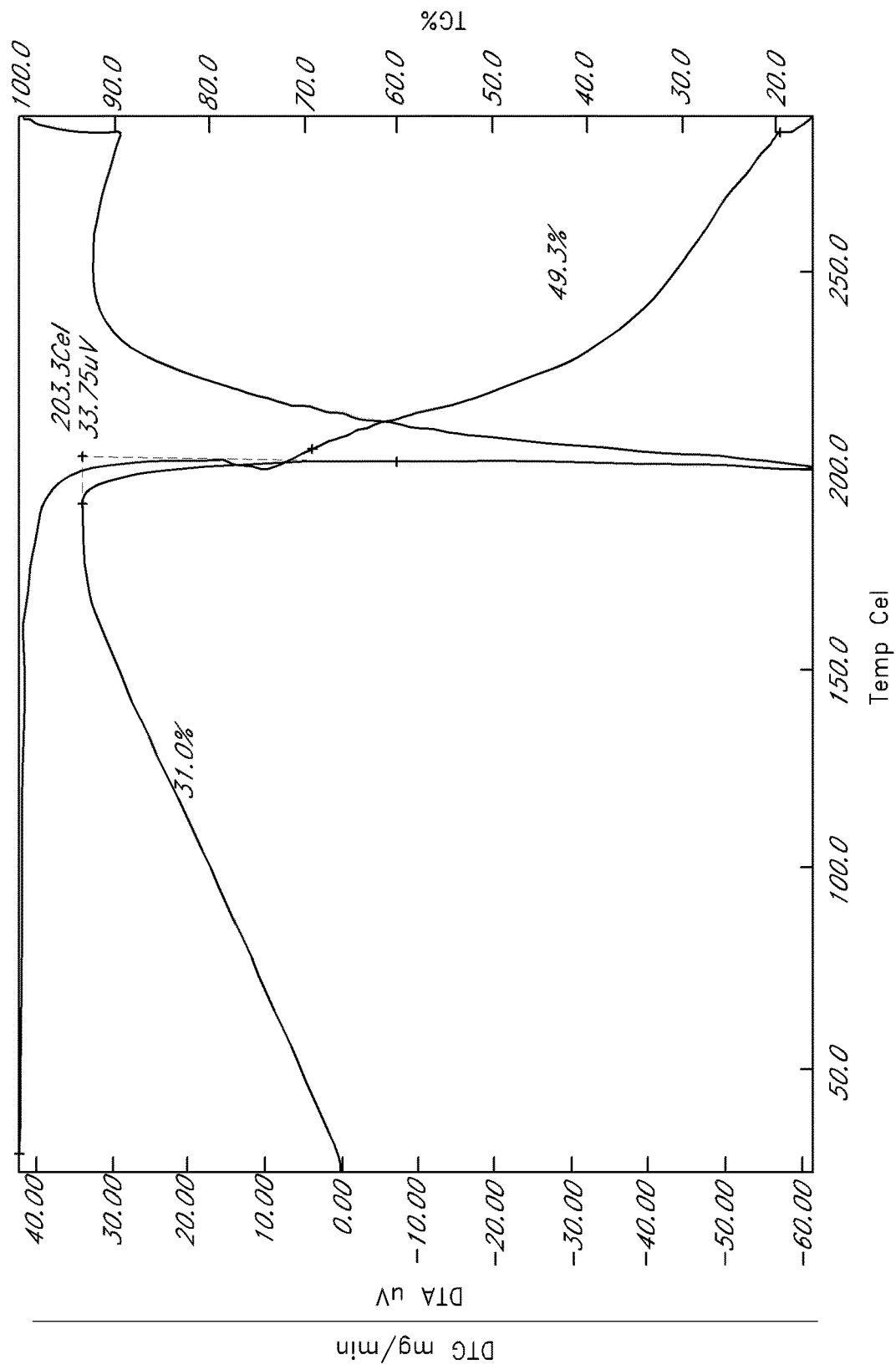
FIG. 18 shows thermogravimetric gravimetric/differential thermal analysis of Form V.

FIG. 17 shows results obtained by differential scanning calorimetry (DSC) for Form V. These results indicate a melting point of about 196° C., which is below the melting point of other forms. Form V also exhibits an endotherm at about 174° C. Form V was also analyzed using thermal gravimetric analysis (TGA), as shown in FIG. 18, and exhibits no significant weight loss before the melting point. Form V may therefore be characterized as anhydrous. The melting point of about 196° C. could also be observed by TGA testing. Accordingly, in some embodiments, a crystalline form of L-ornithine phenyl acetate exhibits a melting point of about 196° C. In some embodiments, a crystalline form of L-ornithine phenyl acetate is characterized by differential scanning calorimetry as having an endotherm at about 174° C. In some embodiments, a crystalline form of L-ornithine phenyl acetate is anhydrous.

Figure 19:
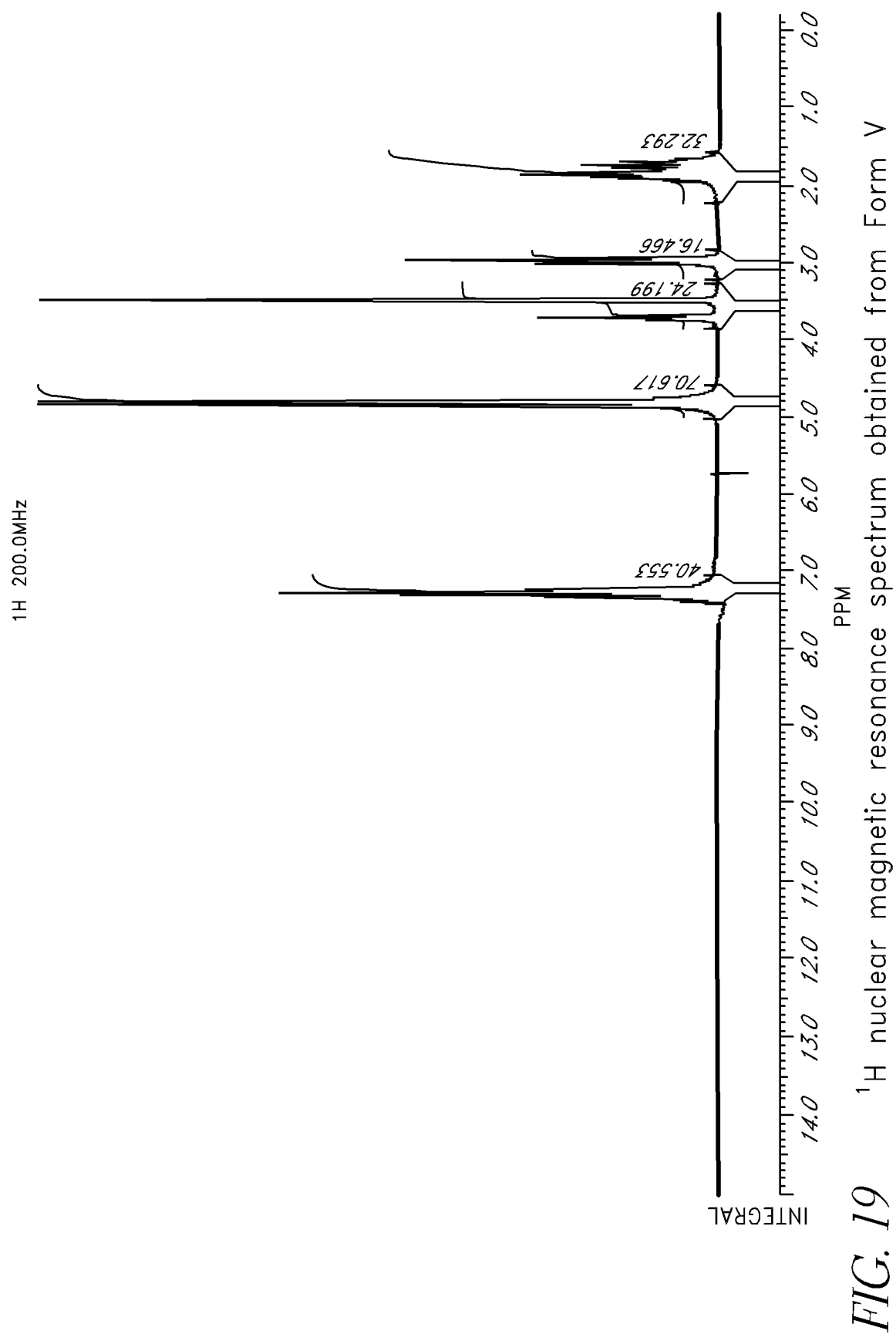
FIG. 19 shows the $^1$H nuclear magnetic resonance spectrum obtained from a sample of Form V.
Figure 20:
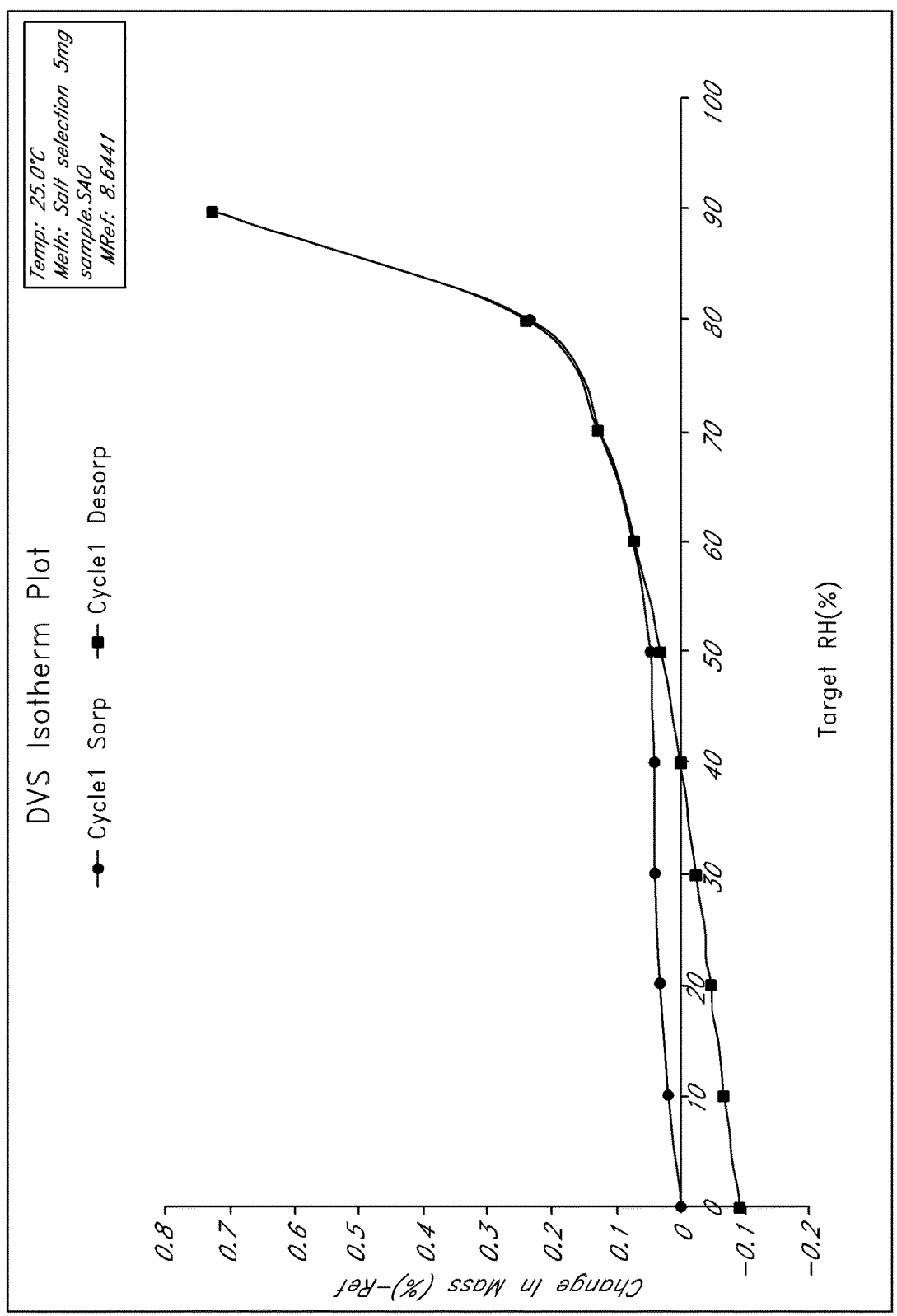
FIG. 20 shows dynamic vapor sorption results for Form V.

FIG. 19 shows nuclear magnetic resonance (NMR) integrals and chemical shifts for Form V. The integrals confirm the presence of L-ornithine phenyl acetate: 7.5 (aromatic CH), 3.8 (CH adjacent to NH2), 3.6 (CH2 unit of phenyl acetate), 3.15 (CH2 adjacent to NH2) and 1.9 (aliphatic CH2 units) ppm (integrals: 5:1:2:2:4 protons; 4.2, 0.8, 1.7, 1.7, 3.0). Amine protons and hydroxyl protons were not observed due to proton exchange at both the zwitterion and site of salt formation. Meanwhile, FIG. 19 shows dynamic vapor sorption (DVS) results for Form V, and show a water uptake of about 0.75% by weight. XRPD results following DVS analysis (not shown) suggest that Form V transitioned to Form II, but the chemical composition was unchanged. Form V is therefore characterized as non-hygroscopic, but not stable over a wide range of humidity.

A 7-day stability study of Form V at 40° C./75% RH indicated that a transformation to Form II occurred under these conditions; however the chemical composition was unchanged. Accordingly, Form V is most likely metastable.

Methods of Treating Liver Decompensation or Hepatic Encephalopathy

L-Ornithine phenyl acetate, and accordingly any of the compositions of L-ornithine phenyl acetate disclosed herein, may be administered to a subject for treating or ameliorating the onset of liver decompensation or hepatic encephalopathy. L-Ornithine phenyl acetate can thus be administered to improve the condition of a subject, for example a subject suffering from chronic liver disease following a precipitating event. As another example, L-ornithine phenyl acetate may be administered to combat or delay the onset of liver decompensation or hepatic encephalopathy.

L-Ornithine phenyl acetate may be administered in combination to a subject for treatment of hepatic encephalopathy. L-Ornithine phenyl acetate may be administered to improve the condition of a patient suffering from hepatic encephalopathy. L-Ornithine phenyl acetate may be administered to alleviate the symptoms associated with hepatic encephalopathy. L-Ornithine phenyl acetate may be administered to combat hepatic encephalopathy. L-Ornithine phenyl acetate may be administered to prevent or reduce the likelihood of an initial hepatic encephalopathic episode in a person at risk for hepatic encephalopathic episodes. L-Ornithine phenyl acetate may be administered to lessen the severity of an initial hepatic encephalopathic episode in a person at risk for hepatic encephalopathic episodes. L-Ornithine phenyl acetate may be administered to delay an initial hepatic encephalopathic episode in a person at risk for hepatic encephalopathic episodes.

Development of liver decompensation and hepatic encephalopathy commonly involves "precipitating events" (or "acute attacks"). Such precipitating events include gastrointestinal bleeding, infection (sepsis), portal vein thrombosis and dehydration. The onset of such an acute attack is likely to lead to hospitalization. The patient may suffer one of these acute attacks or a combination of these acute attacks.

A subject who has had or is suspected of having had an acute attack is treated according to the invention with L-ornithine phenyl acetate to prevent or reduce the likelihood of progression of the liver to the decompensated state. Consequently, L-ornithine phenyl acetate can prevent or reduce the likelihood of the medical consequences of liver decompensation such as hepatic encephalopathy. L-Ornithine phenyl acetate may be used to preserve liver function. Use of L-ornithine phenyl acetate may thus extend the life of a patient with liver disease. In one embodiment, the metabolic consequences of a gastrointestinal bleed such as hyperammonemia, hypoisoleucemia and reduced protein synthesis in the post-bleeding period are prevented.

Typically, treatment of subjects may begin as soon as possible after the onset or the suspected onset of a precipitating event (acute attack). Preferably, treatment of the subject begins prior to repeated acute attacks. More preferably, treatment of the subject begins following the first acute attack. Thus, in some embodiments, the subject treated with L-ornithine phenyl acetate is identified as having the onset or the suspected onset of a precipitating event (acute attack).

Treatment is typically given promptly after the start of an acute attack. Treatment may begin after the symptom(s) of an acute attack or suspected acute attack have been detected e.g. by a medic such as a physician, a paramedic or a nurse. Treatment may begin upon hospitalization of the subject. Treatment may thus begin within 6 hours, within 3 hours, within 2 hours or within 1 hour after the symptom(s) of an acute attack or suspected acute attack have been detected. Treatment of the subject may therefore begin from 1 to 48 hours, for example from 1 to 36 hours or from 1 to 24 hours after the symptom(s) of an acute attack or suspected acute attack have been detected.

Treatment may occur for up to 8 weeks, for example up to 6 weeks, up to 4 weeks or up to 2 weeks after the symptom(s) of an acute attack or suspected acute attack have been detected. Treatment may therefore occur for up to 48 hours, for example for up to 36 hours or for up to 24 hours after the symptom(s) of an acute attack or suspected acute attack have been detected. Typically, treatment occurs to the time when recovery from the acute precipitating event is evident.

L-Ornithine phenyl acetate may also be used to treat or ameliorate hyperammonemia. Thus, L-ornithine phenyl acetate may be administered to patients identified as having excess ammonia levels in the blood, or patients exhibiting symptoms of excess ammonia in the blood. L-Ornithine phenyl acetate may also be administered to reduce the risk of hyperammonemia. In some embodiments, L-ornithine phenyl acetate can be administered daily, for an indefinite period of time. For example, daily dosages may be administered for the life of the patient, or until a physician determines the patient no longer exhibits a risk for hyperammonemia. In some embodiments, a therapeutically effective amount of L-ornithine phenyl acetate is administered to reduce the risk of hyperammonemia. In some embodiments, a therapeutically effective amount of L-ornithine phenyl acetate is administered orally for the prophylaxis of hyperammonemia.

A therapeutically effective amount of L-ornithine phenyl acetate is administered to the subject. As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. (See e.g., Fingl et al. 1975, in "The Pharmacological Basis of Therapeutics", which is hereby incorporated herein by reference in its entirety, with particular reference to Ch. 1, p. 1). The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

A typical dose of L-ornithine phenyl acetate may be from about 0.02 to about 1.25 g/kg of bodyweight (preferably from about 0.1 to about 0.6 g/kg of bodyweight). A dosage may therefore be from about 500 mg to about 50 g (preferably about 5 g to about 40 g, and more preferably about 10 g to about 30 g).

A single daily dose may be administered. Alternatively, multiple doses, for example two, three, four or five doses may be administered. Such multiple doses may be administered over a period of one month or two weeks or one week. In some embodiments, a single dose or multiple doses such as two, three, four or five doses may be administered daily.

EXAMPLES AND EXPERIMENTAL METHODS

Additional embodiments are disclosed in further detail in the following examples, which are not in any way intended to limit the scope of the claims.

X-ray Powder Diffraction (XRPD)

XRPD analysis was carried out on a Bruker D8 advance or Siemens D5000, scanning the samples between 4° and 50° 2θ. In embodiments using the Bruker D8 device, approximately 5 mg of a sample was gently compressed on the XRPD zero back ground single 96 well plate sample holder. The sample was then loaded into a Bruker D8-Discover diffractometer in transmission mode and analysed using the following experimental conditions.

| | |
|---|---|
| Operator | D8-Discover |
| Raw Data Origin | BRUKER-binary V3 (.RAW) |
| Scan Axis | Gonio |
| Start Position [°2θ.] | 4.0000 |
| End Position [°2θ.] | 49.9800 |
| Step Size [°2θ.] | 0.0200 |
| Scan Step Time [s] | 39.1393 |
| Scan Type | Continuous |
| Offset [°2θ.] | 0.0000 |

-continued

| | |
|---|---|
| Divergence Slit Type | Fixed |
| Divergence Slit Size [°] | 2.0000 |
| Specimen Length [mm] | 10.00 |
| Receiving Slit Size [mm] | 0.1000 |
| Measurement Temperature [° C.] | 25.00 |
| Anode Material | Cu |
| K-Alpha1 [Å] | 1.54060 |
| K-Alpha2 [Å] | 1.54443 |
| K-Beta [Å] | 1.39225 |
| K-A2/K-A1 Ratio | 0.50000 |
| Generator Settings | 40 mA, 40 kV |
| Diffractometer Type | Unknown |
| Diffractometer Number | 0 |
| Goniometer Radius [mm] | 250.00 |
| Dist. Focus-Diverg. Slit [mm] | 91.00 |
| Incident Beam Monochromator | No |
| Spinning | No |

In embodiments using the Seimens D5000 device, approximately 5 mg of sample was gently compressed on glass slide containing a thin layer of holding grease. The sample was then loaded into a Seimens D5000 diffractometer running in reflection mode and analysed, whilst spinning, using the following experimental conditions.

| | |
|---|---|
| Raw Data Origin | Siemens-binary V2 (.RAW) |
| Start Position [°2θ.] | 3.0000 |
| End Position [°2θ.] | 50.000 |
| Step Size [°2θ.] | 0.0200 |
| Scan Step Time [s] | 0.8 |
| Scan Type | Continuous |
| Offset [°2θ.] | 0.0000 |
| Divergence Slit Type | Fixed |
| Divergence Slit Size [°] | 1.0000 |
| Specimen Length [mm] | various |
| Receiving Slit Size [mm] | 0.2000 |
| Measurement Temperature [° C.] | 20.00 |
| Anode Material | Cu |
| K-Alpha1 [Å] | 1.54060 |
| K-Alpha2 [Å] | 1.54443 |
| K-Beta [Å] | 1.39225 |
| K-A2/K-A1 Ratio | 0.50000 (nominal) |
| Generator Settings | 40 mA, 40 kV |
| Diffractometer Type | d5000 |
| Diffractometer Number | 0 |
| Goniometer Radius [mm] | 217.50 |
| Incident Beam Monochromator | No |
| Diffracted Beam Monochromator | (Graphite) |
| Spinning | Yes |

Single Crystal X-ray Diffraction (SXRD)

All measurements were carried out using a Bruker Smart Apex diffractometer operating with Mo-Kα radiation. Unless otherwise specified the data were obtained in 60 ω-scan 10 s images collected in three separate settings of 2θ and φ.

Differential Scanning Calorimetry (DSC)

Approximately 5 mg of sample was weighed into an aluminium DSC pan and sealed with a pierced aluminium lid (non-hermetically). The sample pan was then loaded into a Seiko DSC6200 (equipped with a cooler), cooled, and held at 25° C. Once a stable heat-flow response was obtained, the sample and reference were then heated to about 250° C. at a scan rate of 10° C./min and the resulting heat flow response monitored. Prior to analysis, the instrument was temperature and heat-flow calibrated using an indium reference standard. Sample analysis was carried out by Muse measurement software where the temperatures of thermal events were quoted as the onset temperature, measured according to the manufacturer's specifications.

Thermogravimetric Gravimetric/Differential Thermal Analysis (TG/DTA)

Approximately 5 mg of sample was weighed into an aluminium pan and loaded into a simultaneous thermogravimetric/differential thermal analyser (DTA) and held at room temperature. The sample was then heated at a rate of 10° C./min from 25° C. to 300° C. during which time the change in sample weight was monitored along with any thermal events (DTA). Nitrogen was used as the purge gas, at a flow rate of 20 cm$^3$/min. Prior to analysis the instrument was weight and temperature calibrated using a 100 mg reference weight and an indium reference standard, respectively.

Dynamic Vapor Sorption (DVS)

Approximately 10 mg of sample was placed into a wire-mesh vapor sorption balance pan and loaded into a DVS-1 dynamic vapor sorption balance supplied by Scientific and Medical Systems (SMS). The sample was then dried by maintaining a 0% humidity environment until no further weight change was recorded. The sample was then subjected to a ramping profile from 0-90% relative humidity (RH) at 10% increments, maintaining the sample at each step until a stable weight had been achieved (99.5% step completion). After completion of the sorption cycle, the sample was then dried using the same procedure. The weight change during the sorption/desorption cycles were then plotted, allowing for the hygroscopic nature of the sample to be determined.

$^1$H Nuclear Magnetic Resonance (NMR)

$^1$H NMR was performed on a Bruker AC200. An NMR of each sample was performed in d-$H_2O$ and each sample was prepared to about 5 mg concentration. The NMR spectra for L-ornithine benzoate and L-ornithine phenyl acetate are provided in FIGS. 21 and 22, respectively.

Solubility Approximations

Approximately, 25 mg portions of the sample were placed in vials 5 volume increments of the appropriate solvent system were added. Between each addition, the mixture was checked for dissolution and if no dissolution was apparent, the mixture was warmed to 50° C., and checked again. The procedure was continued until dissolution was observed or when 100 volumes of solvent had been added.

HPLC Solubility Determinations

Slurries of each solvent were prepared and the samples shaken for about 48 hrs at 25° C. Each sample was then drawn through a filter, and the filtrate transferred to an HPLC vial for analysis. From the data the solubility of L-ornithine phenyl acetate for each solvent was determined.

Temperature Cycling Experiments

Using the information gathered from the solubility approximations, slurries of the sample were prepared in 24 selected solvent systems. The slurries were temperature cycled at 40° C. or 25° C. in 4 hour cycles for a period of 72 hours. The solids were visually checked for any obvious signs of degradation (i.e. color changes) and then, if not degraded, isolated by filtration. The solids were allowed to dry at ambient conditions for about 24 hours prior to analysis.

Crash Cooling Experiments

Crash cooling experiments were performed by placing saturated solutions of the sample, in the 24 selected solvent systems, in environments of 4° C. and −21° C. for about 48 hours. Any solid material was recovered and the solids were allowed to dry at ambient conditions for about 24 hours prior to analysis.

Evaporation Experiments

Evaporation experiments were conducted by allowing saturated solutions of the sample to evaporate freely at ambient conditions. The solid material was then recovered after the material had evaporated to dryness and analyzed.

Anti-Solvent Addition Experiments

Anti-solvent addition experiments were conducted by adding anti-solvent to saturated solutions of the sample. The addition was continued until there was no further precipitation and the samples adjusted to various temperature for 24 hours: elevated, ambient, 4° C. or −21°. The solid was then isolated and dried at ambient conditions for about 24 hours prior to analysis.

Polarized Light Microscopy (PLM)

The presence of crystallinity (birefringence) was determined using a Leica Leitz DMRB polarised optical microscope equipped with a high resolution Leica camera and image capture software (Firecam V.1.0). All images were recorded using a 10× objective, unless otherwise stated.

Silver Analysis

All silver analysis was carried out on an Agilent 7500ce ICP-MS.

Intrinsic Dissolution Rates

Approximately 100 mg of each form was compressed into discs by placing the material into a die (diameter 12 mm) and compressing the die under 5 tons of pressure in a hydraulic press for about 2 minutes. The dissolution instrument, Sotax AT7 conforms to EP2 and USP2 in which paddles were used to stir the media. Each form was tested under the following pH conditions; 1.0, 4.5 and 6.7, in the stationary disc mode (i.e. discs were added at time=0 seconds and allowed to sink to the bottom of the media). 1 $cm^3$ aliquots of media were extracted from the dissolution pots at times 10, 20, 30, 40, 50, 60, 70, 80 and 120 seconds and tested for API concentration by HPLC. Dissolution curves were plotted and from the first 6 or 7 points on the curves the intrinsic dissolution rate curves were calculated. All tests were carried out at 37° C. and a paddle speed of 150 rpm.

HPLC-UV Instrument Details
Instrument: Agilent 1200
Column: Gemini C18, 5 μm, 150.0×4.6 mm
Column Temperature: 40° C.
Mobile Phase A: Phosphate Buffer
Mobile Phase B: Acetonitrile
Elution: Gradient
λ: 210 nm
Injection Volume: 10 μL
Flow Rate: 1 mL/min Thin Layer Chromatography (TLC)

A small spot of solution containing the sample was applied to a plate, about one centimeter from the base. The plate is then dipped into the TLC tank (sealed container) containing methanol:ethyl acetate (95:5) solvent mixture. The solvent moves up the plate by capillary action and meets the sample mixture, which is dissolved and is carried up the plate by the solvent mixture. The number of spots was noted and the $R_f$ values were calculated for each spot.

Infrared (IR)

Infrared spectroscopy was carried out on a Bruker ALPHA P spectrometer. Sufficient material was placed onto the centre of the plate of the spectrometer and the spectra were obtained using the following parameters:

Resolution: 4 cm-1
Background Scan Time: 16 scans
Sample Scan Time: 16 scans
Data Collection: 4000 to 400 cm-1
Result Spectrum: Transmittance
Software: OPUS version 6

Stabilities Studies: pH 1, 4, 7, 10 and 14 Environments

Slurries (supersaturated solution: about 250 μl of pH solution and solid was added until dissolution was no longer observed and ca. 100 mg of solid was in the slurry) were prepared for each form in a variety of pH environments; 1, 4, 7, 10 and 13.2. The slurries were shaken constantly for a period of 14 days and measurements taken at 7 and 14 day time points. Appropriate buffers were prepared for each pH and are detailed further below.

A buffer having a pH value of 1 was prepared by dissolving 372.75 mg of potassium chloride in 25 ml of deionized water to give a 0.2 M solution. Subsequently, 67 ml of 0.2 M hydrochloric acid was added (this was prepared from a 5 M solution; 10 ml was added to 40 ml of deionized water giving a 1 M solution which was diluted further; 20 ml was added to 80 ml of deionized water giving the required 0.2 M solution) to achieve the desired pH.

A buffer having a pH value of 4 was prepared by dissolving 1.02 g of potassium hydrogen phthalate in 50 ml of deionized water to give a 0.1 M solution.

A buffer having a pH value of 7 was prepared by dissolving 680.00 mg of potassium phosphate monobasic in 50 ml of deionized water to give a 0.1 M solution. Subsequently, 29.1 ml of 0.1 M sodium hydroxide was added (this was prepared from a 1 M solution; 5 ml was added to 45 ml of deionized water giving the required 0.1 M solution) to achieve the desired pH.

A buffer having a pH value of 10 was prepared by dissolving 210.00 mg of sodium bicarbonate in 50 ml of deionized water to give a 0.05 M solution. Subsequently, 10.7 ml of 0.1 M sodium hydroxide was added (this was prepared from a 1 M solution; 5 ml was added to 45 ml of deionized water giving the required 0.1 M solution) to achieve the desired pH.

A buffer having a pH value of pH 13.2 by dissolving 372.75 mg of potassium chloride in 25 ml of deionized water to give a 0.2 M solution. Subsequently, 66 ml of 0.2 M sodium hydroxide was added (this was prepared from a 1 M solution; 20 ml was added to 80 ml of deionized water giving the required 0.2 M solution) taking the pH to 13. 1M sodium hydroxide was then added drop wise to achieve the desired pH.

Example 1

Precipitating Crystalline Forms

Saturated solutions of L-ornithine phenyl acetate were subjected to temperature cycling, crash cooling, evaporation, or anti-solvent addition as described above. The precipitate was analyzed by PLM and XRPD to determine the crystalline form (if any). The results are summarized in TABLE 5.

Six unique crystalline forms were identified from the precipitation studies, Forms I-VI. However, Forms IV and VI were obtained from solutions of acetic acid, and NMR results confirmed these forms to be L-ornithine acetate. Meanwhile, Tests 540-611 utilized samples of L-ornithine phenyl acetate originally isolated by the addition of ethanol anti-solvent. Many of these example produced Form I, which is an ethanol solvate, and therefore it is believed these samples originally included residual ethanol. Consequently, Form I may not be reproduced for certain conditions if the original sample does not include residual ethanol.

TABLE 5

Examples of Preparing Crystalline Forms

| Test | Crystallization Method | Solvent | Results |
|---|---|---|---|
| 1 | Temp. Cycling | cyclohexanone | Form II |
| 2 | Controlled Cool (4° C.) | cyclohexanone | No Solid |
| 3 | Controlled Cool (−21° C.) | cyclohexanone | Form V |
| 4 | Evaporation | cyclohexanone | Form V |
| 5 | Anti-Solvent (IPA) Addition Elevated Temperature | cyclohexanone | No Solid |
| 6 | Anti-Solvent (IPA) Addition Ambient Temperature | cyclohexanone | Form II |
| 7 | Anti-Solvent (IPA) Addition (4° C.) | cyclohexanone | Form II |
| 8 | Anti-Solvent (IPA) Addition (−21° C.) | cyclohexanone | Form II |
| 9 | Anti-Solvent (Ethanol) Addition Ambient Temperature | cyclohexanone | Form II |
| 10 | Anti-Solvent (Ethanol) Addition (4° C.) | cyclohexanone | Form I |
| 11 | Anti-Solvent (Ethanol) Addition (−21° C.) | cyclohexanone | Form I |
| 12 | Temp. Cycling | ethanol/acetone (50:50) | Form II |
| 13 | Controlled Cool (4° C.) | ethanol/acetone (50:50) | No Solid |
| 14 | Controlled Cool (−21° C.) | ethanol/acetone (50:50) | Form III |
| 15 | Evaporation | ethanol/acetone (50:50) | Form II |
| 16 | Anti-Solvent (IPA) Addition Elevated Temperature | ethanol/acetone (50:50) | Form II |
| 17 | Anti-Solvent (IPA) Addition Ambient Temperature | ethanol/acetone (50:50) | Form II |
| 18 | Anti-Solvent (IPA) Addition (4° C.) | ethanol/acetone (50:50) | Form II |
| 19 | Anti-Solvent (IPA) Addition (−21° C.) | ethanol/acetone (50:50) | Form II |
| 20 | Anti-Solvent (Ethanol) Addition Ambient Temperature | ethanol/acetone (50:50) | Form II |
| 21 | Anti-Solvent (Ethanol) Addition (4° C.) | ethanol/acetone (50:50) | Form I |
| 22 | Anti-Solvent (Ethanol) Addition (−21° C.) | ethanol/acetone (50:50) | Form I |
| 23 | Temp. Cycling | acetic acid | Form IV |
| 24 | Controlled Cool (4° C.) | acetic acid | No Solid |
| 25 | Controlled Cool (−21° C.) | acetic acid | No Solid |
| 26 | Evaporation | acetic acid | Form II |
| 27 | Anti-Solvent (IPA) Addition Elevated Temperature | acetic acid | Form VI |
| 28 | Anti-Solvent (IPA) Addition Ambient Temperature | acetic acid | Form IV |
| 29 | Anti-Solvent (IPA) Addition (4° C.) | acetic acid | Form IV |
| 30 | Anti-Solvent (IPA) Addition (−21° C.) | acetic acid | Form IV |
| 31 | Anti-Solvent (Ethanol) Addition Ambient Temperature | acetic acid | Form IV |
| 32 | Anti-Solvent (Ethanol) Addition (4° C.) | acetic acid | Form IV |
| 33 | Anti-Solvent (Ethanol) Addition (−21° C.) | acetic acid | Form IV |
| 34 | Temp. Cycling | 1-propanol | Form II |
| 35 | Controlled Cool (4° C.) | 1-propanol | Form II |
| 36 | Controlled Cool (−21° C.) | 1-propanol | Form II |
| 37 | Evaporation | 1-propanol | Form II |
| 38 | Anti-Solvent (IPA) Addition Elevated Temperature | 1-propanol | Form II |
| 39 | Anti-Solvent (IPA) Addition Ambient Temperature | 1-propanol | Form II |
| 40 | Anti-Solvent (IPA) Addition (4° C.) | 1-propanol | Form II |
| 41 | Anti-Solvent (IPA) Addition (−21° C.) | 1-propanol | Form II |
| 42 | Anti-Solvent (Ethanol) Addition Ambient Temperature | 1-propanol | Form II |
| 43 | Anti-Solvent (Ethanol) Addition (4° C.) | 1-propanol | Form I/II |
| 44 | Anti-Solvent (Ethanol) Addition (−21° C.) | 1-propanol | Form I |
| 45 | Temp. Cycling | dimethylcarbonate | Form II |
| 46 | Controlled Cool (4° C.) | dimethylcarbonate | No Solid |
| 47 | Controlled Cool (−21° C.) | dimethylcarbonate | Form II |
| 48 | Evaporation | dimethylcarbonate | Form II |
| 49 | Anti-Solvent (IPA) Addition Elevated Temperature | dimethylcarbonate | Form II |
| 50 | Anti-Solvent (IPA) Addition Ambient Temperature | dimethylcarbonate | Form II |
| 51 | Anti-Solvent (IPA) Addition (4° C.) | dimethylcarbonate | Form II |
| 52 | Anti-Solvent (IPA) Addition (−21° C.) | dimethylcarbonate | Form II |
| 53 | Anti-Solvent (Ethanol) Addition Ambient Temperature | dimethylcarbonate | Form II |
| 54 | Anti-Solvent (Ethanol) Addition (4° C.) | dimethylcarbonate | Form I |
| 55 | Anti-Solvent (Ethanol) Addition (−21° C.) | dimethylcarbonate | Form II |
| 56 | Temp. Cycling | NMP | Form II |
| 57 | Controlled Cool (4° C.) | NMP | Form II |
| 58 | Controlled Cool (−21° C.) | NMP | Form II |
| 59 | Evaporation | NMP | Form II |
| 60 | Anti-Solvent (IPA) Addition Elevated Temperature | NMP | Form II |
| 61 | Anti-Solvent (IPA) Addition Ambient Temperature | NMP | Form II |
| 62 | Anti-Solvent (IPA) Addition (4° C.) | NMP | Form II |
| 63 | Anti-Solvent (IPA) Addition (−21° C.) | NMP | Form II |
| 64 | Anti-Solvent (Ethanol) Addition Ambient Temperature | NMP | Form II |
| 65 | Anti-Solvent (Ethanol) Addition (4° C.) | NMP | Form I/II |
| 66 | Anti-Solvent (Ethanol) Addition (−21° C.) | NMP | Form II |
| 67 | Temp. Cycling | EtOAc/cyclohexane (1:2) | Form II |
| 68 | Controlled Cool (4° C.) | EtOAc/cyclohexane (1:2) | No Solid |
| 69 | Controlled Cool (−21° C.) | EtOAc/cyclohexane (1:2) | No Solid |
| 70 | Evaporation | etOAc/cyclohexane (1:2) | Form II |
| 71 | Anti-Solvent (IPA) Addition Elevated Temperature | etOAc/cyclohexane (1:2) | Form II |
| 72 | Anti-Solvent (IPA) Addition Ambient Temperature | etOAc/cyclohexane (1:2) | Form II |
| 73 | Anti-Solvent (IPA) Addition (4° C.) | etOAc/cyclohexane (1:2) | Form II |
| 74 | Anti-Solvent (IPA) Addition (−21° C.) | etOAc/cyclohexane (1:2) | Form II |

TABLE 5-continued

Examples of Preparing Crystalline Forms

| Test | Crystallization Method | Solvent | Results |
|---|---|---|---|
| 75 | Anti-Solvent (Ethanol) Addition Ambient Temperature | etOAc/cyclohexane (1:2) | Form II |
| 76 | Anti-Solvent (Ethanol) Addition (4° C.) | etOAc/cyclohexane (1:2) | Form I |
| 77 | Anti-Solvent (Ethanol) Addition (−21° C.) | etOAc/cyclohexane (1:2) | Form I/II |
| 78 | Temp. Cycling | etOAc/toluene (1:2) | Form II |
| 79 | Controlled Cool (4° C.) | etOAc/toluene (1:2) | No Solid |
| 80 | Controlled Cool (−21° C.) | etOAc/toluene (1:2) | Form II |
| 81 | Evaporation | etOAc/toluene (1:2) | Form II |
| 82 | Anti-Solvent (IPA) Addition Elevated Temperature | etOAc/toluene (1:2) | Form II |
| 83 | Anti-Solvent (IPA) Addition Ambient Temperature | etOAc/toluene (1:2) | Form II |
| 84 | Anti-Solvent (IPA) Addition (4° C.) | etOAc/toluene (1:2) | Form II |
| 85 | Anti-Solvent (IPA) Addition (−21° C.) | etOAc/toluene (1:2) | Form II |
| 86 | Anti-Solvent (Ethanol) Addition Ambient Temperature | etOAc/toluene (1:2) | Form II |
| 87 | Anti-Solvent (Ethanol) Addition (4° C.) | etOAc/toluene (1:2) | Form I |
| 88 | Anti-Solvent (Ethanol) Addition (−21° C.) | etOAc/toluene (1:2) | Form II |
| 89 | Temp. Cycling | IPA/diisopropyl ether (1:2) | Form II |
| 90 | Controlled Cool (4° C.) | IPA/diisopropyl ether (1:2) | Form V |
| 91 | Controlled Cool (−21° C.) | IPA/diisopropyl ether (1:2) | Form II |
| 92 | Evaporation | IPA/diisopropyl ether (1:2) | Form II |
| 93 | Anti-Solvent (IPA) Addition Elevated Temperature | IPA/diisopropyl ether (1:2) | Form II |
| 94 | Anti-Solvent (IPA) Addition Ambient Temperature | IPA/diisopropyl ether (1:2) | Form II |
| 95 | Anti-Solvent (IPA) Addition (4° C.) | IPA/diisopropyl ether (1:2) | Form II |
| 96 | Anti-Solvent (IPA) Addition (−21° C.) | IPA/diisopropyl ether (1:2) | Form II |
| 97 | Anti-Solvent (Ethanol) Addition Ambient Temperature | IPA/diisopropyl ether (1:2) | Form II |
| 98 | Anti-Solvent (Ethanol) Addition (4° C.) | IPA/diisopropyl ether (1:2) | Form I |
| 99 | Anti-Solvent (Ethanol) Addition (−21° C.) | IPA/diisopropyl ether (1:2) | Form I/II |
| 100 | Temp. Cycling | DIPE | Form II |
| 101 | Controlled Cool (4° C.) | DIPE | No Solid |
| 102 | Controlled Cool (−21° C.) | DIPE | Form V |
| 103 | Evaporation | DIPE | Form II |
| 104 | Anti-Solvent (IPA) Addition Elevated Temperature | DIPE | Form II |
| 105 | Anti-Solvent (IPA) Addition Ambient Temperature | DIPE | Form II |
| 106 | Anti-Solvent (IPA) Addition (4° C.) | DIPE | Form II |
| 107 | Anti-Solvent (IPA) Addition (−21° C.) | DIPE | Form II |
| 108 | Anti-Solvent (Ethanol) Addition Ambient Temperature | DIPE | Form II |
| 109 | Anti-Solvent (Ethanol) Addition (4° C.) | DIPE | Form I |
| 110 | Anti-Solvent (Ethanol) Addition (−21° C.) | DIPE | Form II |
| 111 | Temp. Cycling | nitromethane/water (20%) | No Solid |
| 112 | Controlled Cool (4° C.) | nitromethane/water (20%) | No Solid |
| 113 | Controlled Cool (−21° C.) | nitromethane/water (20%) | No Solid |
| 114 | Evaporation | nitromethane/water (20%) | Form II |
| 115 | Anti-Solvent (IPA) Addition Elevated Temperature | nitromethane/water (20%) | No Solid |
| 116 | Anti-Solvent (IPA) Addition Ambient Temperature | nitromethane/water (20%) | Form II |
| 117 | Anti-Solvent (IPA) Addition (4° C.) | nitromethane/water (20%) | Form II |
| 118 | Anti-Solvent (IPA) Addition (−21° C.) | nitromethane/water (20%) | Form II |
| 119 | Anti-Solvent (Ethanol) Addition Ambient Temperature | nitromethane/water (20%) | Form II |
| 120 | Anti-Solvent (Ethanol) Addition (4° C.) | nitromethane/water (20%) | Form I |
| 121 | Anti-Solvent (Ethanol) Addition (−21° C.) | nitromethane/water (20%) | Form I/II |
| 122 | Temp. Cycling | acetone/water (20%) | No Solid |
| 123 | Controlled Cool (4° C.) | acetone/water (20%) | Form II |
| 124 | Controlled Cool (−21° C.) | acetone/water (20%) | Form II |
| 125 | Evaporation | acetone/water (20%) | Form II |
| 126 | Anti-Solvent (IPA) Addition Elevated Temperature | acetone/water (20%) | Form II |
| 127 | Anti-Solvent (IPA) Addition Ambient Temperature | acetone/water (20%) | Form II |
| 128 | Anti-Solvent (IPA) Addition (4° C.) | acetone/water (20%) | Form II |
| 129 | Anti-Solvent (IPA) Addition (−21° C.) | acetone/water (20%) | Form II |
| 130 | Anti-Solvent (Ethanol) Addition Ambient Temperature | acetone/water (20%) | Form II |
| 131 | Anti-Solvent (Ethanol) Addition (4° C.) | acetone/water (20%) | Form I |
| 132 | Anti-Solvent (Ethanol) Addition (−21° C.) | acetone/water (20%) | Form II |
| 133 | Temp. Cycling | 1,4 dioxane/water (20%) | Form II |
| 134 | Controlled Cool (4° C.) | 1,4 dioxane/water (20%) | Form II |
| 135 | Controlled Cool (−21° C.) | 1,4 dioxane/water (20%) | No Solid |
| 136 | Evaporation | 1,4 dioxane/water (20%) | Form II |
| 137 | Anti-Solvent (IPA) Addition Elevated Temperature | 1,4 dioxane/water (20%) | Form II |
| 138 | Anti-Solvent (IPA) Addition Ambient Temperature | 1,4 dioxane/water (20%) | Form II |
| 139 | Anti-Solvent (IPA) Addition (4° C.) | 1,4 dioxane/water (20%) | Form II |
| 140 | Anti-Solvent (IPA) Addition (−21° C.) | 1,4 dioxane/water (20%) | Form II |
| 141 | Anti-Solvent (Ethanol) Addition Ambient Temperature | 1,4 dioxane/water (20%) | Form II |
| 142 | Anti-Solvent (Ethanol) Addition (4° C.) | 1,4 dioxane/water (20%) | Form I |
| 143 | Anti-Solvent (Ethanol) Addition (−21° C.) | 1,4 dioxane/water (20%) | Form II |
| 144 | Temp. Cycling | diethyl ether | Form II |
| 145 | Controlled Cool (4° C.) | diethyl ether | No Solid |
| 146 | Controlled Cool (−21° C.) | diethyl ether | No Solid |
| 147 | Evaporation | diethyl ether | Form II |

TABLE 5-continued

Examples of Preparing Crystalline Forms

| Test | Crystallization Method | Solvent | Results |
|---|---|---|---|
| 148 | Anti-Solvent (IPA) Addition Elevated Temperature | diethyl ether | Form II |
| 149 | Anti-Solvent (IPA) Addition Ambient Temperature | diethyl ether | Form II |
| 150 | Anti-Solvent (IPA) Addition (4° C.) | diethyl ether | Form II |
| 151 | Anti-Solvent (IPA) Addition (−21° C.) | diethyl ether | Form II |
| 152 | Anti-Solvent (Ethanol) Addition Ambient Temperature | diethyl ether | Form II |
| 153 | Anti-Solvent (Ethanol) Addition (4° C.) | diethyl ether | Form I |
| 154 | Anti-Solvent (Ethanol) Addition (−21° C.) | diethyl ether | Form I/II |
| 155 | Temp. Cycling | ethylene glycol | Form II |
| 156 | Controlled Cool (4° C.) | ethylene glycol | No Solid |
| 157 | Controlled Cool (−21° C.) | ethylene glycol | No Solid |
| 158 | Evaporation | ethylene glycol | No Solid |
| 159 | Anti-Solvent (IPA) Addition Elevated Temperature | ethylene glycol | Form II |
| 160 | Anti-Solvent (IPA) Addition Ambient Temperature | ethylene glycol | Form II |
| 161 | Anti-Solvent (IPA) Addition (4° C.) | ethylene glycol | Form II |
| 162 | Anti-Solvent (IPA) Addition (−21° C.) | ethylene glycol | Form II |
| 163 | Anti-Solvent (Ethanol) Addition Ambient Temperature | ethylene glycol | Form II |
| 164 | Anti-Solvent (Ethanol) Addition (4° C.) | ethylene glycol | Form II |
| 165 | Anti-Solvent (Ethanol) Addition (−21° C.) | ethylene glycol | Form II |
| 166 | Temp. Cycling | meOAc/water (20%) | No Solid |
| 167 | Controlled Cool (4° C.) | meOAc/water (20%) | No Solid |
| 168 | Controlled Cool (−21° C.) | meOAc/water (20%) | No Solid |
| 169 | Evaporation | meOAc/water (20%) | Form II |
| 170 | Anti-Solvent (IPA) Addition Elevated Temperature | meOAc/water (20%) | Form II |
| 171 | Anti-Solvent (IPA) Addition Ambient Temperature | meOAc/water (20%) | Form II |
| 172 | Anti-Solvent (IPA) Addition (4° C.) | meOAc/water (20%) | Form II |
| 173 | Anti-Solvent (IPA) Addition (−21° C.) | meOAc/water (20%) | Form II |
| 174 | Anti-Solvent (Ethanol) Addition Ambient Temperature | meOAc/water (20%) | Form II |
| 175 | Anti-Solvent (Ethanol) Addition (4° C.) | meOAc/water (20%) | Form I/II |
| 176 | Anti-Solvent (Ethanol) Addition (−21° C.) | meOAc/water (20%) | Form II |
| 177 | Temp. Cycling | meOH/acetone (50:50) | Form II |
| 178 | Controlled Cool (4° C.) | meOH/acetone (50:50) | No Solid |
| 179 | Controlled Cool (−21° C.) | meOH/acetone (50:50) | No Solid |
| 180 | Evaporation | meOH/acetone (50:50) | Form II |
| 181 | Anti-Solvent (IPA) Addition Elevated Temperature | meOH/acetone (50:50) | Form II |
| 182 | Anti-Solvent (IPA) Addition Ambient Temperature | meOH/acetone (50:50) | Form II |
| 183 | Anti-Solvent (IPA) Addition (4° C.) | meOH/acetone (50:50) | Form II |
| 184 | Anti-Solvent (IPA) Addition (−21° C.) | meOH/acetone (50:50) | Form II |
| 185 | Anti-Solvent (Ethanol) Addition Ambient Temperature | meOH/acetone (50:50) | Form II |
| 186 | Anti-Solvent (Ethanol) Addition (4° C.) | meOH/acetone (50:50) | Form I |
| 187 | Anti-Solvent (Ethanol) Addition (−21° C.) | meOH/acetone (50:50) | Form I/II |
| 188 | Temp. Cycling | DMF | Form II |
| 189 | Controlled Cool (4° C.) | DMF | Form II |
| 190 | Controlled Cool (−21° C.) | DMF | Form II |
| 191 | Evaporation | DMF | Form II |
| 192 | Anti-Solvent (IPA) Addition Elevated Temperature | DMF | Form II |
| 193 | Anti-Solvent (IPA) Addition Ambient Temperature | DMF | Form II |
| 194 | Anti-Solvent (IPA) Addition (4° C.) | DMF | Form II |
| 195 | Anti-Solvent (IPA) Addition (−21° C.) | DMF | Form II |
| 196 | Anti-Solvent (Ethanol) Addition Ambient Temperature | DMF | Form II |
| 197 | Anti-Solvent (Ethanol) Addition (4° C.) | DMF | Form I/II |
| 198 | Anti-Solvent (Ethanol) Addition (−21° C.) | DMF | Form II |
| 199 | Temp. Cycling | 2-butanol | Form II |
| 200 | Controlled Cool (4° C.) | 2-butanol | No Solid |
| 201 | Controlled Cool (−21° C.) | 2-butanol | No Solid |
| 202 | Evaporation | 2-butanol | Form II |
| 203 | Anti-Solvent (IPA) Addition Elevated Temperature | 2-butanol | Form III |
| 204 | Anti-Solvent (IPA) Addition Ambient Temperature | 2-butanol | Form II |
| 205 | Anti-Solvent (IPA) Addition (4° C.) | 2-butanol | Form II |
| 206 | Anti-Solvent (IPA) Addition (−21° C.) | 2-butanol | Form II |
| 207 | Anti-Solvent (Ethanol) Addition Ambient Temperature | 2-butanol | Form II |
| 208 | Anti-Solvent (Ethanol) Addition (4° C.) | 2-butanol | Form I/II |
| 209 | Anti-Solvent (Ethanol) Addition (−21° C.) | 2-butanol | Form I/II |
| 210 | Temp. Cycling | cumene | Form II |
| 211 | Controlled Cool (4° C.) | cumene | No Solid |
| 212 | Controlled Cool (−21° C.) | cumene | No Solid |
| 213 | Evaporation | cumene | Form II |
| 214 | Anti-Solvent (IPA) Addition Elevated Temperature | cumene | Form II |
| 215 | Anti-Solvent (IPA) Addition Ambient Temperature | cumene | Form II |
| 216 | Anti-Solvent (IPA) Addition (4° C.) | cumene | Form II |
| 217 | Anti-Solvent (IPA) Addition (−21° C.) | cumene | Form II |
| 218 | Anti-Solvent (Ethanol) Addition Ambient Temperature | cumene | Form II |
| 219 | Anti-Solvent (Ethanol) Addition (4° C.) | cumene | Form II |
| 220 | Anti-Solvent (Ethanol) Addition (−21° C.) | cumene | Form I/II |
| 221 | Temp. Cycling | ethyl formate | Form II |
| 222 | Controlled Cool (4° C.) | ethyl formate | No Solid |
| 223 | Controlled Cool (−21° C.) | ethyl formate | Form II |

TABLE 5-continued

Examples of Preparing Crystalline Forms

| Test | Crystallization Method | Solvent | Results |
|---|---|---|---|
| 224 | Evaporation | ethyl formate | Form II |
| 225 | Anti-Solvent (IPA) Addition Elevated Temperature | ethyl formate | Form II |
| 226 | Anti-Solvent (IPA) Addition Ambient Temperature | ethyl formate | Form II |
| 227 | Anti-Solvent (IPA) Addition (4° C.) | ethyl formate | Form II |
| 228 | Anti-Solvent (IPA) Addition (−21° C.) | ethyl formate | Form II |
| 229 | Anti-Solvent (Ethanol) Addition Ambient Temperature | ethyl formate | Form II |
| 230 | Anti-Solvent (Ethanol) Addition (4° C.) | ethyl formate | Form I |
| 231 | Anti-Solvent (Ethanol) Addition (−21° C.) | ethyl formate | Form I/II |
| 232 | Temp. Cycling | isobutyl acetate | Form II |
| 233 | Controlled Cool (4° C.) | isobutyl acetate | No Solid |
| 234 | Controlled Cool (−21° C.) | isobutyl acetate | Form II |
| 235 | Evaporation | isobutyl acetate | No Solid |
| 236 | Anti-Solvent (IPA) Addition Elevated Temperature | isobutyl acetate | Form II |
| 237 | Anti-Solvent (IPA) Addition Ambient Temperature | isobutyl acetate | Form II |
| 238 | Anti-Solvent (IPA) Addition (4° C.) | isobutyl acetate | Form II |
| 239 | Anti-Solvent (IPA) Addition (−21° C.) | isobutyl acetate | Form III |
| 240 | Anti-Solvent (Ethanol) Addition Ambient Temperature | isobutyl acetate | Form II |
| 241 | Anti-Solvent (Ethanol) Addition (4° C.) | isobutyl acetate | Form II |
| 242 | Anti-Solvent (Ethanol) Addition (−21° C.) | isobutyl acetate | Form I/II |
| 243 | Temp. Cycling | 3-methyl-1-butanol | Form II |
| 244 | Controlled Cool (4° C.) | 3-methyl-1-butanol | No Solid |
| 245 | Controlled Cool (−21° C.) | 3-methyl-1-butanol | No Solid |
| 246 | Evaporation | 3-methyl-1-butanol | Form II |
| 247 | Anti-Solvent (IPA) Addition Elevated Temperature | 3-methyl-1-butanol | Form II |
| 248 | Anti-Solvent (IPA) Addition Ambient Temperature | 3-methyl-1-butanol | Form II |
| 249 | Anti-Solvent (IPA) Addition (4° C.) | 3-methyl-1-butanol | Form II |
| 250 | Anti-Solvent (IPA) Addition (−21° C.) | 3-methyl-1-butanol | Form II |
| 251 | Anti-Solvent (Ethanol) Addition Ambient Temperature | 3-methyl-1-butanol | Form II |
| 252 | Anti-Solvent (Ethanol) Addition (4° C.) | 3-methyl-1-butanol | Form I/II |
| 253 | Anti-Solvent (Ethanol) Addition (−21° C.) | 3-methyl-1-butanol | Form I/II |
| 254 | Temp. Cycling | anisole | Form II |
| 255 | Controlled Cool (4° C.) | anisole | No Solid |
| 256 | Controlled Cool (−21° C.) | anisole | Form II |
| 257 | Evaporation | anisole | Form II |
| 258 | Anti-Solvent (IPA) Addition Elevated Temperature | anisole | Form II |
| 259 | Anti-Solvent (IPA) Addition Ambient Temperature | anisole | Form II |
| 260 | Anti-Solvent (IPA) Addition (4° C.) | anisole | Form II |
| 261 | Anti-Solvent (IPA) Addition (−21° C.) | anisole | Form II/IV |
| 262 | Anti-Solvent (Ethanol) Addition Ambient Temperature | anisole | Form II |
| 263 | Anti-Solvent (Ethanol) Addition (4° C.) | anisole | Form II |
| 264 | Anti-Solvent (Ethanol) Addition (−21° C.) | anisole | Form I |
| 265 | Temp. Cycling | IPA/isopropyl acetate (1:2) | Form II |
| 266 | Controlled Cool (4° C.) | IPA/isopropyl acetate (1:2) | No Solid |
| 267 | Controlled Cool (−21° C.) | IPA/isopropyl acetate (1:2) | No Solid |
| 268 | Evaporation | IPA/isopropyl acetate (1:2) | Form II |
| 269 | Anti-Solvent (IPA) Addition Elevated Temperature | IPA/isopropyl acetate (1:2) | Form II |
| 270 | Anti-Solvent (IPA) Addition Ambient Temperature | IPA/isopropyl acetate (1:2) | Form II |
| 271 | Anti-Solvent (IPA) Addition (4° C.) | IPA/isopropyl acetate (1:2) | Form II |
| 272 | Anti-Solvent (IPA) Addition (−21° C.) | IPA/isopropyl acetate (1:2) | Form II |
| 273 | Anti-Solvent (Ethanol) Addition Ambient Temperature | IPA/isopropyl acetate (1:2) | Form II |
| 274 | Anti-Solvent (Ethanol) Addition (4° C.) | IPA/isopropyl acetate (1:2) | Form II |
| 275 | Anti-Solvent (Ethanol) Addition (−21° C.) | IPA/isopropyl acetate (1:2) | Form I |
| 276 | Temp. Cycling | EtOH: 1% $H_2O$ | Form II |
| 277 | Controlled Cool (4° C.) | EtOH: 1% $H_2O$ | No Solid |
| 278 | Controlled Cool (−21° C.) | EtOH: 1% $H_2O$ | No Solid |
| 279 | Evaporation | EtOH: 1% $H_2O$ | No Solid |
| 280 | Anti-Solvent (IPA) Addition Elevated Temperature | EtOH: 1% $H_2O$ | No Solid |
| 281 | Anti-Solvent (IPA) Addition Ambient Temperature | EtOH: 1% $H_2O$ | No Solid |
| 282 | Anti-Solvent (IPA) Addition (4° C.) | EtOH: 1% $H_2O$ | No Solid |
| 283 | Anti-Solvent (IPA) Addition (−21° C.) | EtOH: 1% $H_2O$ | No Solid |
| 284 | Anti-Solvent (Ethanol) Addition Ambient Temperature | EtOH: 1% $H_2O$ | No Solid |
| 285 | Anti-Solvent (Ethanol) Addition (4° C.) | EtOH: 1% $H_2O$ | No Solid |
| 286 | Anti-Solvent (Ethanol) Addition (−21° C.) | EtOH: 1% $H_2O$ | No Solid |
| 287 | Temp. Cycling | EtOH: 3% $H_2O$ | Form II |
| 288 | Controlled Cool (4° C.) | EtOH: 3% $H_2O$ | No Solid |
| 289 | Controlled Cool (−21° C.) | EtOH: 3% $H_2O$ | No Solid |
| 290 | Evaporation | EtOH: 3% $H_2O$ | No Solid |
| 291 | Anti-Solvent (IPA) Addition Elevated Temperature | EtOH: 3% $H_2O$ | No Solid |
| 292 | Anti-Solvent (IPA) Addition Ambient Temperature | EtOH: 3% $H_2O$ | No Solid |
| 293 | Anti-Solvent (IPA) Addition (4° C.) | EtOH: 3% $H_2O$ | No Solid |
| 294 | Anti-Solvent (IPA) Addition (−21° C.) | EtOH: 3% $H_2O$ | No Solid |
| 295 | Anti-Solvent (Ethanol) Addition Ambient Temperature | EtOH: 3% $H_2O$ | No Solid |
| 296 | Anti-Solvent (Ethanol) Addition (4° C.) | EtOH: 3% $H_2O$ | No Solid |
| 297 | Anti-Solvent (Ethanol) Addition (−21° C.) | EtOH: 3% $H_2O$ | No Solid |
| 298 | Temp. Cycling | EtOH: 5% $H_2O$ | Form II |

TABLE 5-continued

Examples of Preparing Crystalline Forms

| Test | Crystallization Method | Solvent | Results |
|---|---|---|---|
| 299 | Controlled Cool (4° C.) | EtOH: 5% H₂O | No Solid |
| 300 | Controlled Cool (−21° C.) | EtOH: 5% H₂O | No Solid |
| 301 | Evaporation | EtOH: 5% H₂O | Form II |
| 302 | Anti-Solvent (IPA) Addition Elevated Temperature | EtOH: 5% H₂O | No Solid |
| 303 | Anti-Solvent (IPA) Addition Ambient Temperature | EtOH: 5% H₂O | Form II |
| 304 | Anti-Solvent (IPA) Addition (4° C.) | EtOH: 5% H₂O | No Solid |
| 305 | Anti-Solvent (IPA) Addition (−21° C.) | EtOH: 5% H₂O | No Solid |
| 306 | Anti-Solvent (Ethanol) Addition Ambient Temperature | EtOH: 5% H₂O | No Solid |
| 307 | Anti-Solvent (Ethanol) Addition (4° C.) | EtOH: 5% H₂O | No Solid |
| 308 | Anti-Solvent (Ethanol) Addition (−21° C.) | EtOH: 5% H₂O | No Solid |
| 309 | Temp. Cycling | IPA: 1% H₂O | Form II |
| 310 | Controlled Cool (4° C.) | IPA: 1% H₂O | No Solid |
| 311 | Controlled Cool (−21° C.) | IPA: 1% H₂O | No Solid |
| 312 | Evaporation | IPA: 1% H₂O | No Solid |
| 313 | Anti-Solvent (IPA) Addition Elevated Temperature | IPA: 1% H₂O | No Solid |
| 314 | Anti-Solvent (IPA) Addition Ambient Temperature | IPA: 1% H₂O | No Solid |
| 315 | Anti-Solvent (IPA) Addition (4° C.) | IPA: 1% H₂O | No Solid |
| 316 | Anti-Solvent (IPA) Addition (−21° C.) | IPA: 1% H₂O | No Solid |
| 317 | Anti-Solvent (Ethanol) Addition Ambient Temperature | IPA: 1% H₂O | No Solid |
| 318 | Anti-Solvent (Ethanol) Addition (4° C.) | IPA: 1% H₂O | No Solid |
| 319 | Anti-Solvent (Ethanol) Addition (−21° C.) | IPA: 1% H₂O | No Solid |
| 320 | Temp. Cycling | IPA: 3% H₂O | Form II |
| 321 | Controlled Cool (4° C.) | IPA: 3% H₂O | No Solid |
| 322 | Controlled Cool (−21° C.) | IPA: 3% H₂O | No Solid |
| 323 | Evaporation | IPA: 3% H₂O | No Solid |
| 324 | Anti-Solvent (IPA) Addition Elevated Temperature | IPA: 3% H₂O | No Solid |
| 325 | Anti-Solvent (IPA) Addition Ambient Temperature | IPA: 3% H₂O | No Solid |
| 326 | Anti-Solvent (IPA) Addition (4° C.) | IPA: 3% H₂O | No Solid |
| 327 | Anti-Solvent (IPA) Addition (−21° C.) | IPA: 3% H₂O | No Solid |
| 328 | Anti-Solvent (Ethanol) Addition Ambient Temperature | IPA: 3% H₂O | No Solid |
| 329 | Anti-Solvent (Ethanol) Addition (4° C.) | IPA: 3% H₂O | No Solid |
| 330 | Anti-Solvent (Ethanol) Addition (−21° C.) | IPA: 3% H₂O | No Solid |
| 331 | Temp. Cycling | IPA: 5% H₂O | Form II |
| 332 | Controlled Cool (4° C.) | IPA: 5% H₂O | No Solid |
| 333 | Controlled Cool (−21° C.) | IPA: 5% H₂O | No Solid |
| 334 | Evaporation | IPA: 5% H₂O | Form II |
| 335 | Anti-Solvent (IPA) Addition Elevated Temperature | IPA: 5% H₂O | No Solid |
| 336 | Anti-Solvent (IPA) Addition Ambient Temperature | IPA: 5% H₂O | No Solid |
| 337 | Anti-Solvent (IPA) Addition (4° C.) | IPA: 5% H₂O | No Solid |
| 338 | Anti-Solvent (IPA) Addition (−21° C.) | IPA: 5% H₂O | No Solid |
| 339 | Anti-Solvent (Ethanol) Addition Ambient Temperature | IPA: 5% H₂O | No Solid |
| 340 | Anti-Solvent (Ethanol) Addition (4° C.) | IPA: 5% H₂O | No Solid |
| 341 | Anti-Solvent (Ethanol) Addition (−21° C.) | IPA: 5% H₂O | No Solid |
| 342 | Temp. Cycling | ACN: 1% H₂O | Form II |
| 343 | Controlled Cool (4° C.) | ACN: 1% H₂O | No Solid |
| 344 | Controlled Cool (−21° C.) | ACN: 1% H₂O | No Solid |
| 345 | Evaporation | ACN: 1% H₂O | Form II |
| 346 | Anti-Solvent (IPA) Addition Elevated Temperature | ACN: 1% H₂O | No Solid |
| 347 | Anti-Solvent (IPA) Addition Ambient Temperature | ACN: 1% H₂O | No Solid |
| 348 | Anti-Solvent (IPA) Addition (4° C.) | ACN: 1% H₂O | No Solid |
| 349 | Anti-Solvent (IPA) Addition (−21° C.) | ACN: 1% H₂O | No Solid |
| 350 | Anti-Solvent (Ethanol) Addition Ambient Temperature | ACN: 1% H₂O | No Solid |
| 351 | Anti-Solvent (Ethanol) Addition (4° C.) | ACN: 1% H₂O | No Solid |
| 352 | Anti-Solvent (Ethanol) Addition (−21° C.) | ACN: 1% H₂O | No Solid |
| 353 | Temp. Cycling | ACN: 6% H₂O | Form II |
| 354 | Controlled Cool (4° C.) | ACN: 6% H₂O | No Solid |
| 355 | Controlled Cool (−21° C.) | ACN: 6% H₂O | No Solid |
| 356 | Evaporation | ACN: 6% H₂O | Form II |
| 357 | Anti-Solvent (IPA) Addition Elevated Temperature | ACN: 6% H₂O | No Solid |
| 358 | Anti-Solvent (IPA) Addition Ambient Temperature | ACN: 6% H₂O | No Solid |
| 359 | Anti-Solvent (IPA) Addition (4° C.) | ACN: 6% H₂O | No Solid |
| 360 | Anti-Solvent (IPA) Addition (−21° C.) | ACN: 6% H₂O | No Solid |
| 361 | Anti-Solvent (Ethanol) Addition Ambient Temperature | ACN: 6% H₂O | No Solid |
| 362 | Anti-Solvent (Ethanol) Addition (4° C.) | ACN: 6% H₂O | No Solid |
| 363 | Anti-Solvent (Ethanol) Addition (−21° C.) | ACN: 6% H₂O | No Solid |
| 364 | Temp. Cycling | ACN: 12% H₂O | No Solid |
| 365 | Controlled Cool (4° C.) | ACN: 12% H₂O | No Solid |
| 366 | Controlled Cool (−21° C.) | ACN: 12% H₂O | No Solid |
| 367 | Evaporation | ACN: 12% H₂O | Form II |
| 368 | Anti-Solvent (IPA) Addition Elevated Temperature | ACN: 12% H₂O | No Solid |
| 369 | Anti-Solvent (IPA) Addition Ambient Temperature | ACN: 12% H₂O | Form II |
| 370 | Anti-Solvent (IPA) Addition (4° C.) | ACN: 12% H₂O | No Solid |
| 371 | Anti-Solvent (IPA) Addition (−21° C.) | ACN: 12% H₂O | Form II |
| 372 | Anti-Solvent (Ethanol) Addition Ambient Temperature | ACN: 12% H₂O | No Solid |
| 373 | Anti-Solvent (Ethanol) Addition (4° C.) | ACN: 12% H₂O | No Solid |
| 374 | Anti-Solvent (Ethanol) Addition (−21° C.) | ACN: 12% H₂O | No Solid |
| 375 | Temp. Cycling | DMF: 5% H₂O | Form II |
| 376 | Controlled Cool (4° C.) | DMF: 5% H₂O | No Solid |
| 377 | Controlled Cool (−21° C.) | DMF: 5% H₂O | No Solid |

TABLE 5-continued

Examples of Preparing Crystalline Forms

| Test | Crystallization Method | Solvent | Results |
|---|---|---|---|
| 378 | Evaporation | DMF: 5% H$_2$O | No Solid |
| 379 | Anti-Solvent (IPA) Addition Elevated Temperature | DMF: 5% H$_2$O | No Solid |
| 380 | Anti-Solvent (IPA) Addition Ambient Temperature | DMF: 5% H$_2$O | No Solid |
| 381 | Anti-Solvent (IPA) Addition (4° C.) | DMF: 5% H$_2$O | No Solid |
| 382 | Anti-Solvent (IPA) Addition (−21° C.) | DMF: 5% H$_2$O | No Solid |
| 383 | Anti-Solvent (Ethanol) Addition Ambient Temperature | DMF: 5% H$_2$O | No Solid |
| 384 | Anti-Solvent (Ethanol) Addition (4° C.) | DMF: 5% H$_2$O | No Solid |
| 385 | Anti-Solvent (Ethanol) Addition (−21° C.) | DMF: 5% H$_2$O | No Solid |
| 386 | Temp. Cycling | DMF: 15% H$_2$O | Form II |
| 387 | Controlled Cool (4° C.) | DMF: 15% H$_2$O | No Solid |
| 388 | Controlled Cool (−21° C.) | DMF: 15% H$_2$O | No Solid |
| 389 | Evaporation | DMF: 15% H$_2$O | No Solid |
| 390 | Anti-Solvent (IPA) Addition Elevated Temperature | DMF: 15% H$_2$O | No Solid |
| 391 | Anti-Solvent (IPA) Addition Ambient Temperature | DMF: 15% H$_2$O | No Solid |
| 392 | Anti-Solvent (IPA) Addition (4° C.) | DMF: 15% H$_2$O | No Solid |
| 393 | Anti-Solvent (IPA) Addition (−21° C.) | DMF: 15% H$_2$O | No Solid |
| 394 | Anti-Solvent (Ethanol) Addition Ambient Temperature | DMF: 15% H$_2$O | No Solid |
| 395 | Anti-Solvent (Ethanol) Addition (4° C.) | DMF: 15% H$_2$O | No Solid |
| 396 | Anti-Solvent (Ethanol) Addition (−21° C.) | DMF: 15% H$_2$O | No Solid |
| 397 | Temp. Cycling | DMF: 30% H$_2$O | Form II |
| 398 | Controlled Cool (4° C.) | DMF: 30% H$_2$O | Form II |
| 399 | Controlled Cool (−21° C.) | DMF: 30% H$_2$O | Form II |
| 400 | Evaporation | DMF: 30% H$_2$O | Form II |
| 401 | Anti-Solvent (IPA) Addition Elevated Temperature | DMF: 30% H$_2$O | Form II |
| 402 | Anti-Solvent (IPA) Addition Ambient Temperature | DMF: 30% H$_2$O | Form II |
| 403 | Anti-Solvent (IPA) Addition (4° C.) | DMF: 30% H$_2$O | Form II |
| 404 | Anti-Solvent (IPA) Addition (−21° C.) | DMF: 30% H$_2$O | Form II |
| 405 | Anti-Solvent (Ethanol) Addition Ambient Temperature | DMF: 30% H$_2$O | Form II |
| 406 | Anti-Solvent (Ethanol) Addition (4° C.) | DMF: 30% H$_2$O | No Solid |
| 407 | Anti-Solvent (Ethanol) Addition (−21° C.) | DMF: 30% H$_2$O | Form II |
| 408 | Temp. Cycling | 1,4-dioxane: 1% H$_2$O | Form II |
| 409 | Controlled Cool (4° C.) | 1,4-dioxane: 1% H$_2$O | No Solid |
| 410 | Controlled Cool (−21° C.) | 1,4-dioxane: 1% H$_2$O | No Solid |
| 411 | Evaporation | 1,4-dioxane: 1% H$_2$O | No Solid |
| 412 | Anti-Solvent (IPA) Addition Elevated Temperature | 1,4-dioxane: 1% H$_2$O | No Solid |
| 413 | Anti-Solvent (IPA) Addition Ambient Temperature | 1,4-dioxane: 1% H$_2$O | No Solid |
| 414 | Anti-Solvent (IPA) Addition (4° C.) | 1,4-dioxane: 1% H$_2$O | No Solid |
| 415 | Anti-Solvent (IPA) Addition (−21° C.) | 1,4-dioxane: 1% H$_2$O | No Solid |
| 416 | Anti-Solvent (Ethanol) Addition Ambient Temperature | 1,4-dioxane: 1% H$_2$O | No Solid |
| 417 | Anti-Solvent (Ethanol) Addition (4° C.) | 1,4-dioxane: 1% H$_2$O | No Solid |
| 418 | Anti-Solvent (Ethanol) Addition (−21° C.) | 1,4-dioxane: 1% H$_2$O | No Solid |
| 419 | Temp. Cycling | 1,4-dioxane: 3% H$_2$O | Form II |
| 420 | Controlled Cool (4° C.) | 1,4-dioxane: 3% H$_2$O | No Solid |
| 421 | Controlled Cool (−21° C.) | 1,4-dioxane: 3% H$_2$O | No Solid |
| 422 | Evaporation | 1,4-dioxane: 3% H$_2$O | Form II |
| 423 | Anti-Solvent (IPA) Addition Elevated Temperature | 1,4-dioxane: 3% H$_2$O | No Solid |
| 424 | Anti-Solvent (IPA) Addition Ambient Temperature | 1,4-dioxane: 3% H$_2$O | No Solid |
| 425 | Anti-Solvent (IPA) Addition (4° C.) | 1,4-dioxane: 3% H$_2$O | No Solid |
| 426 | Anti-Solvent (IPA) Addition (−21° C.) | 1,4-dioxane: 3% H$_2$O | No Solid |
| 427 | Anti-Solvent (Ethanol) Addition Ambient Temperature | 1,4-dioxane: 3% H$_2$O | No Solid |
| 428 | Anti-Solvent (Ethanol) Addition (4° C.) | 1,4-dioxane: 3% H$_2$O | No Solid |
| 429 | Anti-Solvent (Ethanol) Addition (−21° C.) | 1,4-dioxane: 3% H$_2$O | No Solid |
| 430 | Temp. Cycling | 1,4-dioxane: 10% H$_2$O | Form II |
| 431 | Controlled Cool (4° C.) | 1,4-dioxane: 10% H$_2$O | No Solid |
| 432 | Controlled Cool (−21° C.) | 1,4-dioxane: 10% H$_2$O | No Solid |
| 433 | Evaporation | 1,4-dioxane: 10% H$_2$O | Form II |
| 434 | Anti-Solvent (IPA) Addition Elevated Temperature | 1,4-dioxane: 10% H$_2$O | No Solid |
| 435 | Anti-Solvent (IPA) Addition Ambient Temperature | 1,4-dioxane: 10% H$_2$O | No Solid |
| 436 | Anti-Solvent (IPA) Addition (4° C.) | 1,4-dioxane: 10% H$_2$O | No Solid |
| 437 | Anti-Solvent (IPA) Addition (−21° C.) | 1,4-dioxane: 10% H$_2$O | No Solid |
| 438 | Anti-Solvent (Ethanol) Addition Ambient Temperature | 1,4-dioxane: 10% H$_2$O | No Solid |
| 439 | Anti-Solvent (Ethanol) Addition (4° C.) | 1,4-dioxane: 10% H$_2$O | No Solid |
| 440 | Anti-Solvent (Ethanol) Addition (−21° C.) | 1,4-dioxane: 10% H$_2$O | No Solid |
| 441 | Temp. Cycling | MeOH: 5% H$_2$O | Form II |
| 442 | Controlled Cool (4° C.) | MeOH: 5% H$_2$O | No Solid |
| 443 | Controlled Cool (−21° C.) | MeOH: 5% H$_2$O | No Solid |
| 444 | Evaporation | MeOH: 5% H$_2$O | Form II |
| 445 | Anti-Solvent (IPA) Addition Elevated Temperature | MeOH: 5% H$_2$O | Form II |
| 446 | Anti-Solvent (IPA) Addition Ambient Temperature | MeOH: 5% H$_2$O | Form II |
| 447 | Anti-Solvent (IPA) Addition (4° C.) | MeOH: 5% H$_2$O | Form II |
| 448 | Anti-Solvent (IPA) Addition (−21° C.) | MeOH: 5% H$_2$O | Form II |
| 449 | Anti-Solvent (Ethanol) Addition Ambient Temperature | MeOH: 5% H$_2$O | No Solid |
| 450 | Anti-Solvent (Ethanol) Addition (4° C.) | MeOH: 5% H$_2$O | Form II |
| 451 | Anti-Solvent (Ethanol) Addition (−21° C.) | MeOH: 5% H$_2$O | Form II |
| 452 | Temp. Cycling | MeOH: 20% H$_2$O | No Solid |
| 453 | Controlled Cool (4° C.) | MeOH: 20% H$_2$O | Form II |
| 454 | Controlled Cool (−21° C.) | MeOH: 20% H$_2$O | Form II |

TABLE 5-continued

Examples of Preparing Crystalline Forms

| Test | Crystallization Method | Solvent | Results |
|---|---|---|---|
| 455 | Evaporation | MeOH: 20% H₂O | Form II |
| 456 | Anti-Solvent (IPA) Addition Elevated Temperature | MeOH: 20% H₂O | Form II |
| 457 | Anti-Solvent (IPA) Addition Ambient Temperature | MeOH: 20% H₂O | Form II |
| 458 | Anti-Solvent (IPA) Addition (4° C.) | MeOH: 20% H₂O | Form II |
| 459 | Anti-Solvent (IPA) Addition (−21° C.) | MeOH: 20% H₂O | Form II |
| 460 | Anti-Solvent (Ethanol) Addition Ambient Temperature | MeOH: 20% H₂O | Form II |
| 461 | Anti-Solvent (Ethanol) Addition (4° C.) | MeOH: 20% H₂O | Form II |
| 462 | Anti-Solvent (Ethanol) Addition (−21° C.) | MeOH: 20% H₂O | Form I/II |
| 463 | Temp. Cycling | MeOH: 50% H₂O | Form II |
| 464 | Controlled Cool (4° C.) | MeOH: 50% H₂O | Form II |
| 465 | Controlled Cool (−21° C.) | MeOH: 50% H₂O | Form II |
| 466 | Evaporation | MeOH: 50% H₂O | No Solid |
| 467 | Anti-Solvent (IPA) Addition Elevated Temperature | MeOH: 50% H₂O | Form II |
| 468 | Anti-Solvent (IPA) Addition Ambient Temperature | MeOH: 50% H₂O | No Solid |
| 469 | Anti-Solvent (IPA) Addition (4° C.) | MeOH: 50% H₂O | Form II |
| 470 | Anti-Solvent (IPA) Addition (−21° C.) | MeOH: 50% H₂O | No Solid |
| 471 | Anti-Solvent (Ethanol) Addition Ambient Temperature | MeOH: 50% H₂O | Form II |
| 472 | Anti-Solvent (Ethanol) Addition (4° C.) | MeOH: 50% H₂O | Form I |
| 473 | Anti-Solvent (Ethanol) Addition (−21° C.) | MeOH: 50% H₂O | Form I/II |
| 474 | Temp. Cycling | THF: 1% H₂O | Form II |
| 475 | Controlled Cool (4° C.) | THF: 1% H₂O | No Solid |
| 476 | Controlled Cool (−21° C.) | THF: 1% H₂O | No Solid |
| 477 | Evaporation | THF: 1% H₂O | Form II |
| 478 | Anti-Solvent (IPA) Addition Elevated Temperature | THF: 1% H₂O | No Solid |
| 479 | Anti-Solvent (IPA) Addition Ambient Temperature | THF: 1% H₂O | No Solid |
| 480 | Anti-Solvent (IPA) Addition (4° C.) | THF: 1% H₂O | No Solid |
| 481 | Anti-Solvent (IPA) Addition (−21° C.) | THF: 1% H₂O | No Solid |
| 482 | Anti-Solvent (Ethanol) Addition Ambient Temperature | THF: 1% H₂O | No Solid |
| 483 | Anti-Solvent (Ethanol) Addition (4° C.) | THF: 1% H₂O | No Solid |
| 484 | Anti-Solvent (Ethanol) Addition (−21° C.) | THF: 1% H₂O | No Solid |
| 485 | Temp. Cycling | THF: 3% H₂O | Form II |
| 486 | Controlled Cool (4° C.) | THF: 3% H₂O | No Solid |
| 487 | Controlled Cool (−21° C.) | THF: 3% H₂O | No Solid |
| 488 | Evaporation | THF: 3% H₂O | No Solid |
| 489 | Anti-Solvent (IPA) Addition Elevated Temperature | THF: 3% H₂O | No Solid |
| 490 | Anti-Solvent (IPA) Addition Ambient Temperature | THF: 3% H₂O | Form II |
| 491 | Anti-Solvent (IPA) Addition (4° C.) | THF: 3% H₂O | No Solid |
| 492 | Anti-Solvent (IPA) Addition (−21° C.) | THF: 3% H₂O | No Solid |
| 493 | Anti-Solvent (Ethanol) Addition Ambient Temperature | THF: 3% H₂O | No Solid |
| 494 | Anti-Solvent (Ethanol) Addition (4° C.) | THF: 3% H₂O | No Solid |
| 495 | Anti-Solvent (Ethanol) Addition (−21° C.) | THF: 3% H₂O | No Solid |
| 496 | Temp. Cycling | THF: 5% H₂O | No Solid |
| 497 | Controlled Cool (4° C.) | THF: 5% H₂O | No Solid |
| 498 | Controlled Cool (−21° C.) | THF: 5% H₂O | No Solid |
| 499 | Evaporation | THF: 5% H₂O | Form II |
| 500 | Anti-Solvent (IPA) Addition Elevated Temperature | THF: 5% H₂O | No Solid |
| 501 | Anti-Solvent (IPA) Addition Ambient Temperature | THF: 5% H₂O | No Solid |
| 502 | Anti-Solvent (IPA) Addition (4° C.) | THF: 5% H₂O | Form II |
| 503 | Anti-Solvent (IPA) Addition (−21° C.) | THF: 5% H₂O | No Solid |
| 504 | Anti-Solvent (Ethanol) Addition Ambient Temperature | THF: 5% H₂O | No Solid |
| 505 | Anti-Solvent (Ethanol) Addition (4° C.) | THF: 5% H₂O | No Solid |
| 506 | Anti-Solvent (Ethanol) Addition (−21° C.) | THF: 5% H₂O | No Solid |
| 507 | Temp. Cycling | butan-1-ol: 1% H₂O | Form II |
| 508 | Controlled Cool (4° C.) | butan-1-ol: 1% H₂O | No Solid |
| 509 | Controlled Cool (−21° C.) | butan-1-ol: 1% H₂O | No Solid |
| 510 | Evaporation | butan-1-ol: 1% H₂O | Form II |
| 511 | Anti-Solvent (IPA) Addition Elevated Temperature | butan-1-ol: 1% H₂O | No Solid |
| 512 | Anti-Solvent (IPA) Addition Ambient Temperature | butan-1-ol: 1% H₂O | No Solid |
| 513 | Anti-Solvent (IPA) Addition (4° C.) | butan-1-ol: 1% H₂O | No Solid |
| 514 | Anti-Solvent (IPA) Addition (−21° C.) | butan-1-ol: 1% H₂O | No Solid |
| 515 | Anti-Solvent (Ethanol) Addition Ambient Temperature | butan-1-ol: 1% H₂O | No Solid |
| 516 | Anti-Solvent (Ethanol) Addition (4° C.) | butan-1-ol: 1% H₂O | No Solid |
| 517 | Anti-Solvent (Ethanol) Addition (−21° C.) | butan-1-ol: 1% H₂O | No Solid |
| 518 | Temp. Cycling | butan-1-ol: 3% H₂O | Form II |
| 519 | Controlled Cool (4° C.) | butan-1-ol: 3% H₂O | No Solid |
| 520 | Controlled Cool (−21° C.) | butan-1-ol: 3% H₂O | No Solid |
| 521 | Evaporation | butan-1-ol: 3% H₂O | Form II |
| 522 | Anti-Solvent (IPA) Addition Elevated Temperature | butan-1-ol: 3% H₂O | No Solid |
| 523 | Anti-Solvent (IPA) Addition Ambient Temperature | butan-1-ol: 3% H₂O | No Solid |
| 524 | Anti-Solvent (IPA) Addition (4° C.) | butan-1-ol: 3% H₂O | No Solid |
| 525 | Anti-Solvent (IPA) Addition (−21° C.) | butan-1-ol: 3% H₂O | No Solid |
| 526 | Anti-Solvent (Ethanol) Addition Ambient Temperature | butan-1-ol: 3% H₂O | No Solid |
| 527 | Anti-Solvent (Ethanol) Addition (4° C.) | butan-1-ol: 3% H₂O | No Solid |
| 528 | Anti-Solvent (Ethanol) Addition (−21° C.) | butan-1-ol: 3% H₂O | No Solid |
| 529 | Temp. Cycling | butan-1-ol: 5% H₂O | Form II |
| 530 | Controlled Cool (4° C.) | butan-1-ol: 5% H₂O | No Solid |
| 531 | Controlled Cool (−21° C.) | butan-1-ol: 5% H₂O | No Solid |

TABLE 5-continued

Examples of Preparing Crystalline Forms

| Test | Crystallization Method | Solvent | Results |
|---|---|---|---|
| 532 | Evaporation | butan-1-ol: 5% H₂0 | Form II |
| 533 | Anti-Solvent (IPA) Addition Elevated Temperature | butan-1-ol: 5% H₂0 | No Solid |
| 534 | Anti-Solvent (IPA) Addition Ambient Temperature | butan-1-ol: 5% H₂0 | Form II |
| 535 | Anti-Solvent (IPA) Addition (4° C.) | butan-1-ol: 5% H₂0 | No Solid |
| 536 | Anti-Solvent (IPA) Addition (−21° C.) | butan-1-ol: 5% H₂0 | No Solid |
| 537 | Anti-Solvent (Ethanol) Addition Ambient Temperature | butan-1-ol: 5% H₂0 | No Solid |
| 538 | Anti-Solvent (Ethanol) Addition (4° C.) | butan-1-ol: 5% H₂0 | No Solid |
| 539 | Anti-Solvent (Ethanol) Addition (−21° C.) | butan-1-ol: 5% H₂0 | No Solid |
| 540 | Temp. Cycling | 1,4-dioxane | Form I |
| 541 | Evaporation | 1,4-dioxane | Form I/II |
| 542 | Anti-Solvent Addition | 1,4-dioxane | No Solid |
| 543 | Temp. Cycling | 1-butanol | Form I |
| 544 | Evaporation | 1-butanol | Form I/II |
| 545 | Anti-Solvent (Hexane) Addition (4° C.) | 1-butanol | Form III |
| 546 | Temp. Cycling | ethanol | Form I |
| 547 | Evaporation | ethanol | Form II |
| 548 | Anti-Solvent (Hexane) Addition (4° C.) | ethanol | Form I |
| 549 | Temp. Cycling | acetone | Form I |
| 550 | Evaporation | acetone | Form II |
| 551 | Anti-Solvent (Hexane) Addition (4° C.) | acetone | Form III |
| 552 | Temp. Cycling | benzonitrile | Form I |
| 553 | Evaporation | benzonitrile | Form II |
| 554 | Anti-Solvent (Hexane) Addition (4° C.) | benzonitrile | Form II |
| 555 | Temp. Cycling | cyclohexane | Form I |
| 556 | Evaporation | cyclohexane | Form II |
| 557 | Anti-Solvent (Hexane) Addition (4° C.) | cyclohexane | No Solid |
| 558 | Temp. Cycling | DCM | Form I |
| 559 | Evaporation | DCM | Form II |
| 560 | Anti-Solvent (Hexane) Addition (4° C.) | DCM | Form III |
| 561 | Temp. Cycling | DMSO | Form I |
| 562 | Evaporation | DMSO | Form II/II |
| 563 | Anti-Solvent (Hexane) Addition (4° C.) | DMSO | No Solid/No Solid |
| 564 | Temp. Cycling | EtOAc | Form I |
| 565 | Evaporation | EtOAc | Form II |
| 566 | Anti-Solvent (Hexane) Addition (4° C.) | EtOAc | Form III |
| 567 | Temp. Cycling | Heptane | Form I |
| 568 | Evaporation | Heptane | Form I/II |
| 569 | Anti-Solvent (Hexane) Addition (4° C.) | Heptane | No Solid/No Solid |
| 570 | Temp. Cycling | IPA | Form I |
| 571 | Evaporation | IPA | Form I/II |
| 572 | Anti-Solvent (Hexane) Addition (4° C.) | IPA | No Solid |
| 573 | Temp. Cycling | IPA: Water (1%) | Form I |
| 574 | Evaporation | IPA: Water (1%) | Form II |
| 575 | Anti-Solvent (Hexane) Addition (4° C.) | IPA: Water (1%) | No Solid/No Solid |
| 576 | Temp. Cycling | MeCN | Form I |
| 577 | Evaporation | MeCN | Form II |
| 578 | Anti-Solvent (Hexane) Addition (4° C.) | MeCN | Form I/III |
| 579 | Temp. Cycling | MeCN: Water (1%) | Form I |
| 580 | Evaporation | MeCN: Water (1%) | Form I/II |
| 581 | Anti-Solvent (Hexane) Addition (4° C.) | MeCN: Water (1%) | No Solid |
| 582 | Temp. Cycling | MEK | Form I |
| 583 | Evaporation | MEK | Form I/II |
| 584 | Anti-Solvent (Hexane) Addition (4° C.) | MEK | Form III |
| 585 | Temp. Cycling | MeOAc | Form I |
| 586 | Evaporation | MeOAc | Form II |
| 587 | Anti-Solvent (Hexane) Addition (4° C.) | MeOAc | Form III |
| 588 | Temp. Cycling | MeOH | Form I |
| 589 | Evaporation | MeOH | Form I/II |
| 590 | Anti-Solvent (Hexane) Addition (4° C.) | MeOH | Form III |
| 591 | Temp. Cycling | MIBK | Form I |
| 592 | Evaporation | MIBK | Form II |
| 593 | Anti-Solvent (Hexane) Addition (4° C.) | MIBK | No Solid |
| 594 | Temp. Cycling | Nitromethane | Form I |
| 595 | Evaporation | Nitromethane | Form II |
| 596 | Anti-Solvent (Hexane) Addition (4° C.) | Nitromethane | Form I |
| 597 | Temp. Cycling | TBME | Form I |
| 598 | Evaporation | TBME | Form II |
| 599 | Anti-Solvent (Hexane) Addition (4° C.) | TBME | Form I |
| 600 | Temp. Cycling | THF | Form I |
| 601 | Evaporation | THF | Form II |
| 602 | Anti-Solvent (Hexane) Addition (4° C.) | THF | Form I/III |
| 603 | Temp. Cycling | THF: water (1%) | Form I |
| 604 | Evaporation | THF: water (1%) | Form I/II |
| 605 | Anti-Solvent (Hexane) Addition (4° C.) | THF: water (1%) | No Solid |
| 606 | Temp. Cycling | toluene | Form I |
| 607 | Evaporation | toluene | Form II |
| 608 | Anti-Solvent (Hexane) Addition (4° C.) | toluene | Form III |
| 609 | Temp. Cycling | water | No Solid |
| 610 | Evaporation | water | Form I/II |
| 611 | Anti-Solvent (Hexane) Addition (4° C.) | water | Form III |

Example 2

Intrinsic Dissolution Studies

The intrinsic dissolution rates for Forms I, II, and III were measured at pH conditions of 1.0, 4.5 and 6.7. The results are reproduced below in TABLE 6. In each case, complete dissolution was achieved in less than 3 minutes. Surprisingly, a pH dependence was observed for Form II; with the intrinsic dissolution rate increasing with the pH. In contrast, Forms I and III appear to dissolve at rates independent of pH.

TABLE 6

Calculated Intrinsic Dissolution Rates (mg/cm²/s)

| | 1.0 | 4.5 | 6.7 |
|---|---|---|---|
| Form I | 0.41 | 0.44 | 0.37 |
| Form II | 0.26 | 0.34 | 0.62 |
| Form III | 0.49 | 0.44 | 0.45 |

Example 3

Solubility Studies

The solubility of L-ornithine phenyl acetate was approximated according to methods disclosed above. 24 solvents systems were tested: 1,4 dioxane, 1-butanol, ethanol, acetone, benzonitrile, cyclohexane, DCM, DMSO, EtOAc, Heptane, IPA, IPA (1% $H_2O$), MeCN, MeCn (1% $H_2O$), MEK, MeOAc, methanol, MIBK, Nitromethane, THF, THF (1% $H_2O$), Toluene and water. L-ornithine phenyl acetate exhibited a solubility in water, whereas L-ornithine phenyl acetate was substantially insoluble in the remaining solvent systems.

Slurries of L-ornithine phenyl acetate in water were also prepared and the slurry was filtered. The filtrate concentration was analyzed by HPLC, and the results show the solubility of L-ornithine phenyl acetate to be about 1.072 mg/mL.

HPLC determinations of solubility were also completed for five solvents: ethanol, acetone, methanol, DMSO and IPA. These results are summarized in TABLE 7.

TABLE 7

HPLC Solubility Determinations

| Solvent | Solubility (mg/mL) | Peak Area | Comments |
|---|---|---|---|
| EtOH | <0.0033 | N/A | Small peak |
| Acetone | 0 | 0 | API content beyond the lower limit of quantification (LLOQ) |
| MeOH | 0.0033 | 1906.75 | Resolved peak |
| DMSO | >0.0033 | N/A | Shoulder on DMSO peak |
| IPA | 0 | 0 | API content beyond the LLOQ |

These results indicate that both acetone and IPA are suitable as anti-solvents for precipitating L-ornithine phenyl acetate. In contrast, solvents with measurable solubility are less favorable for precipitating crystalline forms of L-ornithine phenyl acetate.

Finally, the solubility of L-ornithine phenyl acetate was determined in various mixtures of IPA and water using HPLC. The results are shown in TABLE 8.

TABLE 8

HPLC Solubility Determinations (IPA/Water)

| % IPA | Peak Area | Solubility (mg/mL) |
|---|---|---|
| 100 | 0 | 0 |
| 90 | 295 | 0.0054 |
| 80 | 2634 | 0.0455 |
| 70 | 8340 | 0.1433 |

Example 4

Small-Scale Batch Process to Produce L-Ornithine Phenyl Acetate

About 8.4 g (0.049 moles) of L-ornithine HCl was dissolved in 42 mL $H_2O$ and, separately, about 11.4 g of silver benzoate was dissolved in 57 mL DMSO. Subsequently, the silver benzoate solution was added to the L-ornithine HCl solution. Combining the two mixtures resulted in an immediate, exothermic precipitation of a creamy white solid (AgCl). The solid was removed by vacuum filtration and retaining the filtrate (L-ornithine benzoate in solution). 200 mL of IPA was added to the filtrate and the mixture was cooled to 4° C. A crystalline solid precipitated after about 3 hours (L-ornithine benzoate) which was isolated by vacuum filtration. Yield: 60%

7.6 g (0.03 moles) of the L-ornithine benzoate was dissolved in 38 mL $H_2O$ and about 4.4 g of sodium phenyl acetate was dissolved 22 mL H2O. Subsequently, the sodium phenyl acetate solution was added to the L-ornithine benzoate solution and left to stir for about 10 minutes About 240 mL of IPA (8:2 IPA:$H_2O$) was added and the solution stirred for 30 minutes before cooling to 4° C. A crystalline solid precipitated after about 3 hrs at 4° C. (L-ornithine phenyl acetate). The precipitate was isolated by vacuum filtration and washed with 48-144 mL of IPA. Yield: 57%

Example 5

Large-Scale Batch Process to Produce L-Ornithine Phenyl Acetate

Two separate batch of L-ornithine phenyl acetate were prepared as follows:

About 75 Kg of L-Ornithine monohydrochloride was dissolved in 227 kg of water. To the resulting solution was added 102 Kg of silver benzoate dissolved in 266 kg of DMSO at room temperature within 2 hours. Initially, a strong exothermy was observed and the silver chloride precipitated. The receiver containing the solution was then washed with 14 Kg of DMSO that was added to the reaction mass. In order to remove the silver chloride formed, the reaction mass was filtered over a lens filter prepared with 10 kg of Celite and a GAF filter of 1 mm. After filtration, the filter was washed with an additional 75 kg of water. The reaction mass was then heated at 35±2° C. and 80 kg of sodium phenyl acetate was added. At this point the reaction mass was stirred at 35±2° C. for at least 30 minutes.

In order to precipitate the final API, 353 kg of isopropyl alcohol was added to the reaction mass. The reaction mass was then cooled to 0±3° C. within 6 hours, stirred for 1 hour and then the product isolated in a centrifuge.

About 86 kg of finished wet produce was obtained. The product was then dried at 40±5° C. for about 6.5 to 8 hours to provide about 75 kg of L-ornithine phenyl acetate. Yield: 63.25. TABLE 9 summarizes measurements relating to the final product.

TABLE 9

Analytical Results for Large-scale Batch Process

| Test | Batch 1 | Batch 2 |
|---|---|---|
| Purity | 98.80% | 98.74% |
| Benzoate | 0.17% | 0.14% |
| Silver | 28 ppm | 157 ppm |
| Chloride | 0.006% | 0.005% |
| Sodium | 7 ppm | 26 ppm |
| Total Impurities | 0.17% | 0.14% |
| Physical Form | Form II | Form II |

Example 6

Reducing Silver Content in L-Ornithine Phenyl Acetate

Batch 2 from Example 5 exhibited high amounts of silver (157 ppm), and therefore procedures were tested for reducing the silver content. Nine trials were completed; each generally including dissolving about 20 g of L-ornithine phenyl acetate from Batch 2 into 1.9 parts water, and then subsequently adding 10.8 parts IPA. A crystalline form was isolated at 0° C. by filtration.

For four trials, 8.0 mg or 80 mg of heavy metal scavengers SMOPEX 102 or SMOPEX 112 were added to the aqueous solution and stirred for 2 hours. The scavengers failed to reduce the silver content below 126 ppm. Meanwhile, another trial applied the general conditions disclosed above and reduced the silver content to 179 ppm. In still another trial, the L-ornithine phenyl acetate was slurried in a solution of IPA, rather than crystallized; however this trial also failed to reduce the silver content below 144 ppm.

The last three trials included adding diluted HCl to the solution to precipitate remaining amount of silver as AgCl. The precipitate was then removed by filtration before The three trials included adding: (1) 1.0 g of 0.33% HCl at 20° C.; (2) 1.0 g of 0.33% HCl at 30° C.; and (3) 0.1 g of 3.3% HCl at 20° C. The three trials reduced the silver content to 30 ppm, 42 ppm, and 33 ppm, respectively, and each trial yielding greater than 90% L-ornithine phenyl acetate. Accordingly, the addition of HCl was effective in reducing the amount of residual silver.

Example 6

Process for Preparing L-Ornithine Phenyl Acetate without an Intermediate Salt

As a general procedure, L-ornithine hydrochloride was suspended in a solvent. After that the reaction mass was heated and a base, sodium methoxide, was added. NaCl formed and was removed from the system by filtration. The reaction mass was cooled and a molar equivalent of phenyl acetic acid was added to the reaction mass in order to form L-ornithine phenyl acetate. The final product was isolated, washed and dried. A summary of the trial for this process is provided in TABLE 10.

TABLE 10

Process Trials

| Trial | Base | Eq. of Base | Solvent |
|---|---|---|---|
| 1 | NaOMe 21% in MeOH | 1.0 eq. | MeOH |
| 2 | NaOMe 21% in MeOH | 0.95 eq. | IPA |
| 3 | NaOMe 21% in EtOH | 1.0 eq. | EtOH |
| 4 | NaOMe 21% in MeOH | 1.0 eq. | MeOH |
| 5 | NaOMe 21% in MeOH | 1.0 eq. | MeOH w/IPA for precipitation |
| 6 | NaOMe 21% in MeOH | 1.0 eq. | Acetonitrile |
| 7 | NaOMe 21% in MeOH | 1.0 eq. | Water/IPA |
| 8 | NaOMe 21% in MeOH | 1.0 eq. | Water/IPA |
| 9 | NaOMe 21% in MeOH | 1.0 eq. | n-butanol |

The resulting L-ornithine phenyl acetate was found to exhibit high amounts of chloride (at least about 1% by weight), and presumably include similar amounts of sodium. The yields were about 50% for Trials 2, 4, and 5.

Example 7

Thermal Stability Studies of Forms I, II, and III

Samples of Forms I, II and III were stored at increased temperatures and designated conditions as outlined in TABLE 11. The vacuum applied 600 psi to achieve the reduced pressure. The final compositions were tested by XRPD, NMR, IR and HPLC to determine any changes to the material.

Most notably, Form III does not transition to Form II under vacuum at 120° C., but rather exhibits greater chemical degradation compared to Forms I and II under these conditions. Meanwhile, Form III converts to Form II and exhibits substantial chemical degradation at 120° C. without a vacuum.

Form I converted to Form II in all the trials, but most interestingly, Form I exhibits substantial chemical degradation at 120° C. without a vacuum. Thus, the conversion from Form I does not exhibit the same chemical stability as Form II, which is surprising considering the material readily converts to Form II.

Form II was stable and did not chemically degrade in all of the trials. Thus, Form II is the most stable. Meanwhile, Form III is more stable than Form I, but both forms exhibit substantial chemical degradation at 120° C. without a vacuum.

TABLE 11

Thermal Stability Trials

| Trial | Initial Form | Temperature | Condition | Period | Results |
|---|---|---|---|---|---|
| 1 | Form I | 80° C. | no vacuum | 7 days | Form II, no degradation |
| 2 | Form I | 80° C. | vacuum | 7 days | Form II, no degradation |
| 3 | Form I | 80° C | no vacuum | 14 days | Form II, no degradation |
| 4 | Form I | 80° C. | vacuum | 14 days | Form II, no degradation |
| 5 | Form II | 80° C. | no vacuum | 7 days | Form II, no degradation |
| 6 | Form II | 80° C. | vacuum | 7 days | Form II, no degradation |
| 7 | Form II | 80° C. | no vacuum | 14 days | Form II, no degradation |
| 8 | Form II | 80° C. | vacuum | 14 days | Form II, no degradation |
| 5 | Form III | 80° C. | no vacuum | 7 days | Form III, no degradation |
| 5 | Form III | 80° C. | no vacuum | 14 days | Form III, no degradation |
| 6 | Form I | 120° C. | no vacuum | 7 days | Form II (>96% API) |
| 7 | Form I | 120° C. | vacuum | 7 days | Form II (>99.9% API) |
| 8 | Form I | 120° C. | no vacuum | 14 days | Form II (37% API) |
| 9 | Form I | 120° C. | vacuum | 14 days | Form II (>96% API) |
| 8 | Form II | 120° C. | no vacuum | 7 days | Form II (98.6% API) |
| 9 | Form II | 120° C. | vacuum | 7 days | Form II (98.7% API) |
| 10 | Form II | 120° C. | no vacuum | 14 days | Form II (>95% API) |
| 11 | Form II | 120° C. | vacuum | 14 days | Form II (>95% API) |
| 10 | Form III | 120° C. | no vacuum | 7 days | Form II (<30% API) |
| 11 | Form III | 120° C. | vacuum | 7 days | Form III (>95% API) |
| 12 | Form III | 120° C. | no vacuum | 14 days | Form II (<30% API) |
| 14 | Form III | 120° C. | vacuum | 14 days | Form III (88.8% API) |

HPLC results for the trials exhibiting chemical degradation (e.g., Trial 10 from TABLE 11) are summarized in TABLE 12. Each degraded material exhibits common peaks at relative retention times (RRT) of 1.9, 2.2, 2.4, and 2.7, which suggests a common degradation pathway for different forms.

TABLE 12

HPLC Results for Degraded Samples

| HPLC ID | Sample ID | Form Tested | Stability Test | Timepoint (day) | Main Peak Retention Time (min) | | Degradation/Impuirty Peak(s) | |
|---|---|---|---|---|---|---|---|---|
| | | | | | Retention Time (min) | % Peak Area | Retention Time (min) | % Peak Area |
| 39 | W00045/45/3 | III | 120° C. ambient pressure | 7 | 2.857 | 35.786 | 6.763 7.582 | 6.103 45.161 |
| 42 | W00045/45/6 | III | 120° C. under vacuum (ca. 600 psi) | 7 | 2.787 | 88.885 | 7.598 | 9.389 |
| 51 | W00045/45/1 | I | 120° C. ambient pressure | 14 | 3.499 | 37.826 | 6.766 7.569 9.707 | 3.948 42.525 3.628 |
| 53 | W00045/45/3 | III | 120° C. ambient pressure | 14 | 3.476 | 30.394 | 6.763 7.583 | 5.975 56.459 |
| 56 | W00045/45/6 | III | 120° C. under vacuum (ca. 600 psi) | 14 | 3.400 | 87.389 | 7.555 | 11.500 |

Example 8

Oxygen Stability Studies of Forms I, II, and III

Samples of Forms I, II and III were stored in 100% oxygen environments for 7 or 14 days and analyzed by NMR and IR. The results establish that Forms I and II show no signs of degradation after 14 days. Only IR results were completed for Form III at 7 days, and these results confirm there was no significant degradation. TLC results for all samples indicated a single spot with similar $R_f$ values.

Example 9

UV Stability Studies of Forms I, II, and III

Samples of Forms I, II and III were exposed to ultraviolet (UV) radiation for 7 or 14 days. A CAMAG universal UV Lampe applied radiation to the samples with setting of 254 mμ. NMR and IR results show no degradation of Forms I and II after 14 days. Similarly, Form III exhibits no degradation after 7 days as determined by NMR and IR. TLC results for all samples indicated a single spot with similar $R_f$ values.

Example 10 pH Stability Studies of Forms I, II, and III

A slurry of Forms I, II and III were formed with water and the pH value adjusted to either 1.0, 4.0, 7.0, 10.0, and 13.2. The slurries were stored for 7 or 14 days, and subsequently the solids were removed by filtration. Form I converted to Form II in all of the samples. NMR and IR results show Forms I and II did not degrade after 14 days in the varied pHs, and similarly HPLC results show about 98% purity or more for these samples. Form III also exhibited no degradation after 7 days according to NMR and IR results. HPLC tests show about 95% purity or more; however IR results show Form III converted to Form II over the 7-day test. TLC results for all samples indicated a single spot with similar $R_f$ values.

Example 11

Compression Studies of Forms I, II, and III

Samples of Forms I, II and III were subjected to 3 tons of force using a Moore Hydraulic Press for about 90 minutes. The resultant tablet's mass, diameter and thickness were measured to determine the density. The tablets were also analyzed by NMR and IR. Form I transitioned to a composition of Form II with a density of 1.197 kg/m$^3$. Form II did not exhibit a transition and had a final density of 1.001 kg/m$^3$. Finally, Form III did not exhibit a transition and had a final density of 1.078 kg/m$^3$.

Example 12

Process for Producing L-Ornithine Phenyl Acetate via an Acetate Intermediate

Dissolve 25 mg of L-ornithine HCl 5 vols of H2O, and then add excess acetic acid (about 5 vols) to form a slurry. Subject the slurry to temperature cycling between 25° and 40° C. every 4 hours for about 3 days. Add 1 equivalent of phenylacetic acid (with respect to L-ornithine) and stir for about 4-6 hrs (possibly heat). Use IPA as an anti-solvent, add enough to obtain a ratio of 70:30 (IPA:H$_2$O). Isolate by vacuum filtration and dry for about 4-8 hrs at 80° C. to remove any residual acetic acid.

What is claimed is:

1. A process for making L-ornithine phenylacetate, comprising:
   forming a solution of L-ornithine;
   adding a pH modifier to the solution;
   adding phenylacetic acid to the solution; and
   isolating L-ornithine phenylacetate from the solution.

2. The process of claim 1, wherein the solution comprises water.

3. The process of claim 1, wherein said isolating L-ornithine phenylacetate from the solution comprises a filtration of the solution.

4. The process of claim 1, wherein said isolating L-ornithine phenylacetate from the solution comprises crystallizing L-ornithine phenylacetate from the solution.

5. The process of claim 4, wherein said crystallizing L-ornithine phenylacetate further comprises cooling the solution.

6. The process of claim 4, further comprising adding a second solvent to the solution.

7. The process of claim 6, wherein the second solvent comprises one or more alcohols.

8. The process of claim 7, wherein the one or more alcohols are selected from the group consisting of methanol, ethanol, 1-propanol, isopropanol, ethylene glycol, 2-butanol, 3-methyl-1-butanol, and combinations thereof.

9. The process of claim 8, wherein the second solvent comprises ethanol.

10. The process of claim 6, wherein said crystallizing L-ornithine phenylacetate comprises cooling the solution.

11. The process of claim 10, further comprising recrystallizing the isolated L-ornithine phenylacetate.

12. The process of claim 4, wherein said crystallizing provides a composition comprising a crystalline form of L-ornithine phenylacetate, wherein said crystalline form exhibits an X-ray powder diffraction pattern comprising at least three characteristic peaks, wherein said characteristic peaks are selected from the group consisting of peaks at approximately 6.0°, 13.9°, 14.8°, 17.1°, 17.8° and 24.1° 2θ.

13. The process of claim 4, wherein said crystallizing provides a composition comprising a crystalline form of L-ornithine phenylacetate, wherein said crystalline form exhibits an X-ray powder diffraction pattern comprising at least three characteristic peaks, wherein said characteristic peaks are selected from the group consisting of peaks at approximately 5.8°, 14.1°, 18.6°, 19.4°, 22.3° and 24.8° 2θ.

14. The process of claim 4, wherein said crystallizing provides a composition comprising a crystalline form of L-ornithine phenylacetate, wherein said crystalline form exhibits an X-ray powder diffraction pattern comprising at least three characteristic peaks, wherein said characteristic peaks are selected from the group consisting of peaks at approximately 4.9°, 13.2°, 17.4°, 20.8° and 24.4° 2θ.

15. The process of claim 6, wherein said crystallizing provides a composition comprising a crystalline form of L-ornithine phenylacetate, wherein said crystalline form exhibits an X-ray powder diffraction pattern comprising at least three characteristic peaks, wherein said characteristic peaks are selected from the group consisting of peaks at approximately 6.0°, 13.9°, 14.8°, 17.1°, 17.8° and 24.1° 2θ.

16. The process of claim 6, wherein said crystallizing provides a composition comprising a crystalline form of L-ornithine phenylacetate, wherein said crystalline form exhibits an X-ray powder diffraction pattern comprising at least three characteristic peaks, wherein said characteristic peaks are selected from the group consisting of peaks at approximately 5.8°, 14.1°, 18.6°, 19.4°, 22.3° and 24.8° 2θ.

17. The process of claim 6, wherein said crystallizing provides a composition comprising a crystalline form of L-ornithine phenylacetate, wherein said crystalline form exhibits an X-ray powder diffraction pattern comprising at least three characteristic peaks, wherein said characteristic peaks are selected from the group consisting of peaks at approximately 4.9°, 13.2°, 17.4°, 20.8° and 24.4° 2θ.

* * * * *

UNITED STATES PATENT AND TRADEMARK OFFICE
CERTIFICATE OF CORRECTION

PATENT NO. : 10,550,069 B2
APPLICATION NO. : 16/037655
DATED : February 4, 2020
INVENTOR(S) : Keith Anderson et al.

Page 1 of 2

It is certified that error appears in the above-identified patent and that said Letters Patent is hereby corrected as shown below:

In the Specification

Column 8, Line 2, delete "benzensulfonate," and insert --benzenesulfonate,--.

Column 8, Line 44, delete "diisopropoyl" and insert --diisopropyl--.

Column 8, Line 45, delete "tdiethyl" and insert --diethyl--.

Column 10, Lines 2-8 (approx.), delete " 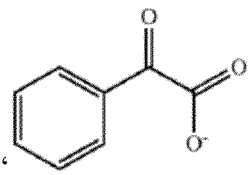 " and insert -- 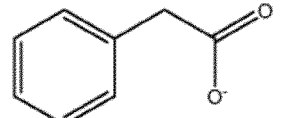 --.

Column 10, Line 8 (approx.), delete "(III)" and insert --(V)--.

Column 10, Line 48 (approx.), delete "benzensulfonate," and insert --benzenesulfonate,--.

Column 12, Lines 15-19, delete " 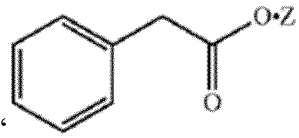 " and insert -- 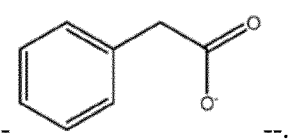 --.

Column 14, Line 10, delete "benzensulfonate," and insert --benzenesulfonate,--.

Column 17, Line 1, delete "diemthylcarbonate," and insert --dimethylcarbonate,--.

Column 17, Line 3, delete "3-nethyl" and insert --3-methyl--.

Column 19, Line 25, delete "may by" and insert --may be--.

Signed and Sealed this
Nineteenth Day of May, 2020

Andrei Iancu
*Director of the United States Patent and Trademark Office*

CERTIFICATE OF CORRECTION (continued)
U.S. Pat. No. 10,550,069 B2

Column 19, Line 36, delete "Θ." and insert --2Θ.--.

Column 24, Line 50, delete "Seimens" and insert --Siemens--.

Column 25, Line 18, delete "Seimens" and insert --Siemens--.

Column 25, Line 21, delete "Seimens" and insert --Siemens--.

Column 25, Line 41, delete "d5000" and insert --D5000--.

Column 45, Line 3, delete "MeCn" and insert --MeCN--.

Column 46, Line 3, delete "H2O." and insert --$H_2O$.--.

Column 49-50, TABLE 12, Line 2, delete "Impuirty" and insert --Impurity--.

Column 49, Line 38, delete "mµ." and insert --µm.--.

Column 50, Line 34, delete "H2O," and insert --$H_2O$,--.